(12) United States Patent
Springer et al.

(10) Patent No.: US 8,877,893 B2
(45) Date of Patent: Nov. 4, 2014

(54) STABILIZED LOW AFFINITY CONFORMATION OF INTEGRINS FOR DRUG DISCOVERY

(75) Inventors: Timothy A. Springer, Chestnut Hill, MA (US); Bing Hao Luo, Baton Rouge, LA (US)

(73) Assignee: Children's Medical Center Corporation, Boston, MA (US)

( * ) Notice: Subject to any disclaimer, the term of this patent is extended or adjusted under 35 U.S.C. 154(b) by 376 days.

(21) Appl. No.: 12/645,958

(22) Filed: Dec. 23, 2009

(65) Prior Publication Data

US 2010/0167418 A1 Jul. 1, 2010

Related U.S. Application Data

(60) Provisional application No. 61/141,145, filed on Dec. 29, 2008.

(51) Int. Cl.
*C07K 14/00* (2006.01)
*G01N 33/566* (2006.01)
*C07K 14/705* (2006.01)

(52) U.S. Cl.
CPC ...... *C07K 14/70546* (2013.01); *G01N 2333/70546* (2013.01); *G01N 2500/04* (2013.01); *G01N 33/566* (2013.01)
USPC .......................................................... 530/350

(58) Field of Classification Search
None
See application file for complete search history.

(56) References Cited

U.S. PATENT DOCUMENTS

| 7,241,869 B2 * | 7/2007 | Springer et al. ............... 530/350 |
| 2002/0123614 A1 * | 9/2002 | Springer et al. ............... 530/350 |
| 2003/0054440 A1 * | 3/2003 | Mayo et al. ................... 435/69.1 |
| 2005/0260192 A1 * | 11/2005 | Springer et al. ........... 424/130.1 |

OTHER PUBLICATIONS

Zhu et al. Structure of a complete integrin ectodomain in a physiologic resting state and activation and deactivation by applied forces. Mol Cell. Dec 26, 2008;32(6):849-61.*
Li et al. Characterization of the monomeric form of the transmembrane and cytoplasmic domains of the integrin beta 3 subunit by NMR spectroscopy. Biochemistry. Dec. 31, 2002;41(52):15618-24.*
Donald et al. Identification of Stalk Mutations That Stabilize the High Affinity Conformation of allbβ3 by Negative Design. 51st Annual Meeting of the American-Society-of-Hematology. New Orleans, LA, USA. Dec. 5-8, 2009. Amer Soc Hematol. Abstract Number:4017.*
Xiong, et al. (2002). Crystal structure of the extracellular segment of integrin aVb3 in complex with an Arg-Gly-Asp ligand. Science, 296, 151-155.
Ye, et al. (2008). Integrin alpha IIb beta 3 in a membrane environment remains the same height after Mn2+ activation when observed by cryoelectron tomography. J Mol Biol 378, 976-986.
Zhu, et al. (2007a). Tests of the extension and deadbolt models of integrin activation. The Journal of biological chemistry 282 (16), 11914-11920.
Zhu, et al. (2007b). Requirement of a and b subunit transmembrane helix separation for integrin outside-in signaling. Blood 110, 2475-2483.
Adair, et al. (2002). Three-dimensional model of the human platelet integrin allbb3 based on electron cryomicroscopy and x-ray crystallography. Proceedings of the National Academy of Sciences of the United States of America 99, 14059-14064.
Alon, et al. (2007). Force as a Facilitator of Integrin Conformational Changes during Leukocyte Arrest on Blood Vessels and Antigen-Presenting Cells. Immunity 26, 17-27.
Arnaout, et al. (2005). Integrin structure, allostery, and bidirectional signaling. Annu. Rev. Cell Dev. Biol. 21, 381-410.
Astrof, et al. (2006). Importance of force linkage in mechanochemistry of adhesion receptors. Biochemistry 45, 15020-15028.
Beglova, et al. (2002). Cysteine-rich module structure reveals a fulcrum for integrin rearrangement upon activation. Nat. Struct. Biol. 9 (4), 282-287.
Broussard, et al. (2008). Asymmetric focal adhesion disassembly in motile cells. Curr Opin Cell Biol 20, 85-90.
Calderwood, D.A. (2004). Integrin activation. J. Cell Sci. 117, 657-666.
Chen, et al. (2003). Bistable regulation of integrin adhesiveness by a bipolar metal ion cluster. Nat. Struct. Biol. 10 (12), 995-1001.
Davis, et al., (2007). MolProbity: all-atom contacts and structure validation for proteins and nucleic acids. Nucleic acids research 35, W375-383.
Evans, et al. (2007). Forces and bond dynamics in cell adhesion. Science, 316, 1148-1153.
Frank, et al. (1996). SPIDER and WEB: processing and visualization of images in 3D electron microscopy and related fields. J. Struct. Biol. 116, 190-199.
Giannone, et al. (2003). Talin1 is critical for force-dependent reinforcement of initial integrin-cytoskeleton bonds but not tyrosine kinase activation. The Journal of cell biology 163, 409-419.
Honda, et al. (1995). Topography of ligand-induced binding sites, including a novel cation-sensitive epitope (AP5) at the amino terminus, of the human integrin b3 subunit. The Journal of biological chemistry 270, 11947-11954.
Hu, et al. (2007). Differential transmission of actin motion within focal adhesions. Science, 315, 111-115.
Iwasaki, et al. (2005). Electron tomography reveals diverse conformations of integrin allbb3 in the active state. J. Struct. Biol. 150, 259-267.
Janin, J. (1997). Specific versus non-specific contacts in protein crystals. Nature Struc.Biol. 4, 973-974.

(Continued)

*Primary Examiner* — Maher Haddad
(74) *Attorney, Agent, or Firm* — Nixon Peabody LLP; David S. Resnick; Leena H. Karttunen Contarino

(57) ABSTRACT

The methods and compositions described herein are based, in part, on the discovery that the introduction of a disulfide bond into an integrin polypeptide by the substitution of at least one cysteine residue in the polypeptide permits stabilization of the integrin in a "closed/inactive" state. This stabilizing disulfide bond permits integrins to be screened for a candidate molecule that can bind to the closed state. In particular, this approach can be used to screen for agents that bind to the closed state of an integrin polypeptide, and are useful as therapeutic treatments to prevent integrin activation.

3 Claims, 20 Drawing Sheets

(56) References Cited

OTHER PUBLICATIONS

Jiang, et al. (2003). Two-piconewton slip bond between fibronectin and the cytoskeleton depends on talin. Nature 424, 334-337.

Jin, et al. (2004). Conversion between three conformational states of integrin I domains with a C-terminal pull spring studied with molecular dynamics. Structure 12, 2137-2147.

Kaizuka, et al. (2007). Mechanisms for segregating T cell receptor and adhesion molecules during immunological synapse formation in Jurkat T cells. Proceedings of the National Academy of Sciences of the United States of America 104, 20296-20301.

Kim, et al. (2004). The primacy of affinity over clustering in regulation of adhesiveness of the integrin aLb2. J. Cell Biol. 167, 1241-1253.

Krissinel, et al. (2004). Secondary-structure matching (SSM), a new tool for fast protein structure alignment in three dimensions. Acta Crystallogr D Biol Crystallogr 60, 2256-2268.

Lu, et al. (2001). Association of the membrane-proximal regions of the a and b subunit cytoplasmic domains constrains an integrin in the inactive state. The Journal of biological chemistry 276, 14642-14648.

Lub, et al. (1997). Cytoplasmic tails of b1, b2, and b7 integrins differentially regulate LFA-1 function in K562 cells. Mol. Biol. Cell 8, 719-728.

Luo, et al. (2007). Structural basis of integrin regulation and signaling. Annu. Rev. Imm. 25, 619-647.

Luo, et al. (2003). High affinity ligand binding by integrins does not involve head separation. The Journal of biological chemistry 278, 17185-17189.

Luo, et al. (2004). A specific interface between integrin transmembrane helices and affinity for ligand. PLoS Biol. 2, 776-786.

Ma, et al. (2008). Kindlin-2 (Mig-2): a co-activator of beta3 integrins. The Journal of cell biology 181, 439-446.

Marlin, et al. (1987). Purified intercellular adhesion molecule-1 (ICAM-1) is a ligand for lymphocyte function-associated antigen 1 (LFA-1). Cell 51, 813-819.

Miyamoto, et al. (1995). Synergistic roles for receptor occupancy and aggregation in integrin transmembrane function. Science, 267, 883-885.

Montanez, et al. (2008). Kindlin-2 controls bidirectional signaling of integrins. Genes Dev 22, 1325-1330.

Moser, et al. (2008). Kindlin-3 is essential for integrin activation and platelet aggregation. Nature medicine 14, 325-330.

Mould, et al. (2003). Role of ADMIDAS cation-binding site in ligand recognition by integrin a5b1. The Journal of biological chemistry 278, 51622-51629.

Nishida, et al. (2006). Activation of leukocyte b2 integrins by conversion from bent to extended conformations. Immunity 25, 583-594.

Phillips, et al. (2005). Scalable molecular dynamics with NAMD. Journal of computational chemistry 26, 1781-1802.

Puklin-Faucher, et al. (2006). How the headpiece hinge angle is opened: New insights into the dynamics of integrin activation. J. Cell Biol. 175, 349-360.

Rocco, et al. (2008). Integrin conformational regulation: uncoupling extension/tail separation from changes in the head region by a multiresolution approach. Structure 16, 954-964.

Sheetz, M.P. (1993). Glycoprotein motility and dynamic domains in fluid plasma membranes. Annual review of biophysics and biomolecular structure 22, 417-431.

Shi, et al. (2007). A structural hypothesis for the transition between bent and extended conformations of the leukocyte b2 integrins. The Journal of biological chemistry, 287(41), 30198-30206.

Shi, et al. (2005). The crystal structure of the plexin-semaphorin-integrin domain/hybrid domain/I-EGF1 segment from the human integrin b2 subunit at 1.8-A resolution. The Journal of biological chemistry 280, 30586-30593.

Springer, et al. (2008). Structural basis for distinctive recognition of fibrinogen by the platelet integrin aIIbb3. J. Cell Biol., 182 (4), 791-800.

Tadokoro, et al. (2003). Talin binding to integrin b tails: a final common step in integrin activation. Science, 302, 103-106.

Takagi, et al. (2001). Definition of EGF-like, closely interacting modules that bear activation epitopes in integrin b subunits. Proc. Natl. Acad. Sci. U. S. A. 98, 11175-11180.

Takagi, et al. (2002). Global conformational rearrangements in integrin extracellular domains in outside-in and inside-out signaling. Cell 110, 599-611.

Tan, et al. (2001). Defining the repeating elements in the cysteine-rich region (CRR) of the CD18 integrin b2 subunit. FEBS Lett. 505, 27-30.

Varma, et al. (2006). T cell receptor-proximal signals are sustained in peripheral microclusters and terminated in the central supramolecular activation cluster. Immunity 25, 117-127.

Verschueren, H. (1985). Interference reflection microscopy in cell biology: Methodology and applications. J.Cell.Sci. 75, 279-301.

Wegener, et al. (2008). Transmembrane and cytoplasmic domains in integrin activation and protein-protein interactions (Review). Molecular Membrane Biology 25, 376-387.

Xiao, et al. (2004). Structural basis for allostery in integrins and binding of fibrinogen-mimetic therapeutics. Nature 432, 59-67.

Xiong, et al. (2001). Crystal structure of the extracellular segment of integrin aVb3. Science, 294, 339-345.

Xiong, et al (2004). A novel adaptation of the integrin PSI domain revealed from its crystal structure. The Journal of biological chemistry 279, 40252-40254.

\* cited by examiner

| TRANSFECTION | α SUBUNIT | β SUBUNIT | EXPRESSION ON CELL SURFACE (MFI) | CROSSLINKING |
|---|---|---|---|---|
| CONTROL | WILD TYPE | WILD TYPE | 152.62 | - |
| #1 | E1061C | E672C | NO EXPRESSION | ND |
| #2 | E1061C | G676C | 91.04 | + |
| #3 | K1062C | G676C | 110.79 | + |
| #4 | Q1063C | G676C | 89.56 | + |
| #5 | K1062C | P677C | 95.84 | + |
| #6 | Q1063C | P677C | 110.53 | + |
| #7 | M1064C | P677C | 119.52 | + |
| #8 | Q1063C | N678C | 82.12 | + |
| #9 | M1064C | N678C | 140.78 | + |

FIG. 6A

| SOLUBLE INTEGRIN TRANSFECTION | α SUBUNIT | β SUBUNIT | CROSSLINKING |
|---|---|---|---|
| WILDTYPE αLβ2 (αLβ2-TCHS) | αL-TAS | β2-TBH | - |
| | αL$^{E1051C}$-TAS | β2$^{V674C}$-TBH | ND* |
| | αL$^{E1051C}$-TAS | β2$^{G576C}$-TBH | ND* |
| αLβ2-Clasp-TCHS | αL$^{E1051C}$-TAS | β2-GCG-TBH | + |
| | αL-GCG-TAS | β2$^{V674C}$-TBH | ND* |
| | αL-GCG-TAS | β2$^{G576C}$-TBH | ND* |
| αLβ2-GCG-TCHS | αL-GCG-TAS | β2-GCG-TBH | + |
| WILDTYPE αXβ2 (αXβ2-TCHS) | αX-TAS | β2-TBH | - |
| αXβ2-GCG-TCHS | αX-GCG-TAS | β2-GCG-TBH | + |

ND*: THE DISULFIDE-BOND FORMING IS UNDETECTABLE DUE TO THE LOW EXPRESSION LEVEL.

*FIG. 6B*

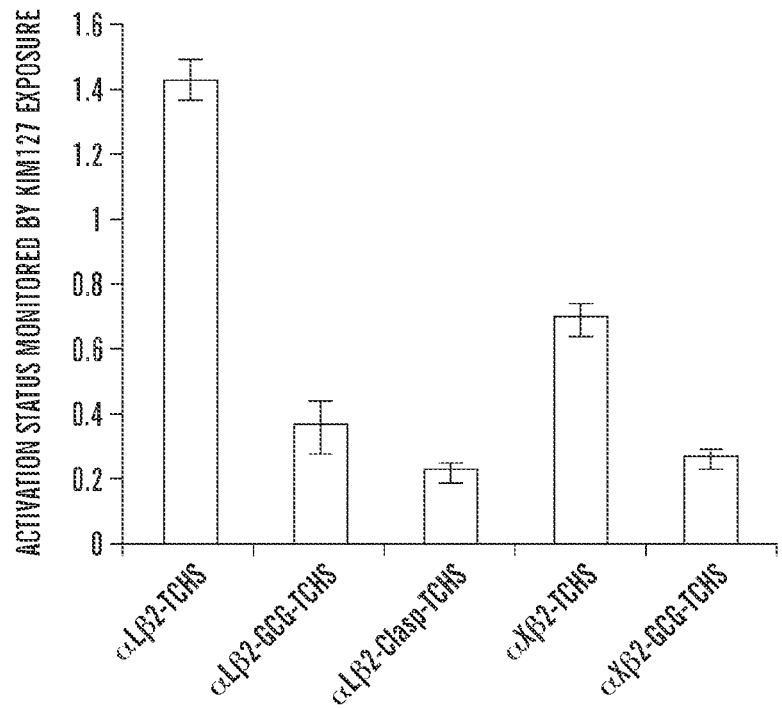

STABILIZED LOW AFFINITY CONFORMATION OF INTEGRINS FOR DRUG DISCOVERY

CROSS REFERENCE TO RELATED APPLICATIONS

This application claims the benefit under 35 U.S.C. §119 (e) of U.S. Provisional Application No. 61/141,145 filed on Dec. 29, 2008, the contents of which are incorporated herein by reference in its entirety.

SEQUENCE LISTING

The instant application contains a Sequence Listing which has been submitted via EFS-Web as an ASCII copy and is hereby incorporated by reference in its entirety. Said ASCII copy, created on Jan. 12, 2010, is named 03339306.txt, and is 170,131 bytes in size.

FIELD OF THE INVENTION

The field of the invention relates to stabilized integrins and uses thereof.

BACKGROUND

Integrins are cell adhesion receptors that transmit bidirectional signals across the plasma membrane and link the extracellular environment of a cell to the actin cytoskeleton. The conformation of the integrin extracellular domain and its affinity for ligand are dynamically regulated by a process termed "inside-out signaling." Rapid upregulation of adhesiveness of integrins on platelets and white blood cells mediates hemostasis and leukocyte trafficking to sites of inflammation. By coupling to the actin cytoskeleton, integrins promote firm adhesion and provide traction for lamellipodium protrusion and locomotion. In migrating cells the adhesiveness of integrins is spatially and temporally regulated so that integrins are activated near the leading edge to support lamellipod extension and deactivated near the trailing edge to support uropod retraction and internalization (Alon and Dustin, 2007; Arnaout et al., 2005; Broussard et al., 2008; Calderwood, 2004; Evans and Calderwood, 2007; Luo et al., 2007).

Integrin $\alpha_{IIb}\beta_3$, the most abundant receptor on platelets, binds to fibrinogen and von Willebrand factor, and mediates platelet aggregation and association with injured vessel walls. Inherited mutations in its $\alpha_{IIb}$ or $\beta_3$ subunits result in the bleeding disorder Glanzmann's thrombasthenia. RGD-mimetic small molecules and an antibody to $\alpha_{IIb}\beta_3$ are prescribed for the prevention of thrombosis ((Springer et al., 2008; Xiao et al., 2004).

The integrin $\alpha$ and $\beta$ subunits have large N-terminal extracellular domains, single-pass transmembrane domains, and usually short C-terminal cytoplasmic domains. The first crystal structure of an integrin ectodomain, of $\alpha_V\beta_3$, represented a huge advance (Xiong et al., 2001; Xiong et al., 2002). Together with subsequent work, ten of twelve domains in the ectofragment were revealed in a bent conformation (Xiao et al., 2004; Xiong et al., 2004). A ligand-binding head formed by both subunits is followed by legs in each subunit that connect to the transmembrane domains. There is an extreme bend at knees between the upper and lower legs. Integrin epidermal growth factor-like (I-EGF) domains 1 and 2 at the $\beta$-knee were disordered in the previous $\alpha_V\beta_3$ structure. Crystals of $\beta_2$ leg fragments containing I-EGF domains 1 and 2 have been solved in two different orientations (Shi et al., 2007), but the conformation of these domains in the bent integrin conformation remains unknown.

Subsequent to the $\alpha_V\beta_3$ crystal structure, mutational studies on cell surface integrins and EM studies on $\alpha_V\beta_3$, $\alpha_L\beta_2$, and $\alpha_X\beta_2$ integrins demonstrated that the bent conformation is the physiologically relevant, low affinity integrin conformation (Nishida et al., 2006; Takagi et al., 2002). Nonetheless, a cryo EM study on $\alpha_{IIb}\beta_3$ revealed a different, less compact conformation with a different arrangement of leg domains (Adair and Yeager, 2002). Furthermore, two recent studies have revealed extended conformations of $\alpha_{IIb}\beta_3$ but failed to find a bent conformation (Rocco et al., 2008; Ye et al., 2008). Crystal structure studies on $\alpha_{IIb}\beta_3$ are important to resolve these controversies. Revealing the structure within a complete ectodomain of the bent $\beta$-knee is important to understanding the mechanism of integrin extension. Moreover, no integrin crystal structure to date has described the bent structure in the light of current knowledge that it is physiologically relevant, is in a low-affinity state, and with the aim of understanding how the bent conformation is stabilized and how it transitions to extended conformations. The previous $\alpha_V\beta_3$ bent conformation was described as "not expected to occur in the membrane-bound receptor," and being in "its active (ligand competent) state" (Xiong et al., 2001).

Most studies find that upon activation, integrins extend. Upon extension, the headpiece can remain in the closed conformation, as when bent, or transition to an open conformation with high affinity for ligand (Xiao et al., 2004). In contrast, a "deadbolt model" posits that activation can occur in the absence of extension (Arnaout et al., 2005). Binding of cytoskeletal proteins such as talin and kindlins to the integrin $\beta$ cytoplasmic domain appears to interfere with $\alpha/\beta$ cytoplasmic domain association, and induce integrin extension (Wegener and Campbell, 2008). However, there is currently no known feature of integrin structure that would enable cytoskeleton binding to couple to the extended, open conformation with high affinity for ligand. This would appear to be important to fulfill the key role of integrins in integrating the extracellular and intracellular environments.

Three closely linked metal ion binding sites in the $\beta$ I domain are especially important in ligand binding. Mg2+ at the central, metal ion-dependent adhesion site (MIDAS) site directly coordinates the acidic sidechain shared by all integrin ligands. However, in previous unliganded, bent $\alpha_V\beta_3$ structures, the MIDAS and one adjacent site were unoccupied, and it was proposed that metal binding was either caused by integrin activation or induced by ligand binding (Xiong et al., 2002) However, crystals have not been reported with a combination of the two metal ions important for integrin ligand binding, Mg2+ and Ca2+. Therefore, in current comparisons between low and high affinity $\beta$ I domain conformations, the changes associated with ligand binding and metal binding cannot be deconvoluted.

SUMMARY OF THE CLAIMS

The methods described herein are based in part on the discovery that a disulfide bond can be introduced to an integrin polypeptide by the substitution of at least one cysteine residue in the polypeptide. The disulfide bond(s) formed in the integrin polypeptide stabilize the integrin in a "closed/inactive" state, which permits the integrins to be screened for a candidate molecule that can bind to the closed state. In particular, this approach can be used to screen for agents that bind to the closed state of an integrin polypeptide, and would be useful as therapeutic treatments to prevent integrin activation.

In one aspect, the methods described herein relate to a method of identifying a candidate modulator of integrin activity, comprising (a) contacting an integrin polypeptide with a candidate agent, wherein the integrin polypeptide is locked into a desired conformation; and (b) detecting binding of the candidate agent to the integrin polypeptide, wherein binding of the candidate agent to the integrin polypeptide is indicative that the candidate agent is a candidate modulator of integrin activity.

In one embodiment of this aspect and all other aspects described herein, The method of the candidate agent is selected from the group consisting of an antibody, a small molecule, a chemical, a peptide, and a peptidomimetic.

In another embodiment of this aspect and all other aspects described herein, the candidate modulator stabilizes the integrin polypeptide into a closed conformation. Alternatively, the candidate modulator can induce a conformational shift from the open conformation to the closed conformation.

In another embodiment of this aspect and all other aspects described herein, the candidate modulator inhibits binding of an integrin ligand to the integrin polypeptide. Alternatively, the candidate modulator may act at a site distant from the integrin ligand site to prevent integrin-mediated activity in response to ligand binding—that is, ligand binding may occur but activation of the integrin activity is blocked (e.g., non-competitive inhibition).

In another embodiment of this aspect and all other aspects described herein, the integrin polypeptide is selected from the group consisting of $\alpha_V\beta_3$, $\alpha_{II}b\beta_3$, $\alpha_V b_6$, $\alpha_V\beta_1$, $\alpha_V\beta_5$, $\alpha_M\beta_2$, $\alpha_X\beta_2$, $\alpha_L\beta_2$, and $\alpha_V\beta_8$.

In another embodiment of this aspect and all other aspects described herein, wherein locking the integrin polypeptide into the desired conformation comprises introducing a stabilizing disulfide bond into the integrin polypeptide.

In another embodiment of this aspect and all other aspects described herein, the disulfide bond is formed by a cysteine residue substitution of at least one amino acid residue of said integrin polypeptide.

In another embodiment of this aspect and all other aspects described herein, the substitution comprises a mutation selected from the group consisting of: L959C (human αIIb), E960C (human αIIb), 1955C (human $\alpha_V$), Q956C (human $\alpha_V$), V664C (human $\beta_3$), P688C (human $\beta_3$), L662C (human $\beta_6$), P686C (human $\beta_6$), A619C (human $\beta_8$), and F636C (human $\beta_3$).

In another embodiment of this aspect and all other aspects described herein, the candidate agent is further assayed for activation or inhibition of integrin activity. In one embodiment, a cell-based assay is used to determine integrin activity.

Another aspect described herein is an integrin polypeptide composition stabilized in the "closed" conformation. In one embodiment, the integrin polypeptide is stabilized by substitution of at least one amino acid residue for a cysteine residue, wherein a disulfide bond is formed.

In another embodiment of this aspect and all other aspects described herein, the substitution comprises a mutation selected from the group consisting of: L959C (human αIIb), E960C (human αIIb), 1955C (human $\alpha_V$), Q956C (human $\alpha_V$), V664C (human $\beta_3$), P688C (human $\beta_3$), L662C (human $\beta_6$), P686C (human $\beta_6$), A619C (human $\beta_8$), and F636C (human $\beta_3$).

In another embodiment of this aspect, the composition further comprises a solid support such as a bead, a dish, a well, a plate, etc.

DEFINITIONS

As used herein, a "modified integrin I-domain polypeptide" or "modified integrin polypeptide" includes an integrin I-domain polypeptide that has been altered with respect to the wild-type sequence or the native state such that at least one disulfide bond has been introduced into the polypeptide thereby stabilizing the integrin in a desired conformation. An integrin polypeptide is considered "locked into a desired conformation" if the disulfide bond prevents a conformational shift in the integrin polypeptide from occurring under non-denaturing conditions (i.e., denaturing conditions can be induced by e.g., high temperatures, the presence of reducing agents (such as β-mercaptoethanol, dithiothreitol), the presence of strong denaturing reagents (such as 6M guanidinium hydrochloride, 8M urea, or 1% sodium dodecyl sulfate), or any combination thereof).

As used herein, the term "stabilizing disulfide bond" is used to describe substitution of at least one cysteine residue that permits the formation of a disulfide bond, which in turn prevents a conformational shift in the integrin polypeptide even in the presence of an activating ligand. The "stabilizing disulfide bond" is introduced to the polypeptide by one of skill in the art and does not reflect a natural or native disulfide bond of the polypeptide. However, it is contemplated that an integrin polypeptide with such a stabilizing disulfide bond can be found in nature due to a mutation in amino acid sequence.

As used herein, the term "binding of the candidate agent" refers to an interaction of a candidate agent with an integrin polypeptide stabilized in a closed conformation. Since the conformation of the integrin polypeptide is held in place by a disulfide bond, the term "binding" reflects an interaction and is insufficient to indicate the inhibitory or activating activity of the compound. Further screening assays for integrin activity, as described herein, should be used to determine the action of a candidate agent.

As used herein, the term "candidate agent" includes a compound or other agent that is capable of at least binding to an integrin polypeptide or modified polypeptide as described herein. In an alternative embodiment, the compound or agent is "a modulator of integrin activity," which is capable of modulating or regulating at least one integrin activity, as described herein. Modulators of integrin activity may include, but are not limited to, small organic or inorganic molecules, nucleic acid molecules, peptides, antibodies, and the like. A modulator of integrin activity can be an inducer or inhibitor of integrin-mediated activities such as cell adhesion or ligand binding. As used herein, an "inducer of integrin activity" stimulates, enhances, and/or mimics an integrin activity. As used herein, an "inhibitor of integrin activity" reduces, blocks or antagonizes an integrin activity.

As used interchangeably herein, the terms "integrin activity", or "integrin-mediated activity" refer to an activity exerted by an integrin polypeptide or nucleic acid molecule on an integrin responsive cell, or on integrin ligand or receptor, as determined in vitro and in vivo, according to standard techniques. In one embodiment, an integrin activity is the ability to mediate cell adhesion events, e.g., cell to cell, or cell to extracellular matrix adhesion. In another embodiment, an integrin activity can be measured as the ability to transduce cellular signaling events. In yet another embodiment, an integrin activity is the ability to bind a ligand, e.g., ICAM.

As used herein, the term "inhibition of integrin activity" refers to a decrease in ligand activated integrin activity of at least 10% as assessed using a cell-based integrin assay; preferably the activity of the integrin is decreased by at least 20%, at least 30%, at least 40%, at least 50%, at least 60%, at least 70%, at least 80%, at least 90%, at least 95%, at least 99%, or even 100% (i.e., no activity) integrin activity in the same cell-based integrin assay.

As used herein, the term "inhibition of integrin activity" refers to a decrease in ligand activated integrin activity of at least 10% as assessed using a cell-based integrin assay; preferably the activity of the integrin is decreased by at least 20%, at least 30%, at least 40%, at least 50%, at least 60%, at least 70%, at least 80%, at least 90%, at least 95%, at least 99%, or even 100% (i.e., no activity) integrin activity in the same cell-based integrin assay.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

BRIEF DESCRIPTION OF THE FIGURES

FIG 5A. Sequences around the cysteine mutations are shown (SEQ ID NOS 85-94, respectively, in order of appearance). Cysteine mutations were introduced and are shown, and the names of each exemplary construct are labeled at the right. FIG. 5B. Expression of the tested α/β combinations was tested using a FACS assay to identify cell surface expression. Disulfide bond formation was detected by Western blotting of lysed cell after transfection. FIG. 5C. A schematic representation of the α/β combinations tested and shown in FIG. 2B (SEQ ID NOS 104 and 81, respectively, in order of appearance).

FIGS. 6A-6C show soluble integrin $\alpha_L\beta_2$ (LFA-1) and $\alpha_X\beta_2$ (CR4) crosslinking and activation. FIG. 6A. C-terminal sequence of constructs used for soluble integrin expression (SEQ ID NOS 95-103, respectively, in order of appearance). The cysteine mutations were introduced and are shown. The name of each construct is depicted at the right of each sequence. Tags and other features are labeled above the sequences. His6 tag disclosed as SEQ ID No: 105. FIG. 6B. Exemplary α/β combinations were tested in transfection and protein purification experiments. Crosslinking was confirmed by SDS-PAGE after protein purification and TEV cleavage. FIG 6C. Activation status of purified integrin proteins was monitored by KIM127 exposure in 1 mM $Ca^{2+}$/$Mg^{2+}$.

Figure 7A:
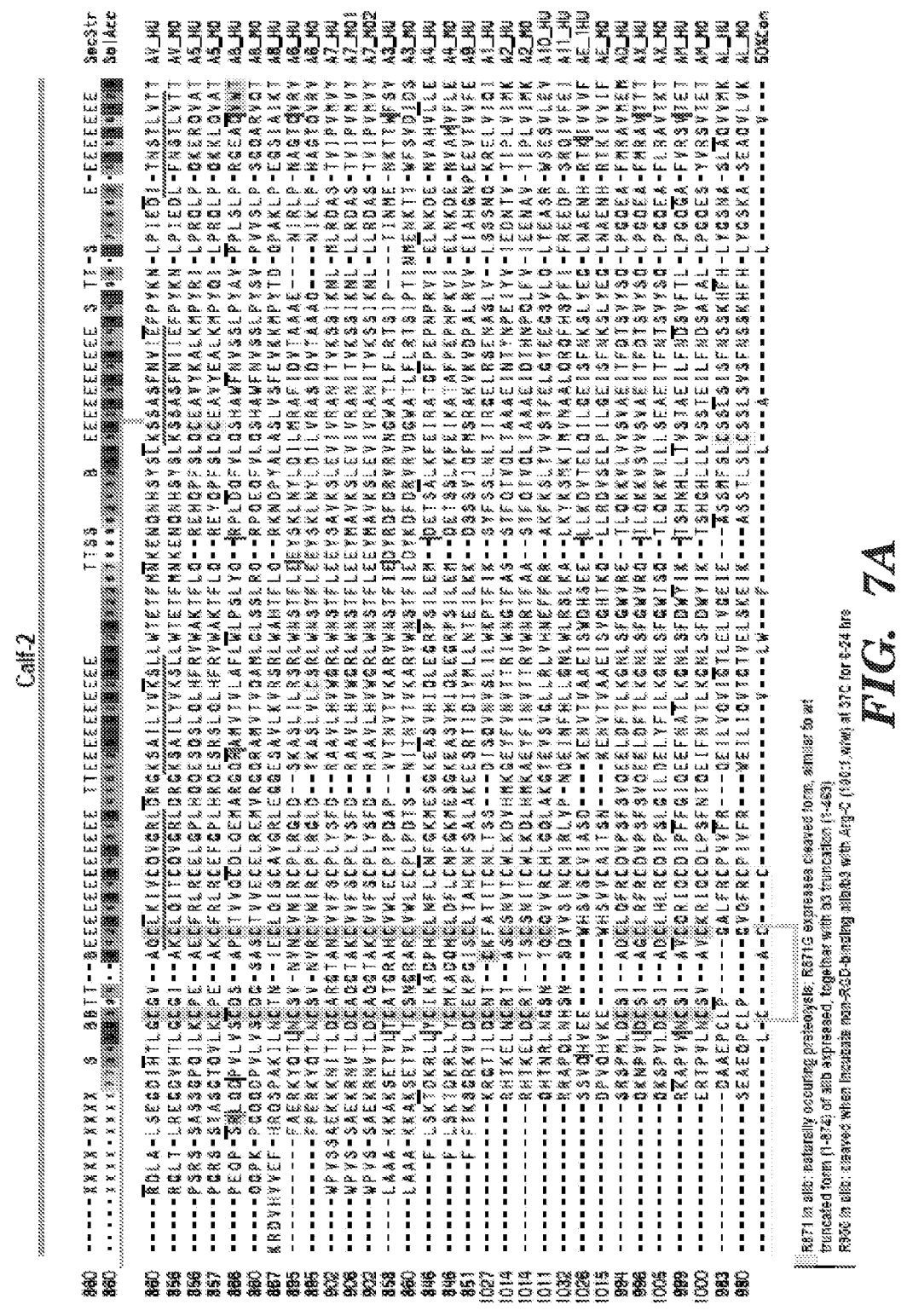
Figure 7B:
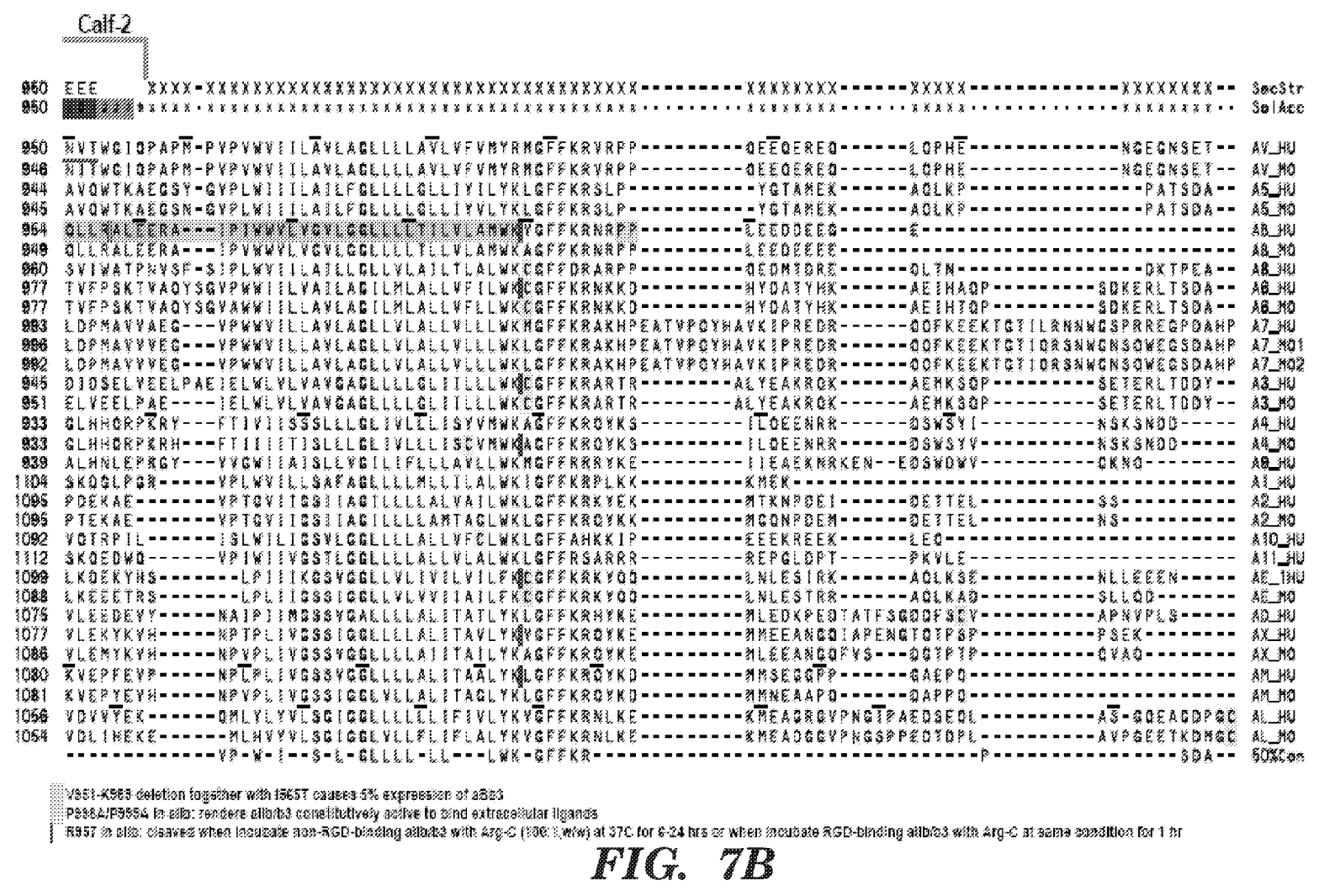
Figure 7C:
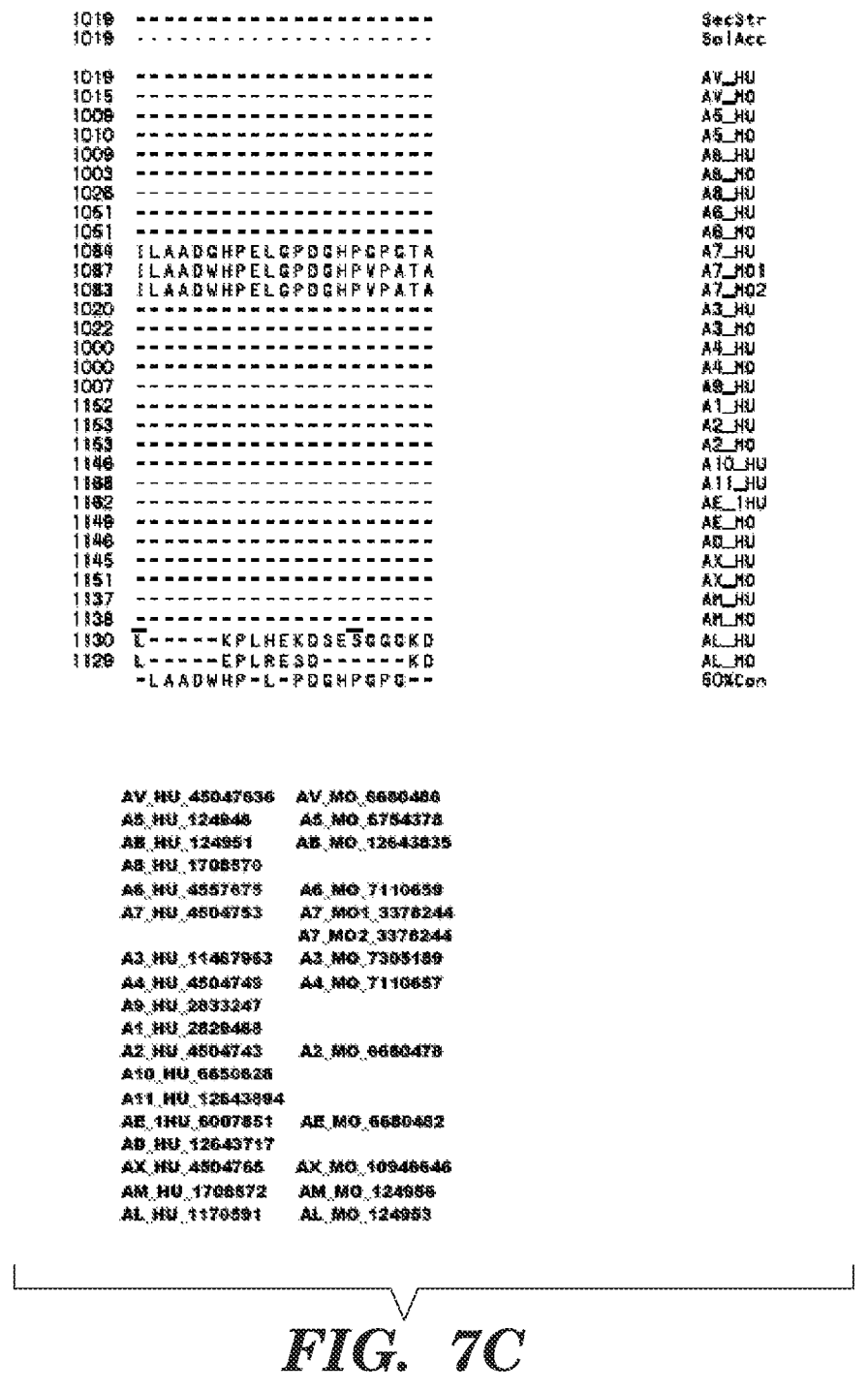

FIG. 7 shows optimal sequence alignments of exemplary integrin alpha subunits. FIG. 7 includes a sequence alignment of AV_HU_4504763 (SEQ ID NO: 1), AV_MO_6680486 (SEQ ID NO: 2), A5_HU_124946 (SEQ ID NO: 3), A5_MO_6754378 (SEQ ID NO:4), AB_HU_124951 (SEQ ID NO: 5), AB_MO_12643835 (SEQ ID NO: 6), A8_HU_1708570 (SEQ ID NO: 7), A6_HU_4557675 (SEQ ID NO: 8), A6_MO_7110659 (SEQ ID NO: 9), A7_HU_4504753 (SEQ ID NO: 10), A7_MO1_3378244 (SEQ ID NO: 11), A7_MO2_3378244 (SEQ ID NO: 12), A3_HU-11467963 (SEQ ID NO: 13), A3_MO_7305189 (SEQ ID NO: 14), A4_HU_4504749 (SEQ ID NO: 15), A4_MO_7110657 (SEQ ID NO: 16), A9_HU_2833247 (SEQ ID NO: 17), A1_HU_2829468 (SEQ ID NO: 18), A2_HU_4504743 (SEQ ID NO: 19), A2_MO_6680478 (SEQ ID NO: 20), A10_HU_6650628 (SEQ ID NO: 21), A11_HU_12643894 (SEQ ID NO: 22), AE_1HU_6007851 (SEQ ID NO: 23), AE_MO_6680482 (SEQ ID NO: 24), AD_HU_12643717 (SEQ ID NO: 25), AX_HU_4504765 (SEQ ID NO: 26), AX_MO_10946646 (SEQ ID NO: 27), AM_HU_1708572 (SEQ ID NO: 28), AM_MO_124956 (SEQ ID NO: 29), AL_HU_1170591 (SEQ ID NO: 30), and AL_MO_124953 (SEQ ID NO: 31).

Figure 8B:
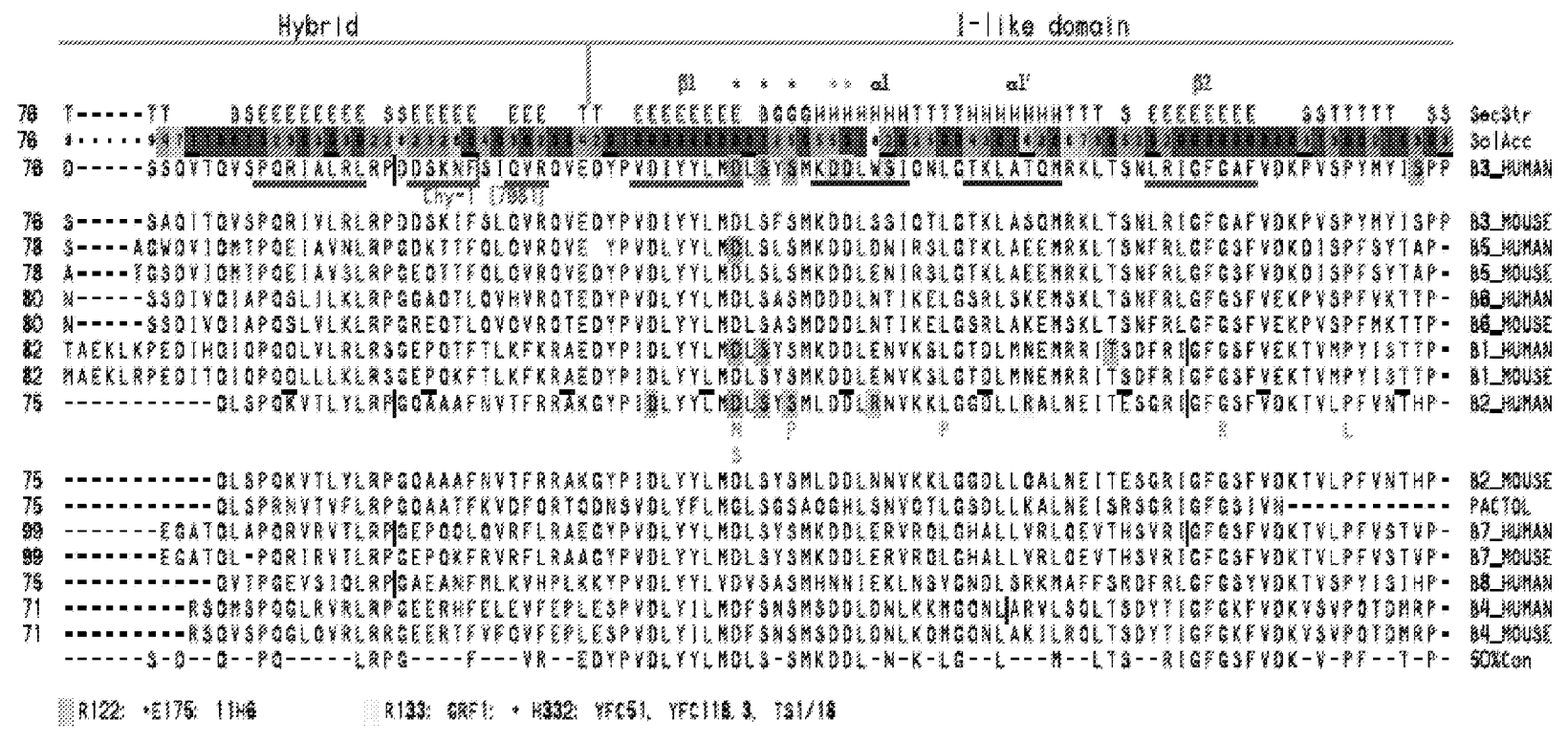
Figure 8C:
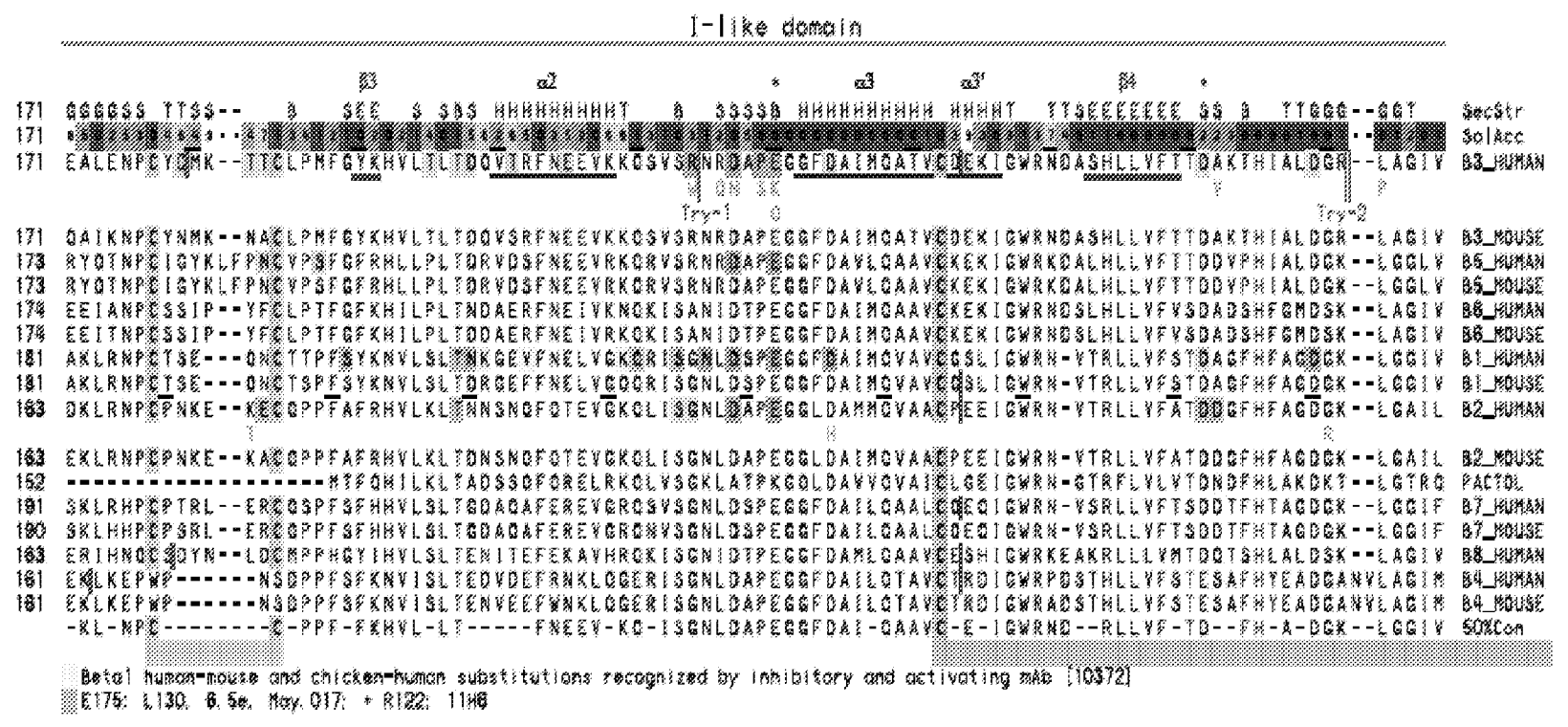
Figure 8D:
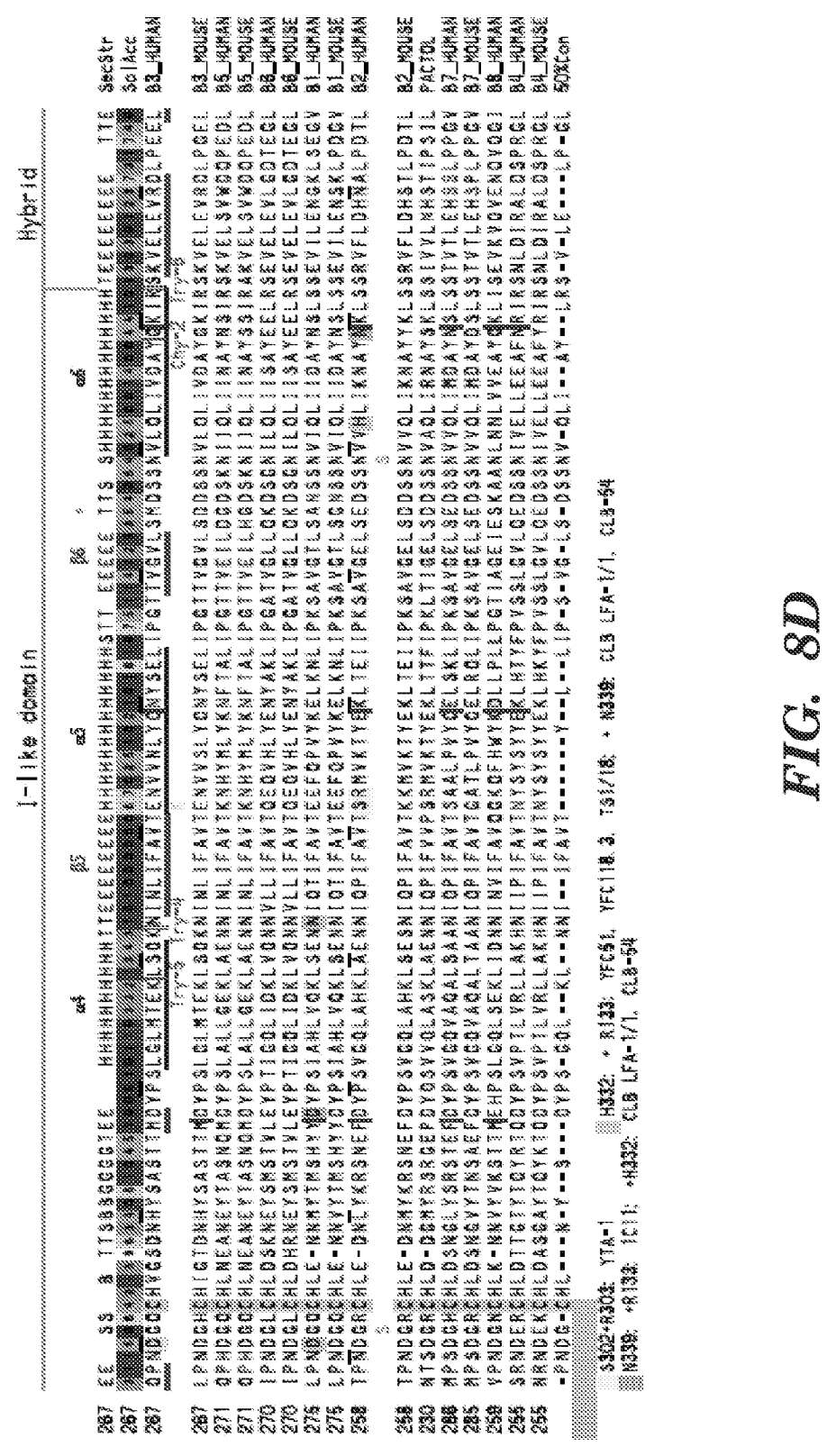
Figure 8E:
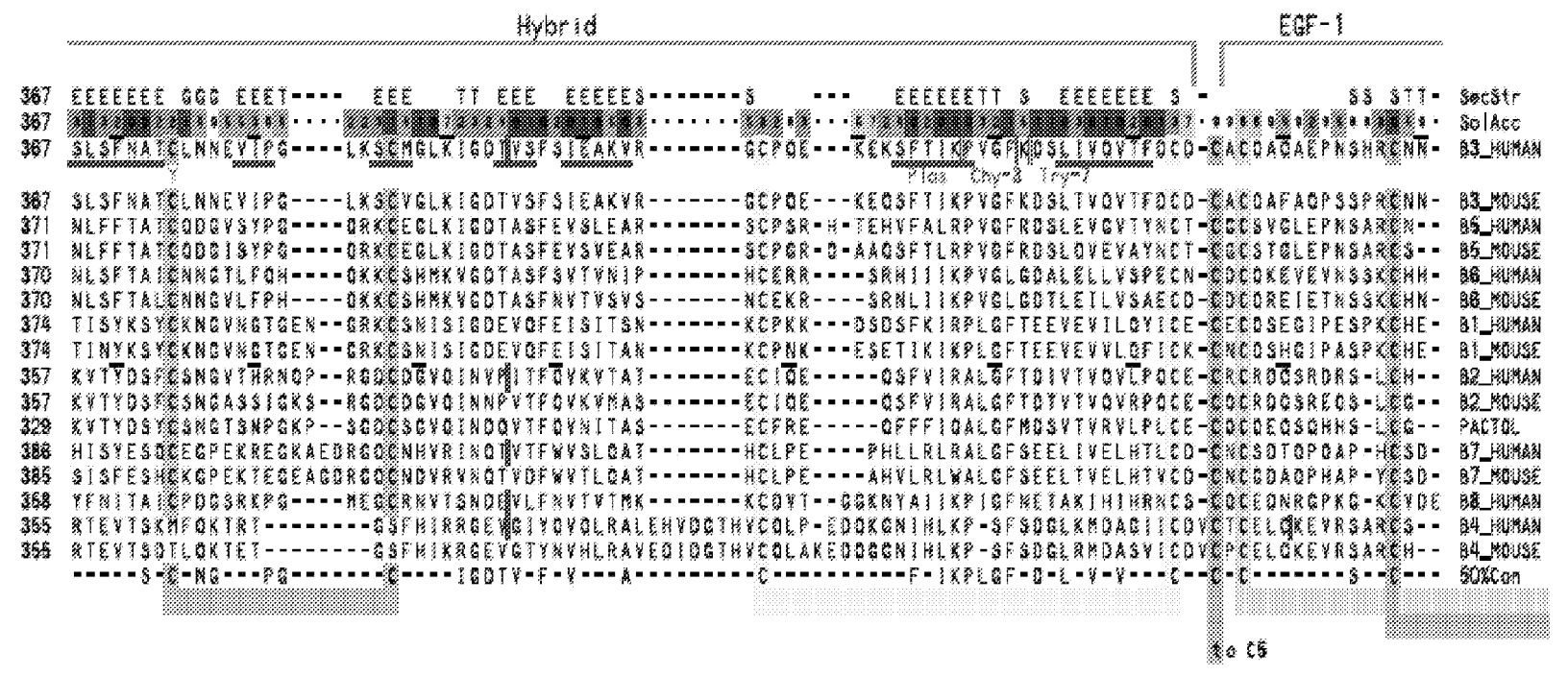
Figure 8F:
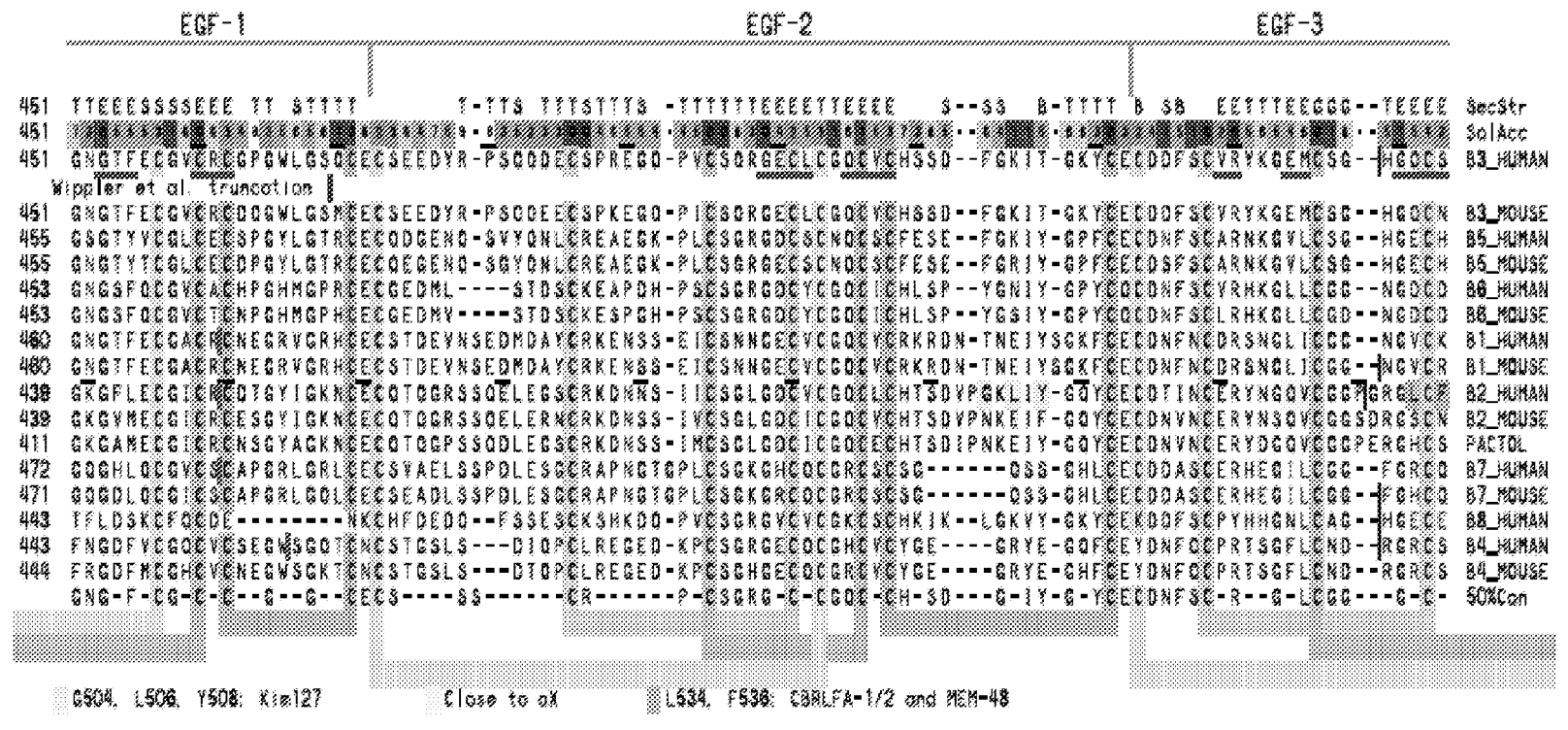
Figure 8G:
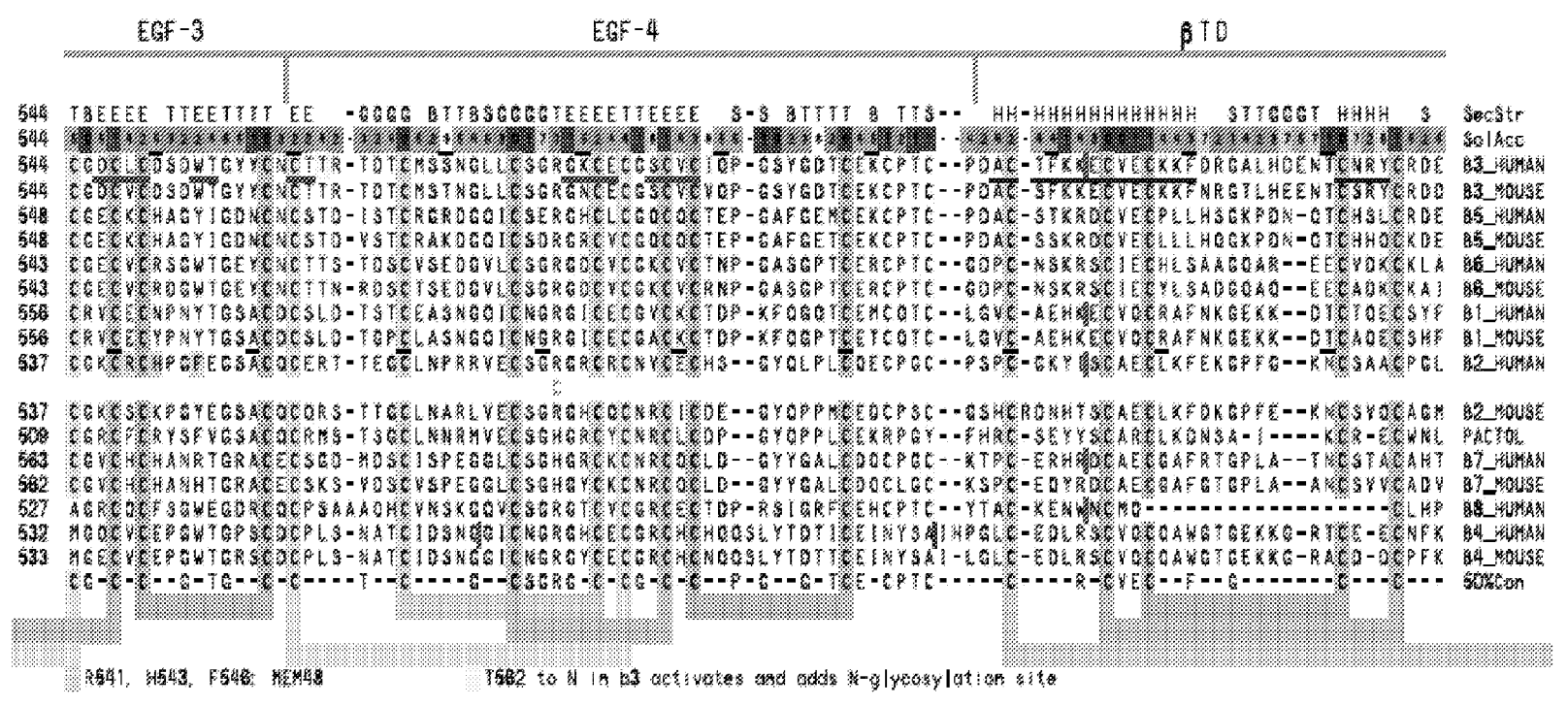
Figure 8H:
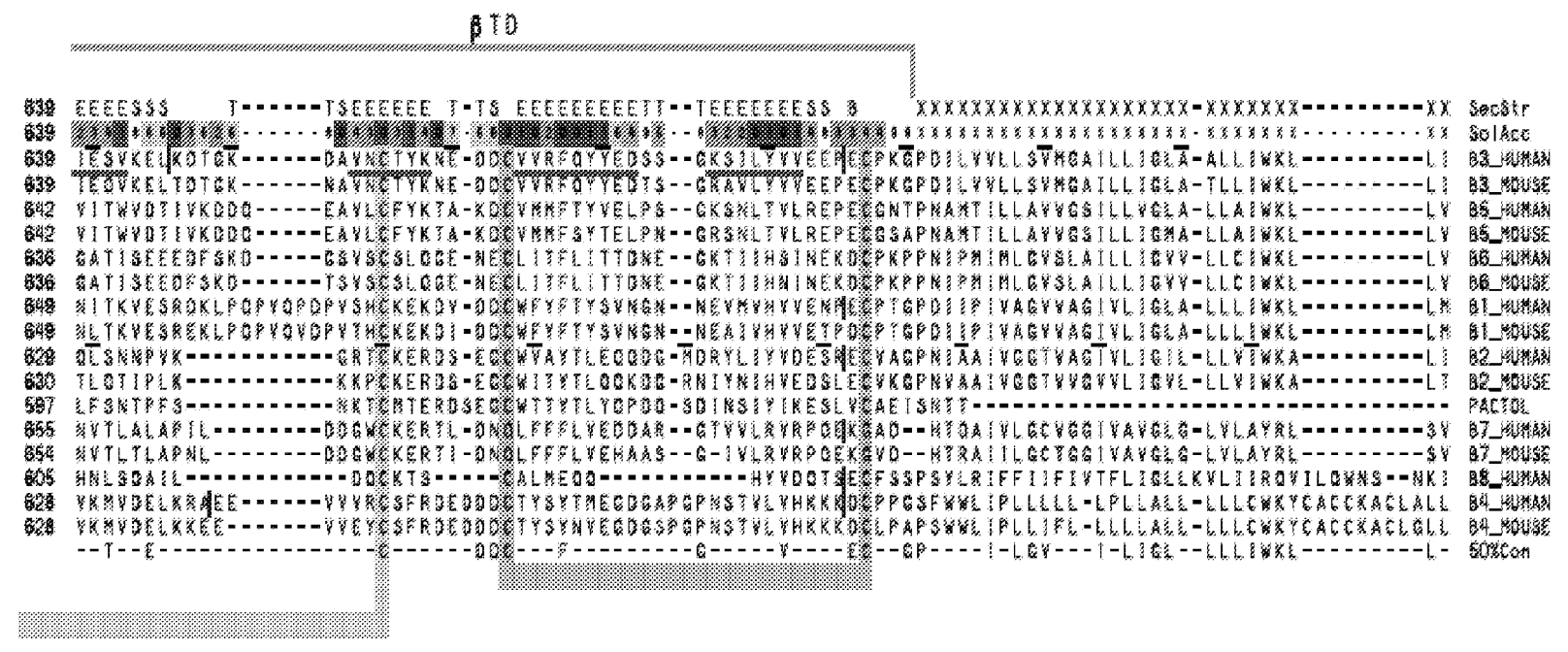
Figure 8I:
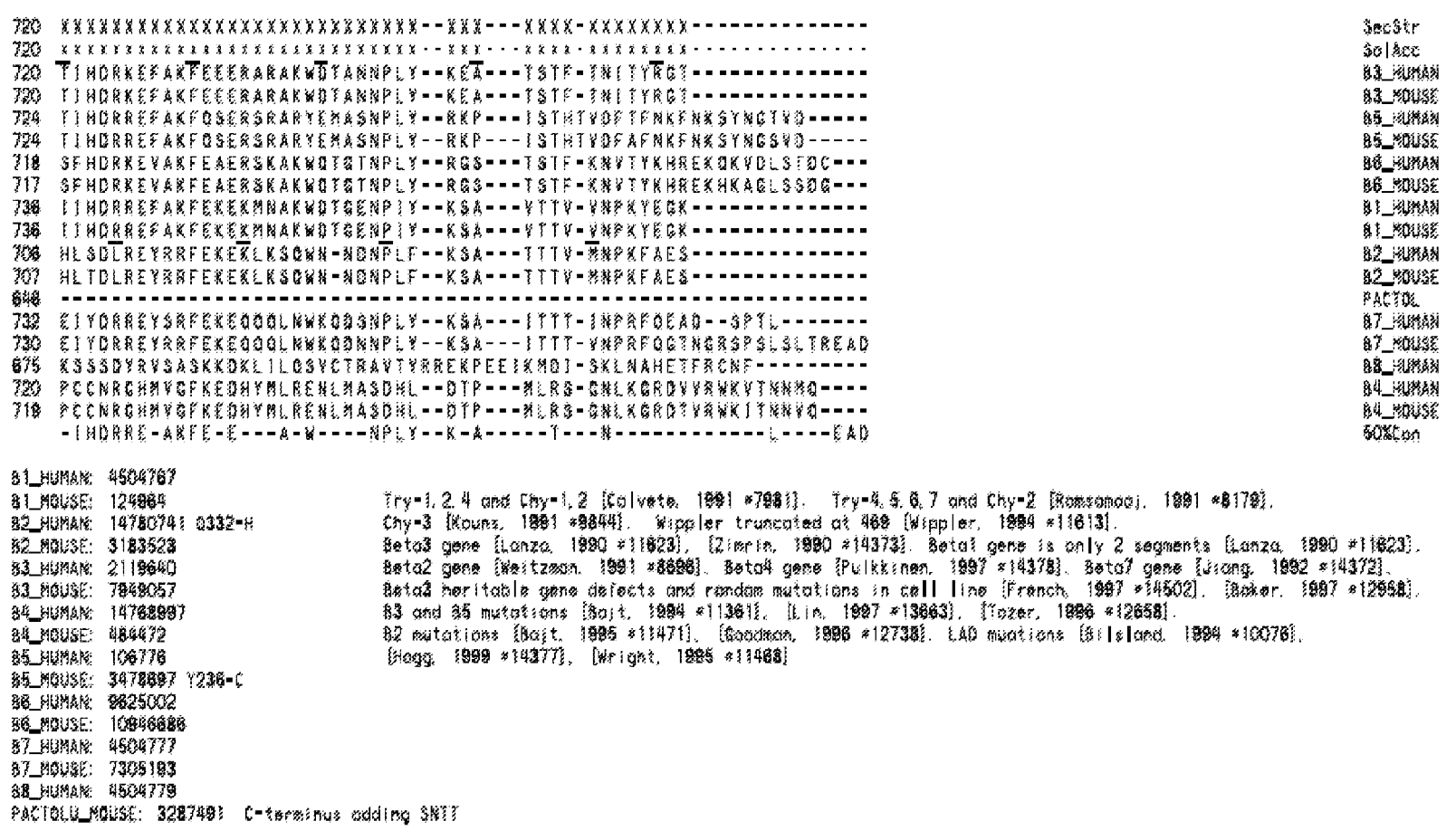

FIG. 8 includes a sequence alignment of sequences B1_HUMAN_4504767 (SEQ ID NO: 32), B1_MOUSE_124964 (SEQ ID NO: 33), B2_HUMAN_147807410332-H (SEQ ID NO: 34), B2_MOUSE_3183523 (SEQ ID NO: 35), B3_HUMAN_2119640 (SEQ ID NO: 36), B3_MOUSE_7949057 (SEQ ID NO: 37), B4_HUMAN_14768997 (SEQ ID NO: 38), B4_MOUSE_484-472 (SEQ ID NO: 39), B5_HUMAN_106776 (SEQ ID NO: 40), B5_MOUSE_3478697 y236-C (SEQ ID NO: 41), B6_HUMAN_9625002 (SEQ ID NO: 42), B6_MOUSE_10946686 (SEQ ID NO: 43), B7_HUMAN_4504777 (SEQ ID NO: 44), B7_MOUSE_7305193 (SEQ ID NO: 45), B8_HUMAN_4504779 (SEQ ID NO: 46), and PACTOLU_MOUSE_3287491 (SEQ ID NO: 47). "SNTT"disclosed as residues 646-649 of SEQ ID NO: 47.

DETAILED DESCRIPTION

Figure 1A:
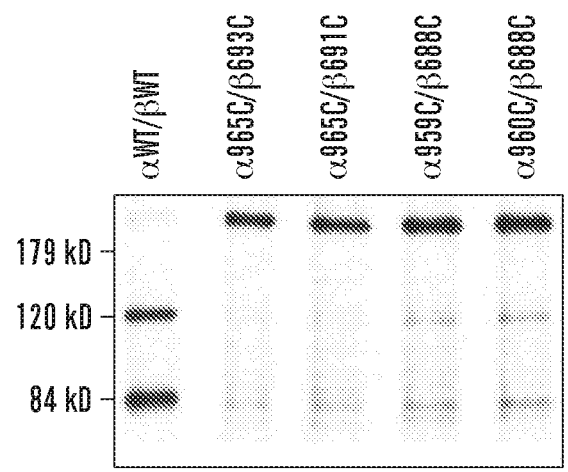
FIG. 1 shows disulfide bond formation in mutant receptors and effect on function. 293T cells were co-transfected with full-length, wild-type or mutant integrin subunits to express the indicated α/β pairs on the cell surface. A. Integrin heterodimers were immunoprecipitated from $^{35}$S-labeled cell detergent lysates with anti-$\beta_3$ mAb AP3 and subjected to non-reducing SDS-PAGE and fluorography. Molecular size markers are shown on the left. B. Soluble fibrinogen binding to 293T transfectants in the presence of 1 mM $Ca^{2+}$/1 mM $Mg^{2+}$ (white) or 1 mM $Mn^{2+}$ plus 10 mg/ml PT25-2 antibody (black). Binding was measured as the mean fluorescence intensity of FITC-conjugated fibrinogen staining as a percentage of mean fluorescence intensity of staining with Cy3-conjugated AP3 mAb. Methods were as described previously (Luo, et al. 2004; Zhu, et al. 2007).

The methods described herein are based in part on the discovery that the introduction of a disulfide bond into an integrin polypeptide by the substitution of at least one cysteine residue in the polypeptide permits stabilization of the integrin in a "closed/inactive" state. This stabilizing disulfide bond permits integrins to be screened for a candidate molecule that can bind to the closed state. In particular, this approach can be used to screen for agents that bind to the closed state of an integrin polypeptide, and would be useful as therapeutic treatments to prevent integrin activation.

The α$_{IIb}$β$_3$ crystal structure. A crystal structure for molecule I in α$_{IIb}$β$_3$ crystals was determined and ribbon diagrams were prepared (data not shown). The following characteristics are noted. In one model, the α$_{IIb}$β$_3$ is extended by torsion at the α and β-knees. Upon supersition of molecules 1 and 2 of α$_{IIb}$β$_3$ and α$_v$β$_3$ (Xiong et al., 2004) the structures indicate "breathing". It is determined that there is a variation in the distance of the lower α-leg from the lower β-leg, opening its cleft, and are introduced into the encoded protein. Mutations can be introduced into a nucleic acid sequence by standard techniques, such as site-directed mutagenesis and PCR-mediated mutagenesis.

Some non-limiting examples of substituted cysteine residues in α/β subunits include the following and are denoted with a bold, underlined C:

```
Subunit
Human αIIb   946   RGEAQVWTQLLRACEERA-              963   (SEQ ID NO: 48);

Human αIIb   946   RGEAQVWTQLLRALCERA-              963   (SEQ ID NO: 49);

Human αv     942   TNSTLVTTNVTWGCQPAPM              960   (SEQ ID NO: 50);

Human αv     942   TNSTLVTTNVTWGICPAPM              960   (SEQ ID NO: 51);

Human β3     663   CCVRFQYYEDSS--GKSILYVVEEPECPKG   690   (SEQ ID NO: 52);

Human β3     663   CVVRFQYYEDSS--GKSILYVVEEPECCKG   690   (SEQ ID NO: 53);

Human β6     661   CCITFLITTDNE--GKTIIHSINEKDCPKP   688   (SEQ ID NO: 54);

Human β6     661   CLITFLITTDNE--GKTIIHSINEKDCCKP   688   (SEQ ID NO: 55);

Human β8     619   CCLMEQQ----------HYVDQTSECFSS    637   (SEQ ID NO: 56);

and

Human β8     619   CALMEQQ----------HYVDQTSECCSS    637   (SEQ ID NO: 57).
``` variation in the lower β-leg: α$_{IIb}$β$_3$ molecule 1 and α$_v$β$_3$. A view of the α-subunit only rotated about 90° indicates variation in the distance of the lower α-leg from the upper α-headpiece: α$_{IIb}$β$_3$ molecule 1 and molecule 2; α$_v$β$_3$. The headpieces of α$_{IIb}$β$_3$ molecule 1 and α$_v$β$_3$ show breathing at the β I/hybrid domain interface. Further information regarding the solved crystal structure for the α$_{IIb}$β$_3$ integrin can be found in a published paper by the inventors (Zhu, et al., *Molecular Cell* (2008) 32(6): 849-862).

Disulfide Bonds

Disulfide bond formation occurs between two cysteine residues that are appropriately positioned within the three-dimensional structure of an integrin polypeptide. In one embodiment of the invention, a polypeptide is stabilized in the closed conformation by introducing at least one cysteine substitution into the amino acid sequence such that a disulfide bond is formed. The introduction of a single cysteine substitution is performed in circumstances in which an additional cysteine residue is present in the native amino acid sequence of the polypeptide at an appropriate position such that a disulfide bond is formed. Alternatively, in another embodiment, two cysteine substitutions are introduced into the amino acid sequence of the polypeptide at positions that allow a disulfide bond to form, thereby stabilizing the polypeptide in a desired conformation.

In one embodiment of the invention, cysteine substitutions are introduced such that the formation of a disulfide bond is favored only in one protein conformation (i.e., a closed conformation), such that the protein is stabilized in that particular conformation.

Preparation of a modified Polypeptide of the invention by introducing cysteine substitutions can be achieved by mutagenesis of DNA encoding the integrin polypeptide of interest. For example, an isolated nucleic acid molecule encoding a modified integrin I-domain polypeptide can be created by introducing one or more nucleotide substitutions into the nucleotide sequence of an integrin gene such that one or more amino acid substitutions, e.g., cysteine substitutions, In another embodiment, the method of the invention can be used to stabilize a protein in a biologically inactive conformation, e.g., a conformation that is enzymatically inactive or does not have ligand binding capacity and/or effector functions, e.g., a "closed" conformation.

Proteins that are stabilized in a particular conformation find use in, for example, in proteomic screening technologies. In proteomic screens of tissues and disease states, antibodies, polypeptide, and/or small molecules that are specific for, e.g., an inactive protein conformer, can be used to assess the activity of different cellular signaling, metabolic, and adhesive pathways. Thus, associations can be made between specific diseases and the activation of specific biochemical and signaling pathways. Furthermore, the methods described herein relate to polypeptides, antibodies, and small molecules identified using the methods described herein and uses for same, e.g., to treat, for example, inflammatory disorders. Conformer-specific reagents can also be placed on chips and used to screen tissue extracts, or used to stain tissue sections. Furthermore, drugs or antibodies, e.g., anti-integrin antibodies which specifically recognize a modified integrin I-domain polypeptide, e.g., an anti-LFA-1 antibody which specifically recognizes a modified LFA-1 I-domain polypeptide, that are selective for a particular conformer, e.g., an open conformer or a closed conformer, may provide differential therapeutic effects. Therefore, selective screening assays using a protein stabilized in a particular conformer can be used to rationally obtain compounds with a desired activity.

Integrins

Integrins, exist on cell surfaces in an inactive conformation that does not bind ligand. Upon cell activation, integrins change shape (conformation) and can bind ligand. Over 20 different integrin heterodimers (different α and β subunit combinations) exist that are expressed in a selective fashion on all cells in the body. After activation, integrins bind in a specific manner to protein ligands on the surface of other cells, in the extracellular matrix, or that are assembled in the clotting or complement cascades. Integrins on leukocytes are of central importance in leukocyte emigration and in inflammatory and immune responses. Ligands for the leukocyte integrin Mac-1 ($\alpha_M\beta_2$) include the inflammation-associated cell surface molecule ICAM-1, the complement component iC3b, and the clotting component fibrinogen. Ligands for the leukocyte integrin LFA-1 ($\alpha_L\beta_2$) include ICAM-1, ICAM-2, and ICAM-3. Antibodies to leukocyte integrins can block many types of inflammatory and auto-immune diseases, by, e.g., modulating, or inhibiting, for example, cell to cell interactions, or cell to extracellular matrix interactions. Integrins on platelets are important in clotting and in heart disease and approved drugs that interact with platelet integrin function include the antibody abciximab (Reopro™) and the peptide-like antagonist eptifibatide (Integrilin™). Integrins on connective tissue cells, epithelium, and endothelium are important in disease states affecting these cells. They regulate cell growth, differentiation, wound healing, fibrosis, apoptosis, and angiogenesis. Integrins on cancerous cells regulate invasion and metastasis.

It is contemplated herein that an agent can be used to bind to integrins in the "closed conformation" in order to stabilize integrins in their off state and modify or prevent integrin activation.

One embodiment of the methods described herein provides a modified integrin I-domain polypeptide comprising at least one disulfide bond, such that the modified I-domain polypeptide is stabilized in a desired conformation. A modified integrin I-domain polypeptide of the invention may be derived from an I-domain of an integrin a subunit including $\alpha_1$, $\alpha_2$, $\alpha_{10}$, $\alpha_{11}$, $\alpha_D$, $\alpha_V$, $\alpha_X$, $\alpha_M$, $\alpha_E$, $\alpha_L$ (CD11a), $\alpha_M$ (CD11b) and $\alpha_X$ (CD11c).

Also contemplated herein are integrins with conservative substitutions. Conservative substitutions (substituents) typically include the substitution of one amino acid for another with similar characteristics (e.g., charge, size, shape, and other biological properties) such as substitutions within the following groups: valine, glycine; glycine, alanine; valine, isoleucine; aspartic acid, glutamic acid; asparagine, glutamine; serine, threonine; lysine, arginine; and phenylalanine, tyrosine. The non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. It is also contemplated herein that a substitution can occur among amino acid groups with varying characteristics.

In other embodiments, derivatives with amino acid substitutions which are less conservative may also result in desired derivatives, e.g., by causing changes in charge, conformation and other biological properties. Such substitutions would include, for example, substitution of a hydrophilic residue for a hydrophobic residue, substitution of a cysteine or proline for another residue, substitution of a residue having a small side chain for a residue having a bulky side chain or substitution of a residue having a net positive charge for a residue having a net negative charge. When the result of a given substitution cannot be predicted with certainty, the derivatives may be readily assayed according to the methods disclosed herein to determine the presence or absence of the desired characteristics. The polypeptides and proteins as described herein may also be modified by various changes such as insertions, deletions and substitutions, either conservative or nonconservative where such changes might provide for certain advantages in their use.

In a preferred embodiment, a cysteine residue is substituted into the integrin polypeptide to permit the formation of a disulfide bond. In one embodiment, a modified integrin I-domain polypeptide of the invention is encoded by an amino acid sequence containing at least one cysteine substitution, or alternatively two cysteine substitutions, as compared to the wild-type sequence.

The introduction of cysteine residues at appropriate positions within the amino acid sequence of the I-domain polypeptide allows for the formation of a disulfide bond that stabilizes the domain in a particular conformation, e.g., an inactive "closed" conformation. For example, the $\alpha_L$ L289C/K294C mutant and the αM Q163C/R313c mutants are stabilized in an inactive or "closed" conformation that does not bind ligand.

In one embodiment, described herein is a modified integrin I-domain which is comprised within an integrin subunit, and which may be further associated with an integrin β subunit. In another embodiment, a modified integrin I-domain polypeptide of the invention is a soluble polypeptide. Furthermore, the invention provides a modified integrin I-domain polypeptide which is operatively linked to a heterologous polypeptide. Modified integrin polypeptides of the invention include modified integrin I-domain and I-like domain polypeptides that are comprised within an integrin α or β subunit polypeptide, respectively; soluble modified integrin I-domain and I-like domain polypeptides; and modified integrin I-domain and I-like domain polypeptides that are operatively linked to a heterologous polypeptide, e.g., fusion proteins.

Some non-limiting examples of substituted cysteine residues in α/β subunits include the following and are denoted with a bold, underlined C:

| Subunit | | | | | |
|---|---|---|---|---|---|
| Human αIIb | 946 | RGEAQVWTQLLRACEERA- | 963 | (SEQ ID NO: 48); |
| Human αIIb | 946 | RGEAQVWTQLLRALCERA- | 963 | (SEQ ID NO: 49); |
| Human αv | 942 | TNSTLVTTNVTWGCQPAPM | 960 | (SEQ ID NO: 50); |
| Human αv | 942 | TNSTLVTTNVTWGICPAPM | 960 | (SEQ ID NO: 51); |
| Human β3 | 663 | CCVRFQYYEDSS--GKSILYVVEEPECPKG | 690 | (SEQ ID NO: 52); |
| Human β3 | 663 | CVVRFQYYEDSS--GKSILYVVEEPECCKG | 690 | (SEQ ID NO: 53); |
| Human β6 | 661 | CCITFLITTDNE--GKTIIHSINEKDCPKP | 688 | (SEQ ID NO: 54); |
| Human β6 | 661 | CLITFLITTDNE--GKTIIHSINEKDCCKP | 688 | (SEQ ID NO: 55); |

```
Human β8    619    CCLMEQQ----------HYVDQTSECFSS    637    (SEQ ID NO: 56);

and

Human β8    619    CALMEQQ----------HYVDQTSECCSS    637    (SEQ ID NO: 57).
```

The cDNAs, for multiple human integrin α and β subunit polypeptides have been cloned and sequenced, and the polypeptide sequences have been determined (see, for example, GenBank Accession Numbers: NM_002203 ($\alpha_2$), AF112345 ($\alpha_{10}$), NM_012211 ($\alpha_1$), NM_005353 ($\alpha_D$), NM_002208 ($\alpha_E$), NM_000887 ($\alpha_X$), NM_000632 ($\alpha_M$), NM_002209 ($\alpha_L$), X68742 and P56199 ($\alpha_1$), NM000211 ($\beta_2$), NM_000212 ($\beta_3$), NM_002214 ($\beta_8$)). In addition, the sequences encoding integrin α and β subunit polypeptides from other species are available in the art. Furthermore, as described previously, three dimensional structure of the $\alpha_M$, $\alpha_L$, $\alpha_1$ and $\alpha_2$ I-domains has been solved (Lee, J-O, et al. (1995) *Structure* 3:1333-1340; Lee, J-O, et al. (199S) *Cell* 80:631-638; Qu, A and Leahy, D J (1995) *Proc Natl Acad Sci USA* 92:10277-10281; Qu, A and Leahy, D J (1996) *Structure* 4:931-942; Emsley, J et al. (1997) *J Biol Chem* 272:28512-28517; Baldwin, E T et al. (1998) *Structure* 6:923-935; Kallen, J et al. (1999) J Mol Biol 292:1-9).

Isolated modified integrin polypeptides as described herein preferably have an amino acid sequence that is sufficiently identical to the amino acid sequence of a native integrin polypeptide, yet which comprise at least one, and alternatively two cysteine substitutions, such that a disulfide bond is formed that stabilizes the polypeptide in a desired conformation. As used herein, the term "sufficiently identical" refers to an amino acid (or nucleotide) sequence which contains a sufficient or minimum number of identical or equivalent (e.g., an amino acid residue that has a similar side chain) amino acid residues (or nucleotides) to an integrin amino acid (or nucleotide) sequence such that the polypeptide shares common structural domains or motifs, and/or a common functional activity with a native integrin polypeptide. For example, amino acid or nucleotide sequences which share at least 30%, 40%, or 50%, preferably 60%, more preferably 70%, 75%, 80%, 85% or 90%, 91%, 92%, 93%, 94%, 95% or greater identity and share a common functional activity (e.g., an activity of a modified integrin I-domain or I-like domain as described herein) are defined herein as sufficiently identical. An integrin I-domain polypeptide may differ in amino acid sequence from the integrin polypeptides disclosed herein due to natural allelic variation or mutagenesis.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In one embodiment, the percent identity between two amino acid sequences is determined using the Needleman and Wunsch (J. Mol. Biol. (48):444-453 (1970)) algorithm which has been incorporated into the GAP program in the GCG software package (available on the world wide web at gcg.com), using either a Blossom 62 matrix or a PAM250 matrix, and a gap weight of 16, 14, 12, 10, 8, 6, or 4 and a length weight of 1, 2, 3, 4, 5, or 6. In another embodiment, the percent identity between two nucleotide sequences is determined using the GAP program in the GCG software package (available on the world wide web at gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4.

Alternatively, sequences aligned for optimal comparison purposes can be used to find residues that are homologous among a variety of α or β integrin subunits, such that substitution of a cysteine residue known to stabilize an integrin in a closed conformation in one isoform can be extended to another isoform. One of skill in the art can readily align sequences in an optimal manner to determine a preferred site for cysteine substitution. Provided herein are sequences aligned in an optimal manner for the purpose of determining a preferred site for cysteine substitution. For example, mutation sites in $\alpha_V\beta_1$, and $\alpha_V\beta_5$ can be determined from alignment with $\alpha_V\beta_6$ and $\alpha_V\beta_8$ sequences. Alternatively, mutation sites in $\alpha_M\beta_2$ can be determined from alignment with the $\alpha_X\beta_2$ sequence.

In one embodiment, modified integrin polypeptides are produced by recombinant DNA techniques. For example, a modified integrin polypeptide can be isolated from a host cell transfected with a polynucleotide sequence encoding a modified integrin polypeptide (e.g., a I-domain polypeptide or a soluble I-domain fusion protein) using an appropriate purification scheme using standard protein purification techniques. Alternative to recombinant expression, a modified integrin polypeptide can be synthesized chemically using standard peptide synthesis techniques.

Integrins and Disease

Integrins are key targets in many diseases. Accordingly, isolated high affinity I-30 domains of the invention, as well as antibodies, or small molecule antagonists selective for activated leukocyte integrins can be used to modulate, e.g., inhibit or prevent, autoimmune and inflammatory disease, transplant rejection, ischemia/reperfusion injury as in hypovolemic shock, myocardial infarct, and cerebral shock. Furthermore, co-crystals of high affinity I domains bound to natural ligands and/or small molecule antagonists can readily be made, which will enable computational drug design, and advance modification and improvement of drug development candidates.

Accordingly, in one aspect the methods described herein provide a method for identifying a modulator of integrin activity comprising assaying the ability of a test compound to bind to a modified integrin I-domain polypeptide which is stabilized in the closed conformation. In another embodiment, the invention provides a method for identifying a compound capable of modulating the interaction of an integrin and a cognate ligand wherein binding of a ligand to a modified integrin I-domain polypeptide, which is stabilized in the closed conformation, is assayed in the presence and absence of a test compound.

As used herein, an integrin mediated disorder includes, for example, an inflammatory or immune system disorder, and/or a cellular proliferative disorder. Examples of integrin-mediated disorders include myocardial infarction, stroke, restenosis, transplant rejection, graft versus host disease or host versus graft disease, and reperfusion injury. An inflammatory or immune system disorder includes, but is not limited to adult respiratory distress syndrome (ARDS), multiple organ injury syndromes secondary to septicemia or trauma, viral infection, inflammatory bowel disease, ulcerative colitis, Crohn's disease, leukocyte adhesion deficiency II syndrome, thermal injury, hemodialysis, leukapheresis, peritonitis, chronic obstructive pulmonary disease, lung inflammation, asthma, acute appendicitis, dermatoses with acute inflammatory components, wound healing, septic shock, acute glomerulonephritis, nephritis, amyloidosis, reactive arthritis, rheumatoid arthritis, chronic bronchitis, Sjorgen's syndrome, sarcoidosis, scleroderma, lupus, polymyositis, Reiter's syndrome, psoriasis, dermatitis, pelvic inflammatory disease, inflammatory breast disease, orbital inflammatory disease, immune deficiency disorders (e.g., HIV, common variable immunodeficiency, congenital X-linked infantile hypogammaglobulinemia, transient hypogammaglobulinemia, selective IgA deficiency, necrotizing enterocolitis, granulocyte transfusion associated syndromes, cytokine-induced toxicity, chronic mucocutaneous candidiasis, severe combined immunodeficiency), autoimmune disorders, and acute purulent meningitis or other central nervous system inflammatory disorders.

Screening Assays

The methods described herein (also referred to herein as a "screening assay") can be used to identify modulators, i.e., candidate or test compounds or agents (e.g., peptides, antibodies, peptidomimetics, small molecules (organic or inorganic) or other drugs) which modulate integrin activity. These assays are designed to identify compounds, for example, that bind to an integrin I-domain polypeptide, e.g., an integrin I-domain polypeptide in an active conformation, binds to other proteins that interact with an integrin I-domain polypeptide, induce binding, and modulate the interaction of an integrin I-domain polypeptide with other proteins, e.g., an integrin ligand, e.g., ICAM, and thus modulate integrin activity.

In the case of an integrin stabilized in the closed conformation, a lack of integrin activity indicates that the integrin is stabilized in the "off" position. In order to screen candidate modulators that bind to this particular conformation, it is necessary to measure binding of the candidate agent to the integrin, rather than assessing integrin activity. Binding assays are known in the art and can be achieved using e.g., radioligand binding assays or fluorescence-detected binding. Candidate modulators that are capable of binding an integrin stabilized in a desired conformation will need to be confirmed as an inhibitor or stimulator of integrin activity using an integrin that is not stabilized in a particular conformation. Integrin activity assays for such purposes are well known in the art and/or are described herein.

In an alternate embodiment, a soluble, recombinant high affinity integrin I-domain can be used to screen for small molecule antagonists that interfere with integrin ligand binding. Furthermore, antagonists, e.g., antibodies, with direct/competitive and indirect/noncompetitive modes of inhibition can be discriminated, based on comparison with effects on wild-type integrin I-domains which show minimal ligand binding activity. For example, an indirect inhibitor should inhibit ligand binding by an activated, wild-type integrin I-domain, but not by a disulfide-locked high affinity I-domain.

In another embodiment, an assay is a cell-based assay comprising contacting a cell expressing a modified integrin polypeptide on the cell surface with a test compound and determining the ability of the test compound to modulate (e.g., induce or inhibit) an integrin activity. For example, a cell expressing a modified integrin I-domain polypeptide stabilized in an open conformation on the cell surface is contacted with a test compound, and the ability of the test compound to modulate adhesion to an integrin ligand is determined, as described herein.

In another embodiment, the ability of a test compound to modulate integrin ligand binding can also be determined, for example, by coupling a modified integrin I-domain polypeptide that is stabilized in e.g., an open conformation with a detectable label such that the binding of the modified integrin polypeptide can be determined by detecting the amount of labeled integrin I-domain binding to an immobilized integrin ligand.

Animal-based model systems, such as an animal model of inflammation, may be used, for example, as part of screening strategies designed to identify compounds which are modulators of integrin activity. Thus, the animal-based models may be used to identify drugs, pharmaceuticals, therapies and interventions which may be effective in modulating inflammation and treating integrin-mediated disorders. For example, animal models may be exposed to a compound suspected of exhibiting an ability to modulate integrin activity, and the response of the animals to the exposure may be monitored by assessing inflammatory activity before and after treatment. Transgenic animals, e.g., transgenic mice, which express modified integrin I-domain polypeptides as described herein can also be used to identify drugs, pharmaceuticals, therapies and interventions which may be effective in modulating inflammation and treating integrin-mediated disorders In another aspect, the methods described herein pertain to a combination of two or more of the assays described herein. For example, a modulator of integrin activity can be identified using a cell-based assay, and the ability of the agent to modulate integrin activity can be confirmed in vivo, e.g., in an animal such as an animal model for inflammation.

Moreover, screening assays can be used to identify inducers of integrin activity, for example, that mimic the activity of a integrin polypeptide, e.g., the binding of an integrin to a ligand or receptor, or the activity of an integrin towards an integrin responsive cell. Such compounds may include, but are not limited to, peptides, antibodies, or small organic or inorganic compounds. An anti-integrin antibody, e.g., an anti-LFA-1 antibody, which selectively binds to an open, activated conformer can be used to assess the ability of a test compound to activate, inactivate, or prevent activation of an integrin.

The test compounds can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233.

Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. '409), plasmids (Cull et al. (1992) Proc Natl Acad Sci USA 89:1865-1869) or on phage (Scott and Smith (1990) Science 249:386-390); (Devlin (1990) Science 249:404-406); (Cwirla et al. (1990) Proc. Natl. Acad. Sci. 87:6378-6382); (Felici (1991) J. Mol. Biol. 222:301-310); (Ladner supra.).

The methods described herein further pertain to novel agents identified by the above-described screening assays. With regard to intervention, any treatments which modulate integrin activity and/or inflammatory activity should be considered as candidates for human therapeutic intervention.

Other Embodiments

Reported herein are disulfide bonds between integrin α and β subunits in their C-terminal domains or in the linkers between these C-terminal domains and the transmembrane domain. These disulfides may be used in either intact integrins on the cell surface or truncated extracellular domain fragments. The results with disulfide bonds introduced into cell surface integrins are predictive of those that can be successfully introduced into extracellular domain fragments.

Also shown herein are disulfide bonds that stabilize integrins in the bent, low affinity conformation. The stabilized integrins bind ligands and ligand-mimetic Fab less well. The stabilized integrins have utility for screening for conformation-dependent antibodies and drug molecules. Antibodies and drugs may be identified that are selective for the active, non-bent, or inactive, bent integrins, using either cell surface integrins or extracellular domain fragments.

In addition, stabilized integrins on cells, in comparison with wild-type integrins, can be used to select for antibodies selective for the bent, inactive conformation or extended, active conformation. Alternatively, stabilized and wild-type ectodomain integrin fragments can be used to screen for drugs selective for the bent inactive conformation. Such drugs would bind to and stabilize the bent, inactive conformation, but not the extended, active conformation. Thus they would represent a novel class of non-competitive integrin antagonists.

The present invention may be as described in any one of the following numbered paragraphs.

1. A method for identifying a candidate modulator of integrin activity, the method comprising (a) contacting an integrin polypeptide with a candidate agent, wherein the integrin polypeptide is locked into a desired conformation; and (b) detecting binding of the candidate agent to the integrin polypeptide, wherein binding of the candidate agent to the integrin polypeptide is indicative that the candidate agent is a candidate modulator of integrin activity.
2. The method of paragraph 1, wherein the candidate agent is selected from the group consisting of an antibody, a small molecule, a chemical, a peptide, and a peptidomimetic.
3. The method of paragraph 1 or 2, wherein the candidate modulator stabilizes the integrin polypeptide into a closed conformation.
4. The method of paragraphs 1, 2, or 3 wherein the candidate modulator inhibits binding of an integrin ligand to the integrin polypeptide.
5. The method of any one of paragraphs 1-4, wherein the integrin polypeptide is selected from the group consisting of $\alpha_V\beta_3$, $\alpha_{IIb}\beta_3$, $\alpha_V b_6$, $\alpha_V\beta_1$, $\alpha_V\beta_5$, $\alpha_M\beta_2$, $\alpha_X\beta_2$, $\alpha_L\beta_2$, and $\alpha_V\beta_8$.
6. The method of any one of paragraphs 1-5, wherein locking the integrin polypeptide into the desired conformation comprises introducing a stabilizing disulfide bond into the integrin polypeptide.
7. The method of any one of paragraphs 1-6, wherein the disulfide bond is formed by a cysteine residue substitution of at least one amino acid residue of the integrin polypeptide.
8. The method of any one of paragraphs 1-7, wherein the substitution comprises a mutation selected from the group consisting of: L959C (human αIIb), E960C (human αIIb), I955C (human $\alpha_V$), Q956C (human $\alpha_V$), V664C (human $\beta_3$), P688C (human $\beta_3$), L662C (human $\beta_6$), P686C (human $\beta_6$), A619C (human $\beta_8$), and F636C (human $\beta_3$).
9. The method of any one of paragraphs 1-8, wherein an optimal sequence alignment is used to identify homologous residues for a cysteine substitution in an integrin polypeptide selected from the group consisting of $\alpha_V\beta_3$, $\alpha_{IIb}\beta_3$, $\alpha_V b_6$, $\alpha_V\beta_1$, $\alpha_V\beta_5$, $\alpha_M\beta_2$, $\alpha_X\beta_2$, $\alpha_L\beta_2$, and $\alpha_V\beta_8$.
10. The method of any one of paragraphs 1-9, wherein the candidate agent is assayed for activation or inhibition of integrin activity.
11. The method of any one of paragraphs 1-10, wherein a cell-based assay is used to determine integrin activity.
12. An integrin polypeptide composition comprising: a modified integrin polypeptide, wherein the integrin polypeptide is locked in a closed conformation.
13. The composition of paragraph 12, wherein the integrin polypeptide is modified by substitution of at least one amino acid residue for a cysteine residue, whereby a disulfide bond is formed.
14. The composition of paragraph 12 or 13, wherein the substitution comprises a mutation selected from the group consisting of: L959C (human αIIb), E960C (human αIIb), I955C (human $\alpha_v$), Q956C (human $\alpha_V$), V664C (human $\beta_3$), P688C (human $\beta_3$), L662C (human $\beta_6$), P686C (human $\beta_6$), A619C (human $\beta_8$), and F636C (human $\beta_3$).

EXAMPLES

Example 1

Structure of a Complete Integrin Ectodomain

Herein the inventors describe a crystal structure of platelet integrin $\alpha_{IIb}\beta_3$ in the bent conformation useful for screening for agents that bind to the integrin in its bent conformation. Crystals in $Ca^{2+}$ and $Mg^{2+}$ show that physiologically in the low affinity state the metal binding sites in the β I domain are fully occupied. Of two different $\alpha_{IIb}\beta_3$ molecules in the asymmetric unit, one has density for all integrin domains. Thus, the conformation in the bent state is revealed of I-EGF domains 1 and 2 at the β-knee, at the epicenter of conformational change. The overall structure, the linkages between domains, the arrangement of the legs within the bent structure, and the effect of hybrid domain swing-out on affinity for ligand, have profound implications for the mechanism of integrin activation. Use of this information in models of extended integrins experiencing forces at sites of cell adhesion reveals how integrin affinity is regulated by force exerted parallel to the membrane by a motile actin cytoskeleton. Integrin structure and mechanochemistry provides a natural mechanism for increasing integrin affinity upon cytoskeleton attachment and decreasing it upon cytoskeleton disassembly.

$\alpha_{IIb}\beta_3$ Crystal Structure and Negative Stain EM

A 2.55 Å resolution crystal structure of the complete $\alpha_{IIb}\beta_3$ ectodomain in $Ca^{2+}$ and $Mg^{2+}$ has been refined to an $R_{free}$ of 26.8% (FIG. 1A, Table 1). In comparisons to $\alpha_V\beta_3$ below, differences in resolution and refinement should be kept in mind. The 3.1 Å $\alpha_V\beta_3$ structure is refined to an $R_{free}$ of 36.7% (Xiong et al., 2004). $\alpha_{IIb}\beta_3$ has 95% and 0.4% residues in favored and outlier Ramachandran regions, respectively, and geometry in the 98th percentile (where 100 is the best); whereas $\alpha_V\beta_3$ has 76% and 6.7% residues in favored and outlier regions, respectively, and geometry in the 21st percentile; all values are as reported by MOLPROBITY (Davis et al., 2007). Water molecules, which have important roles in protein structures such as in forming hydrogen bonds and metal coordinations, have been added to the $\alpha_{IIb}\beta_3$ but not to the $\alpha_V\beta_3$ structure, as appropriate for their respective resolutions. No cis-prolines are present in the $\alpha_V\beta_3$ structure, whereas 6 are present in the $\alpha_{IIb}\beta_3$ structure. Two of the cis-prolines, Pro-163 and Pro-169, are in the ligand-binding $\beta_3$ I domain. The region around cis-Pro-169 has an electron density typical for the $\alpha_{IIb}\beta_3$ structure. There is a shift in the sequence-to-structure register between $\alpha_V\beta_3$ and $\alpha_{IIb}\beta_3$ at $\beta_3$ 167-176, in the specificity-determining loop that forms the outer rim of the ligand-binding pocket in the $\beta_3$ I domain. Thus, with its higher resolution and better refinement, the $\alpha_{IIb}\beta_3$ structure provides details about backbone conformation, hydrogen bonding, and side-chain packing that are important for understanding ligand and metal binding; and for accurate molecular dynamics simulations and structure-guided mutagenesis. Furthermore, for the first time, the structure factors for an integrin ectodomain have been deposited, opening access to the experimental electron density upon which the atomic models are based.

Figure 2:
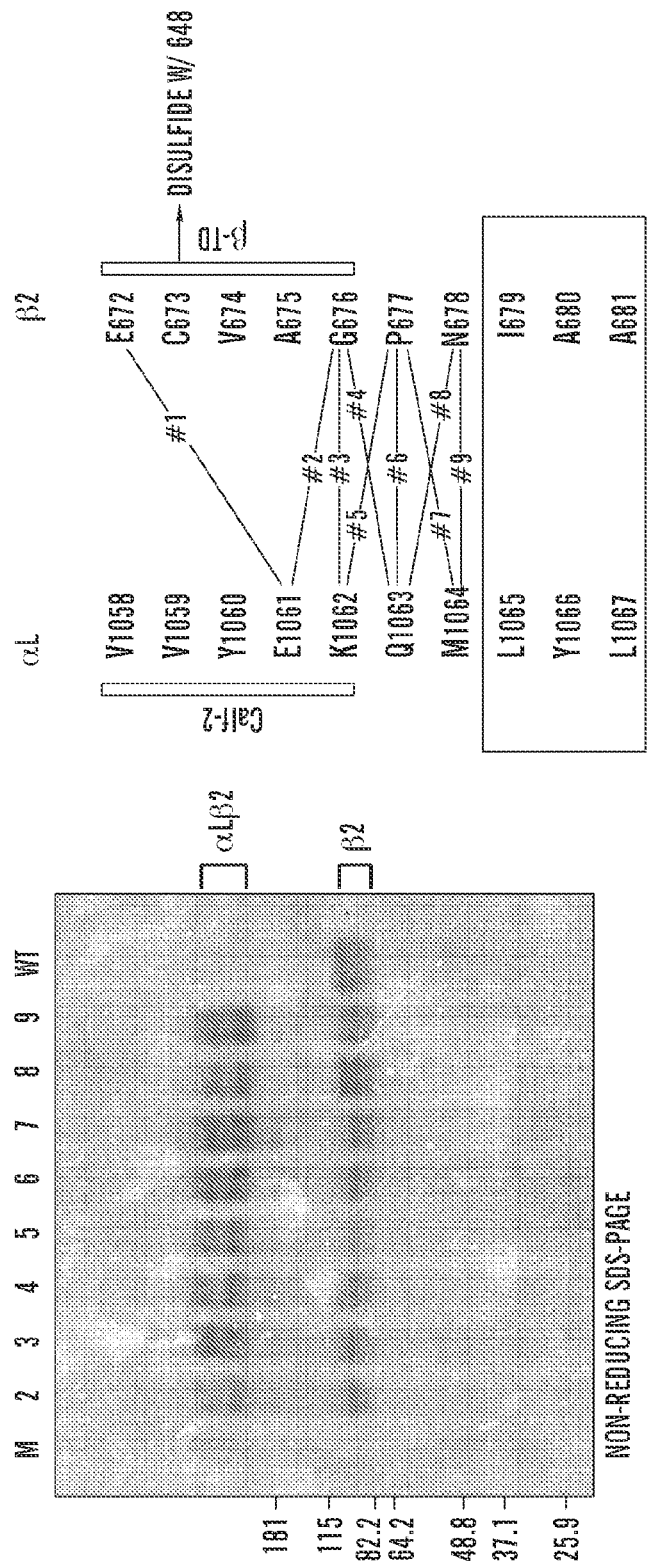
FIG. 2 show disulfide formation efficiency of the $\alpha_L\beta_2$ cys mutants on cell surface. The lane numbers in the left panel correspond to the combination of $\alpha_L$ and $\beta_2$ subunits connected by lines shown in the right panel. #1 was not well expressed in this particular experiment. FIG. discloses SEQ ID NOS 104 and 81, respectively, in order of appearance.
Figure 3:
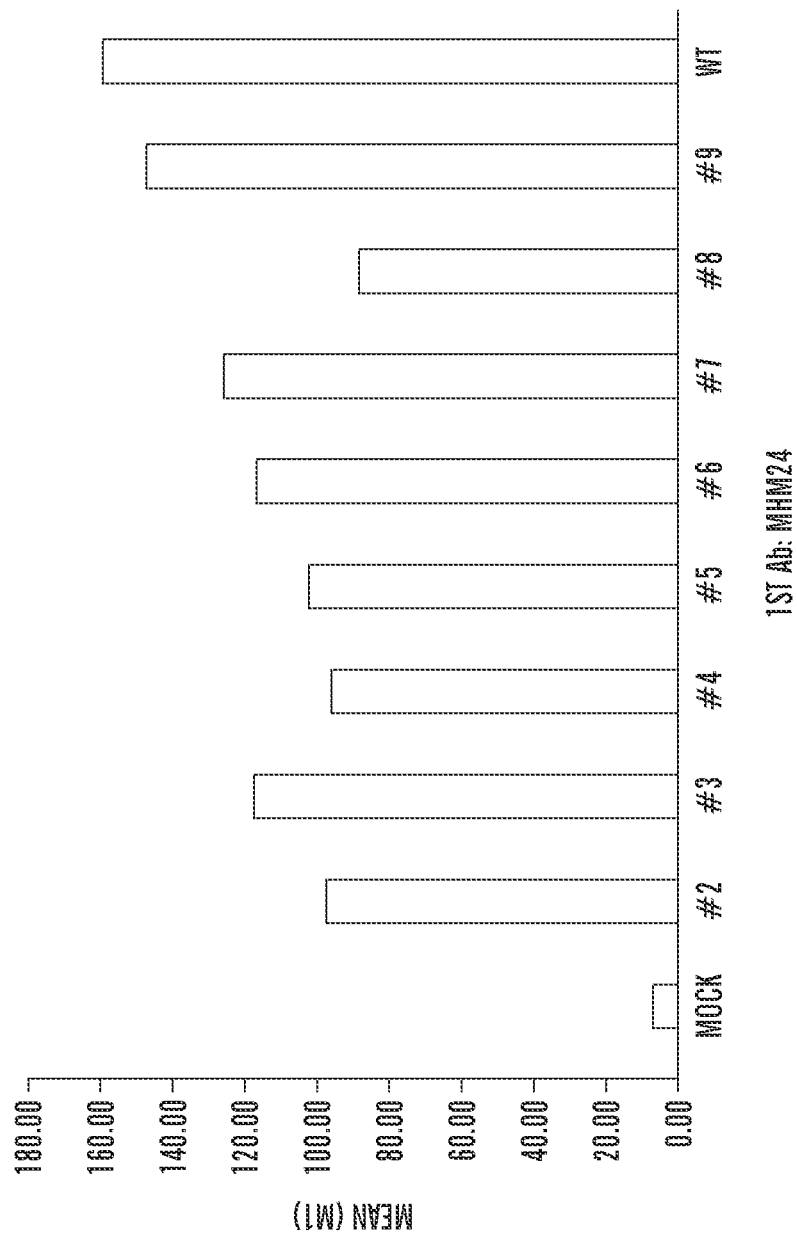
FIG. 3 shows expression level of disulfide locked $\alpha_L\beta_2$ mutants on 293T cell surface.
Figure 4:
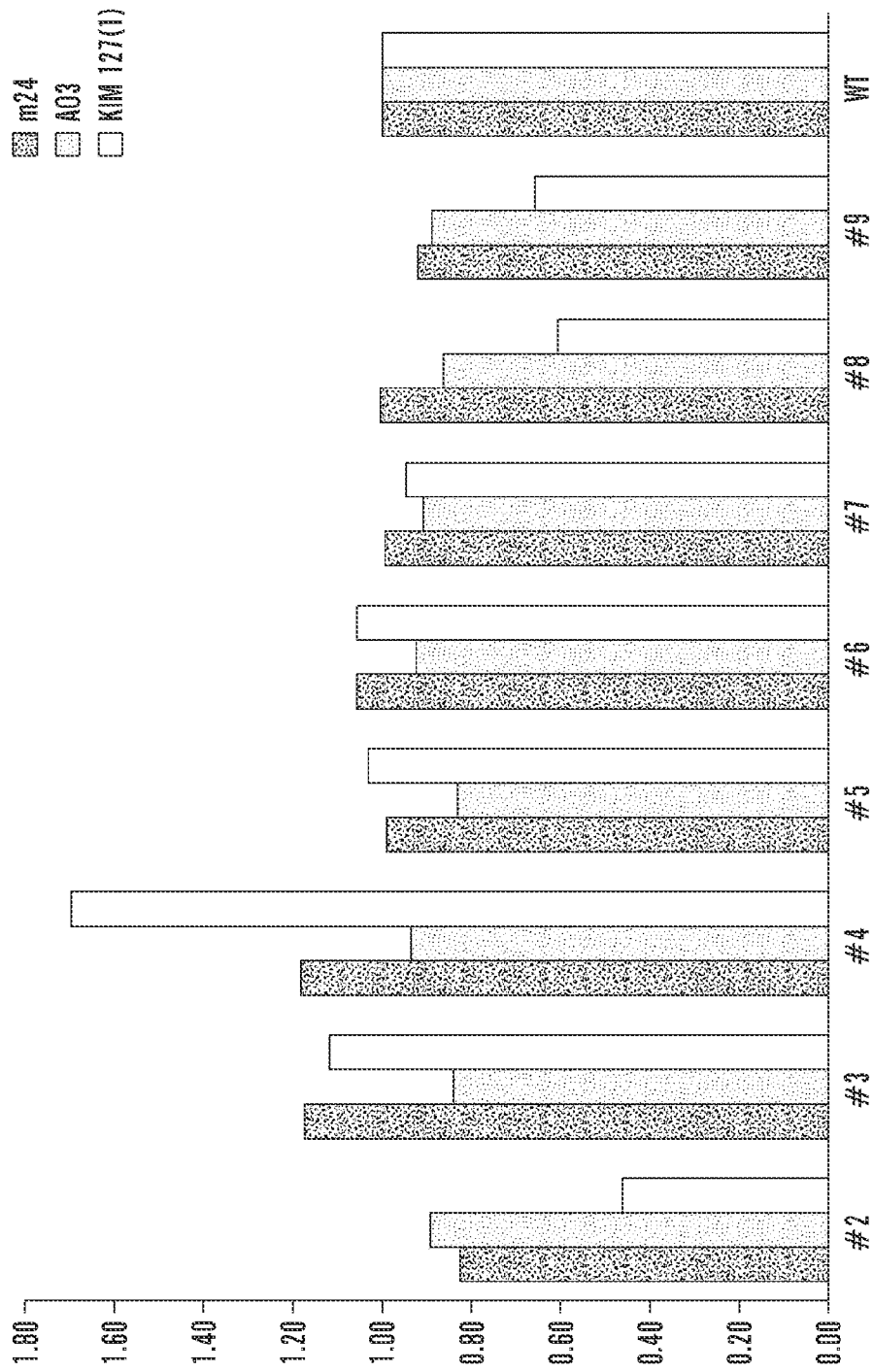
FIG. 4 shows exemplary LFA-1 disulfide mutants on 293T cell.
Figure 5A:
FIGS. 5A-5C show LFA-1 crosslinking on cell surface.
Figures 5B, 5C:
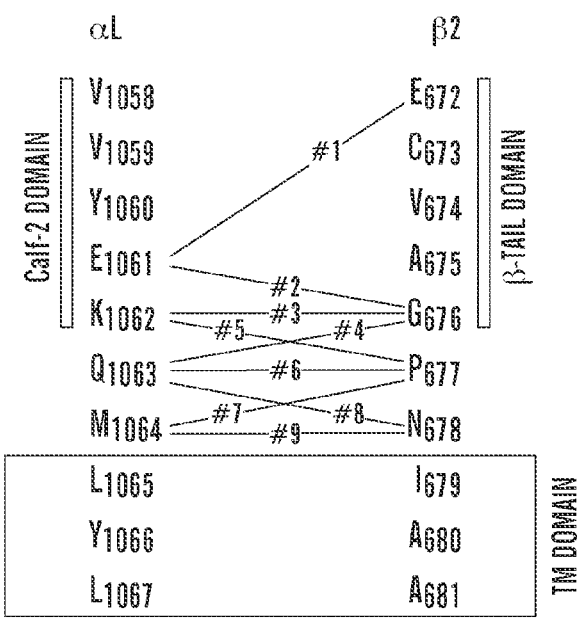
Figure 8A:
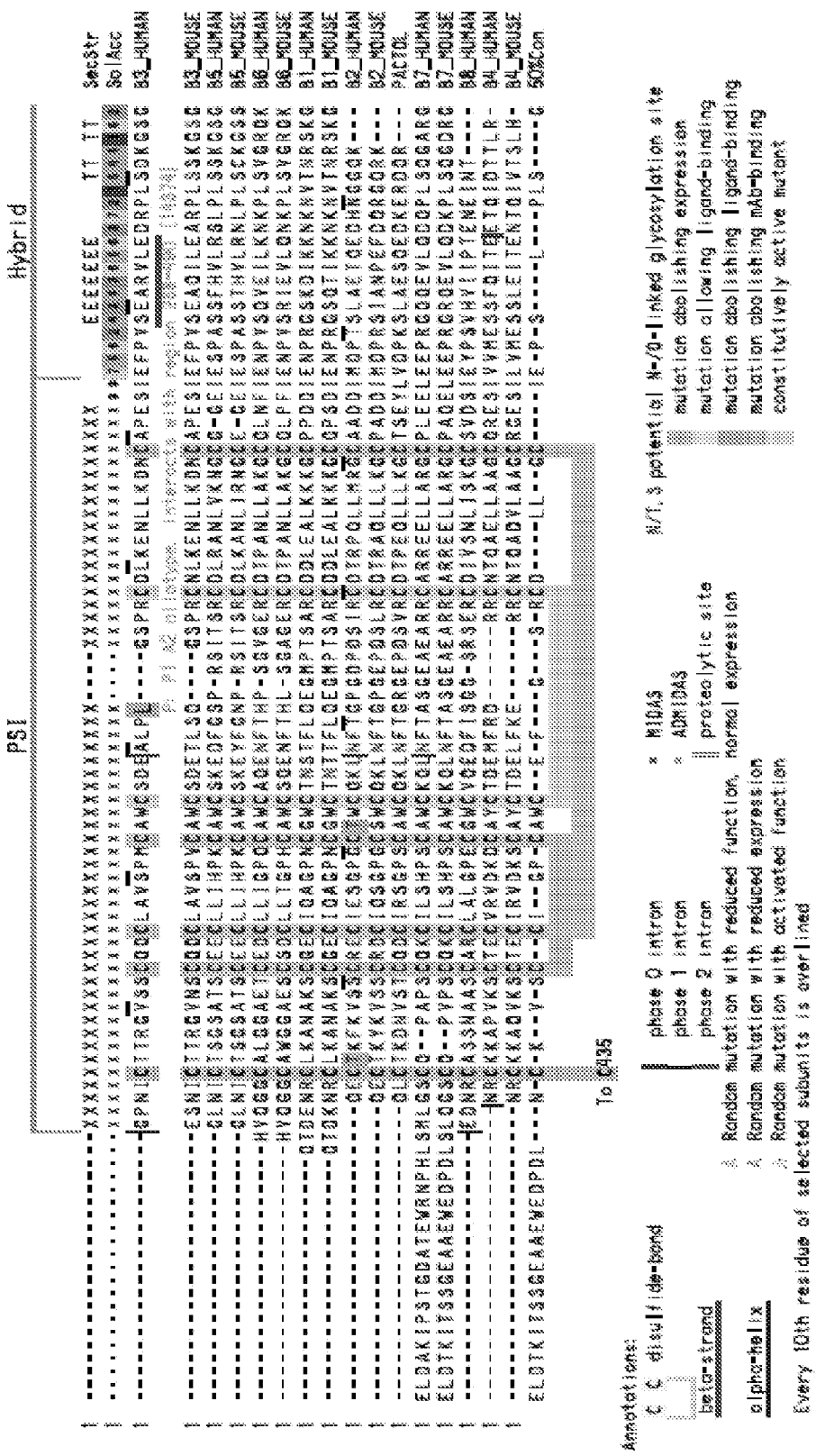
FIG. 8 shows optimal sequence alignments of exemplary integrin beta subunits.

Overall bent structure. The overall arrangement of domains in the two independent $\alpha_{IIb}\beta_3$ molecules in the crystal asymmetric unit is similar to that seen in $\alpha_V\beta_3$ crystals (FIG. 1C), except for differences in angles between domains described below that give insights into breathing. A similar bent conformation in solution in physiologic divalent cations is seen for three distinct $\alpha_{IIb}\beta_3$ constructs in negative stain EM with class averaging (FIG. 1F-H). The bent integrins from the three types of constructs are indistinguishable from one another (FIG. 1F panels 1-3, G panels 1-2, H panels 1-4) and show excellent cross-correlation with the $\alpha_{IIb}\beta_3$ crystal structure (FIG. 1F panels 1 and 5, G panels 1 and 5, and H, panels 1, 5 and 6). One construct was clasped by appending to the α and β ectodomain C-termini 15-residue linkers containing TEV protease sites, followed by ACID and BASE peptides that associate in an α-helical coiled-coil (Nishida et al., 2006). Association near the C-termini of the α and β subunit ectodomains that is provided in vivo by the association between the $\alpha_{IIb}$ and $\beta_3$ transmembrane domains (Luo et al., 2004) is mimicked by the clasp (Takagi et al., 2002). The clasped $\alpha_{IIb}\beta_3$ particles were 64% bent and 32% extended (with 4% unclassified) (FIG. 1F). Unclasped particles, in which the clasp was removed with TEV protease, were 44% bent and 52% extended (FIG. 1G). A third construct, which was identical to that used in crystallization, contained cysteines introduced in C-terminal portions of the $\alpha_{IIb}$ and $\beta_3$ subunits in positions that resulted in efficient disulfide bond formation in cell surface integrins (FIG. 2). These mutations, $\alpha_{IIb}$-L959C and $\beta_3$-P688C, stabilized the integrin in a bent, closed conformation that closely mimics the bent, closed conformation seen in the clasped and unclasped constructs that lack this disulfide. The disulfide-bonded construct was 100% bent (FIG. 1H).

The differing proportion of bent particles in the three preparations shows that tighter association near the C-termini correlated with maintenance of the bent conformation, and also, with resistance to activation on the cell surface (FIG. 2). This is in agreement with work on other soluble integrin preparations, and a large body of work on cell surface integrins, which has shown that association of the α and β subunit transmembrane and cytoplasmic domains stabilizes integrins in the low-affinity state and in the bent conformation (Luo et al., 2007).

Similar bent conformations have previously been described in EM studies of the resting states of $\alpha_V\beta_3$, $\alpha_X\beta_2$, and $\alpha_L\beta_2$ (Nishida et al., 2006; Takagi et al., 2002). Furthermore, extensive studies using mutations and antibodies to ligand-induced binding sites show that $\alpha_{IIb}\beta_3$ is compact on the cell surface when resting, and extended when activated (Honda et al., 1995; Luo et al., 2007). The similarity in packing of two independent examples of $\alpha_{IIb}\beta_3$ and of $\alpha_V\beta_3$ in crystal lattices and similar appearance of multiple soluble integrins in EM, together with the work cited above, strongly suggests that the bent crystal structure determined here is representative of the resting state of most, if not all, integrins. However, three cryo EM, EM, and hydrodynamic studies of detergent soluble $\alpha_{IIb}\beta_3$ from platelets have reached conclusions that are incompatible with one another, and with the domain arrangement seen here (Adair and Yeager, 2002; Rocco et al., 2008; Ye et al., 2008). The difficulty in obtaining a consensus view on $\alpha_{IIb}\beta_3$ structure may reflect the delicate equilibrium between bent and extended structures (FIG. 1G-H), averaging over ensembles of bent and extended conformations, the poor association of the $\alpha_{IIb}$ and $\beta_3$ transmembrane domains in detergent (Wegener and Campbell, 2008), and the ease with which the $\alpha_{IIb}$ and $\beta_3$ subunits dissociate, even on the platelet surface (Luo et al., 2003).

Conceptual advances since the previously described $\alpha_V\beta_3$ crystal structures allow us to describe the bent $\alpha_{IIb}\beta_3$ crystal structure in light of its physiological relevance as the low affinity integrin state, and as the starting point for integrin extension. Furthermore, the $\alpha_{IIb}\beta_3$ structure reveals I-EGF domains 1 and 2, and a highly acute bend between them in the bent conformation. In contrast, I-EGF domains 2, 3, and 4 extend in an almost straight orientation, with an approximate 90° left-handed twist between successive domains, to cover most of the length of the lower β-leg. The β-knee, at the junction between I-EGF1 and I-EGF2, is flanked on one side by the PSI domain and on the other by a knob-like projection in the thigh domain.

In the view in FIG. 1A, the lower α-leg is in front of the upper α-leg, whereas the lower β-leg is to the right of the upper β-leg, between it and the α-subunit. In other words, the bent α and β-legs are oriented approximately at right angles rather than parallel to one another. Thus the I-EGF domains of the lower β-leg are deeply buried in a narrow crevice between the upper β-leg on one side and the lower α-leg on the other, with the β I and β-propeller domains helping to form the back of the crevice (FIG. 1A). Exit of the β leg from the crevice appears to be the key step in integrin extension.

Overall extended structure. In the extended conformation of $\alpha_{IIb}\beta_3$, the α and β -legs straighten at the knees, and extend away from rather than fold up against the headpiece (FIGS. 1F and G, panel 4). The headpiece fragment excised from the crystal structure cross-correlates excellently with the headpiece seen in EM (FIGS. 1F and G, panels 6-8). Furthermore, cross-correlation demonstrated that in $Ca^{2+}$ and $Mg^{2+}$, extended $\alpha_{IIb}\beta_3$ predominantly assumes the closed headpiece conformation with low affinity for ligand, as seen in the bent crystal structure, rather than the open conformation with high affinity. Most extended class averages, whether with clasped or unclasped $\alpha_{IIb}\beta_3$, show the α-leg crossing over or under the β-leg (FIG. 1F, G, panel 4). Leg crossing appears to be a consequence of upper leg configuration in the bent conformation with the long axis of 1-EGF1 pointing toward the α-knee (FIG. 1A). When the bent crystal structure is extended at the α and β-knees, leg crossing results. However, the legs are highly flexible, and for clarity are shown side-by-side in FIG. 1B. Extended integrins with crossed and uncrossed legs have also been seen for activated $\alpha_V\beta_3$, $\alpha_X\beta_2$, and detergent soluble $\alpha_{IIb}\beta_3$ integrins (Iwasaki et al., 2005; Nishida et al., 2006; Takagi et al., 2002).

Figure 1B:
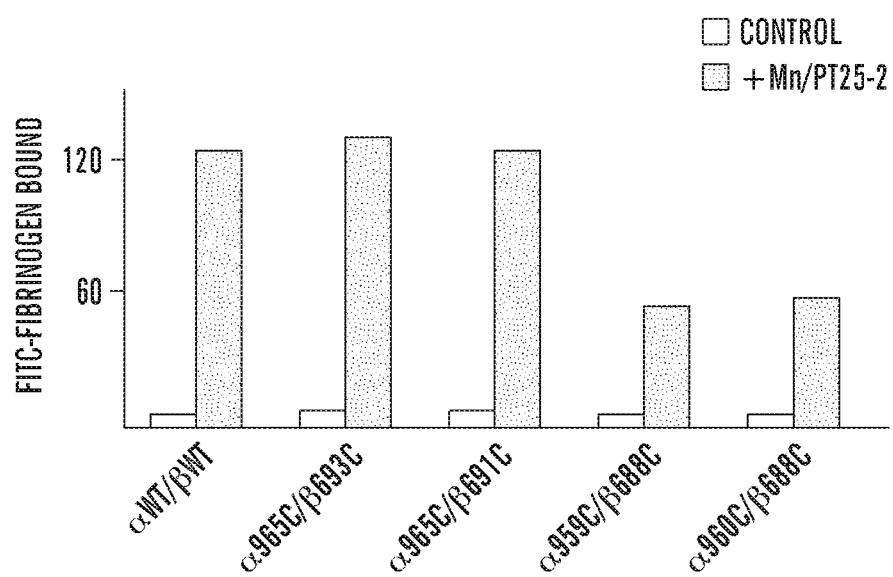

After physiological activation of $\alpha_{IIb}\beta_3$ on platelets or treatment with high concentrations of ligands, multiple ligand-induced binding site (LIBS) epitopes are exposed. These epitopes map to the lower β-leg, and to the PSI domain (Honda et al., 1995). The lower β-leg is buried in a cleft in the bent conformation (FIG. 1A), but will be exposed in the extended conformation (FIG. 1B). Similarly, the LIBS epitope in the PSI domain, mapped to residues 1-6 (Honda et al., 1995), is masked by I-EGF2 in the bent conformation (FIG. 1A). By contrast, this epitope is exposed after extension at the I-EGF1/I-EGF2 interface in the β-knee brings I-EGF2 away from the PSI domain (FIG. 1B). The previous functional studies, together with the location of these epitopes within the $\alpha_{IIb}\beta_3$ structure, demonstrate that bent and extended $\alpha_{IIb}\beta_3$ represent latent and activated integrins, respectively, contradict suggestions that $\alpha_{IIb}\beta_3$ is extended in the resting state (Rocco et al., 2008; Ye et al., 2008), and agree with election tomography of active, detergent soluble $\alpha_{IIb}\beta_3$ showing that it is extended (Iwasaki et al., 2005).

Methods
Crystallography

Briefly, $\alpha_{IIb}$ and β3 ectodomains were fused to C-terminal segments containing a tobacco etch protease (TEV) site, ACID or BASE coiled-coils, and strep II or His6 (SEQ ID NO: 105) tags, with or without $\alpha_{IIb}$-L959C and $\beta_3$-P688C mutations to introduce a disulfide bond. Proteins were purified from CHO Lec 3.2.8.1 cell supernatants. $\alpha_{IIb}\beta_3$ with the extra disulfide bond and the C-terminal tag removed by TEV protease in buffer containing 1 mM CaCl2 was crystallized in 10% PEG 3350, 50 mM magnesium acetate, and 0.1 M imidazole, pH 7.0. Diffraction data collected at 19-ID of APS was solved using molecular replacement in space group P41. Final refinement with REFMAC5 utilized TLS and NCS. Crystals of the $\alpha_{IIb}\beta_3$ ectodomain contain two molecules per asymmetric unit. Density is present for all ectodomain residues ($\alpha_{IIb}$ 1-959 and $\beta_3$ 1-690) except for five loops, and in one molecule, the C-terminal portion of the β-tail domain. Thirteen or 18 N-linked carbohydrate residues are visualized in each molecule. I-EGF1 from the complete $\alpha_{IIb}$ $\beta_3$ ectodomain was used to model density for this domain in re-refined $\alpha_{IIb}$ $\beta_3$ headpiece structures with (Springer et al., 2008) or without Fab (Table 1).

Negative stain EM

The clasped and unclasped $\alpha_{IIb}\beta_3$ was purified on a Superdex 200 HR column equilibrated with TBS plus 1 mM $Ca^{2+}$ and 1 mM $Mg^{2+}$. The peak fraction was adsorbed to glow discharged carbon-coated copper grids, stained with uranyl formate, and inspected with an FEI Tecnai 12 electron microscope operated at 120 kV. Images were acquired at a nominal magnification of 67,000×. Imaging plates were scanned and digitized with a Ditabis micron imaging plate scanner (DITABIS Digital Biomedical Imaging System, AG, Pforzheim, Germany) using a step size of 15 μm and 2×2 pixels were averaged to yield a final pixel size of 4.46 Å at the specimen level. 2,000-5,000 particles were interactively collected, windowed into 75×75-pixel individual images, and subjected to ten cycles of multi-reference alignment and classification. Image processing and cross-correlation using the SPIDER image processing package (Frank et al., 1996) was as described previously (Nishida et al., 2006).

Example 2

Disulfide-Stabilized Integrins for Antibody, Ligand-Binding and Drug Screening

Methods
Production of Soluble $\alpha_{IIb}\beta_3$

DNA constructs of the extracellular domains of soluble $\alpha_{IIb}\beta_3$ were made and expressed as described previously (Takagi, et al), or with modifications as described below to introduce an additional disulfide. $\alpha_{IIb}$ extracellular domain residues 1-963 were fused with a tobacco etch virus (TEV) protease site, acidic coiled coil and StrepII tag to give the C-terminal sequence QLLRALEERA/TGGLENLYFQG-GENAQCEKELQALEKENAQLEWELQALE-KELAQWSHPQFEK (SEQ ID NO: 58), where the slash marks the fusion position, and then inserted into the pcDNA3.1 vector with hygromycin resistance gene. β3 extracellular domain residues 1-690 were fused with a TEV protease site, basic coiled coil and His6 (SEQ ID NO: 105) tag to give the C-terminal sequence VVEEPECPKG/TSGLENLY-FQGGKNAQCKKKLQALKKKNAQLK-WKLQALKKKLAQGGHHHHH H (SEQ ID NO: 59), where the slash marks the fusion position, and then inserted into the pEF1 vector with the puromycin resistance gene. Cysteine mutations $\alpha_{IIb}$-L959C and $\beta_3$-P688C were introduced at the underlined positions in the above sequences using a site-directed mutagenesis kit. Plasmid DNA of the $\alpha_{IIb}$ and $\beta_3$ constructs was co-transfected into CHO Lec 3.2.8.1 cells using electroporation. Cells were cultured in selection medium containing puromycin and hygromycin for about 10 days until single colonies were obtained. ELISA was used with mAb 7E3 as the capturing antibody and biotinylated mAb AP3 as the detecting antibody to screen for clones with high expression cell lines. Three rounds of screening of approximately 150 colonies yielded one clone (clone #11) with an expression level of about 5 mg/L for the disulfide-bonded construct. The clone was expanded and cultured in roller bottles.

The culture supernatant was concentrated by ultra-filtration and exchanged into 25 mM TrisHCl (pH 8.0) and 300 mM NaCl, plus 5 mM $CaCl_2$ and 10 mM imidazole (loading buffer). The solution was loaded onto a Ni-NTA matrix (QIAGEN™) column (5 ml of resin per 1 liter of culture supernatant) pre-equilibrated with loading buffer. The column was then washed with ten bed-volumes of loading buffer plus 20 mM imidazole and the bound proteins were eluted with five bed-volumes of the loading buffer plus 250 mM imidazole. Eluted proteins were concentrated with an Amicon YM-30 filter (Millipore, Bedford, Mass.) into 20 mM TrisHCl (pH 7.5) and 150 mM NaCl (TBS), plus 5 mM CaCl$_2$, and loaded on a Strep-Tactin column (IBA, St. Louis, Mo.), which was washed with ten bed-volumes of the same buffer. Protein was eluted with the same buffer plus 5 mM desthiobiotin. Purified $\alpha_{IIb}\beta_3$ was concentrated with an Amicon YM-30 centrifugal filter to about 1 mg/ml and treated with TEV protease (2.5 units of enzyme per µg $\alpha_{IIb}\beta_3$) at 25° C. for 16 hr in TBS plus 5 mM CaCl$_2$. The unclasped $\alpha_{IIb}\beta_3$ protein was collected in the flow-through of a second Ni-NTA chromatography step. Purified $\alpha_{IIb}\beta_3$ was subjected to Superdex 200 chromatography (Amersham, Piscataway, N.J.) in 20 mM TrisHCl (pH 8), 150 mMNaCl, 1 mM CaCl$_2$.
Negative stain EM.

The clasped and unclasped $\alpha_{IIb}\beta_3$ was purified on a Superdex 200 HR column in Tris saline, 1 mM Ca$^{2+}$, 1 mM Mg$^{2+}$. The peak fraction was adsorbed to glow discharged carbon-coated copper grids, stained with uranylformate, and inspected with an FEI Tecnai 12 electron microscope operated at 120 kV. Images were acquired at a nominal magnification of 67,000×. Imaging plates were scanned and digitized with a Ditabis micron imaging plate scanner (DITABIS Digital Biomedical Imaging System, AG, Pforzheim, Germany) using a step size of 15 gm and 2×2 pixels were averaged to yield a final pixel size of 4.46 Å at the specimen level. 2,000-5,000 particles were interactively collected, windowed into 75×75-pixel individual images, and subjected to ten cycles of multi-reference alignment and classification. Images were processed and cross-correlated using SPIDER (Frank, et al) as described (Nishida, et al).
Disulfide Crosslinking and Immunoprecipitation Twenty-four hours after transfection, 293T cells in 12-well plates with 1.5 ml DMEM medium containing 10% FCS were pre-treated with 15 µg/ml of 2-BP for 1 hour, the medium was replaced with 0.75 ml Met, Cys-free RPMI 1640 (Sigma R-7513), supplemented with 10% dialyzed FCS, 10 µl [35S] cysteine/methionine (10mCi/ml, PerkinElmer Life Science), 15 µg/ml 2-BP. After 1.5 h at 37° C., 0.75 ml of RPMI 1640 containing 10% FCS, 500 µg/ml cysteine, 100 µg/ml methionine, and 15 µg/ml 2-BP was added, and cells chased for at least 17 hours. Cells were detached by vigorous pipetting, washed, and suspended (10$^6$ cells in 100 µl) in Tris-buffered saline (TBS, 20 mM Tris-HCl, pH 7.5, 150 mM NaCl) containing 1 mM Ca$^{2+}$/1 mM Mg$^{2+}$ and proteinase inhibitors (1 µg/ml each aprotinin, leupeptin, and pepstatin). The cells were kept intact or broken by 3 cycles of freezing on dry ice and thawing. Saponin (40 µg/ml) gave results identical to freeze-thawing, but freeze-thawing was adapted as the least membrane-perturbing. After chilling on ice for 5 minutes, 200 µM CuSO$_4$/1000 µM o-phenanthroline was added by 10 fold dilution from stock solution, and cells were incubated on ice for another 10 minutes. N-ethylmaleimide (10 mM) was added and after 10 minutes on ice, cells were lysed with an equal volume of TBS containing 2% Triton X-100 and 0.1% NP-40 for 10 minutes on ice. Cell lysates were cleared by centrifugation at 14,000 RPM for 10 minutes and immuno-precipitated with anti-β3 mAb AP3 and protein G agarose at 4° C. for 1 hour. The precipitated proteins were subjected to non-reducing 7.5% SDS-PAGE. The SDS-PAGE gel was dried and exposed for 3 h to storage phosphor screens which were measured with a Storm PhosphorImager (Molecular Dynamics, Sunnyvale, Calif., United States). Disulfide bond formation was quantitated as the intensity of the disulfide-bonded heterodimer band divided by the sum of the intensity of αIIb, β3, and heterodimer bands. Specific intensity of each band was determined by subtraction of background intensity.

For constitutively cross-linked extracellular and exofacial residues, crosslinking was also measured in redox buffer and after DTT treatment followed by Cu-phenanthroline. For redox buffer treatment, cells were suspended in pH 8.2 TBS containing 1 mM Ca$^{2+}$/1 mM Mg$^{2+}$ and 5 mM cysteamine/1 mM cystamine, and incubated at 37° C. for 1 hour. Following addition of 10 mM N-ethylmaleimide, cells were lysed and immunoprecipitated as described above.
Results
Disulfide Bonds Near the Ectodomain-transmembrane Domain Junction of $\alpha_{IIb}\beta_3$ The interface between the $\alpha_{IIb}$ and $\beta_3$ TM domains has been defined by scanning the TM domains with cysteine and determining the propensity for disulfide bond formation (Luo, et al). Similarly disulfide-bond formation between residues just outside the plasma membrane in intact integrins expressed on the surface of 293 cells was examined (FIG. 2A). A cysteine introduced at residue 688 in the $\beta_3$ tail domain efficiently formed an inter-subunit disulfide bond with a cysteine introduced at either residue 959 or 960 in the $\alpha_{IIb}$ calf-2 domain (FIG. 2A).

Furthermore, cysteine introduced at $\beta_3$ 686 efficiently disulfide-bonded to cysteine introduced at $\alpha_{IIb}$ 958, 959, and 960, but not 957 (data not shown). Cysteine introduced at residues $\beta_3$ 691 or 693, in the linker between the $\beta_3$ tail domain and transmembrane domain, also efficiently formed disulfides with residue 965, in the linker between the $\alpha_{IIb}$ calf-2 domain and transmembrane domain (FIG. 2A). $\alpha_{IIb}$ residues 958-960 and $\beta_3$ residues 686 and 688 are in structured portions of the calf-2 and β-tail domains, respectively. Without wishing to be bound by theory, the ability to form a range of disulfides between these residues indicates that a range of orientations between the calf-2 and β-tail domains can occur on the cell surface. This is consistent with the different orientations seen between calf-2 and β-tail domains in molecules 1 and 2 in $\alpha_{IIb}\beta_3$ crystals, even when an $\alpha_{IIb}$-959 to $\beta_3$-688 disulfide is present.

Disulfide cross-links between $\alpha_{IIb}$ and $\beta_3$ transmembrane residues prevent transmission of activation signals across the membrane both in the inside-out and outside-in directions; however, they do not prevent activation of extracellular ligand binding by extracellular signals, such as Mn$^{2+}$ and activating antibody (Luo, et al; Zhu, et al). Similarly, the α965C/β693C and α965C/β691C mutants with inter-subunit disulfide bonds in the linker regions could be activated by extracellular stimuli to bind the ligand fibrinogen as efficiently as wild-type (FIG. 2B). However, the α959C/β688C and α960C/β688C mutants with inter-subunit disulfide bonds between C-terminal β tail domain and calf-2 residues were partially resistant to activation by Mn$^{2+}$ and PT25-2 antibody. These results indicate that the tighter association between the α and β subunits enforced by the more ectodomain-proximal disulfide between the β-tail and calf-2 domains makes them more resistant to activation.

The greater stability (higher frequency) of bent particles in $\alpha_{IIb}\beta_3$ preparations with than without the $\alpha_{IIb}$959C/β3688C disulfide correlates with the greater resistance to activation of cell-surface $\alpha_{IIb}$959C/β3688C than wild-type $\alpha_{IIb}\beta_3$ (FIG. 1B). This finding is consistent with conclusions from EM and functional studies on $\alpha_V\beta_3$ and $\alpha_X\beta_2$ integrins, that the bent conformation represents the resting state and integrin activation requires extension (Takagi, et al; Nishida, et al).
EM Studies on Disulfide-Mutant Integrins A similar bent conformation in solution with physiologic divalent cations is seen for three distinct $\alpha_{IIb}\beta_3$ constructs in negative stain EM with class averaging. The bent integrins from the three types of constructs are indistinguishable from one another and show excellent cross-correlation with the $\alpha_{IIb}\beta_3$ crystal structure. One construct was clasped by appending to the α and β ectodomain C-termini 15-residue linkers containing TEV protease sites, followed by an α-helical coiled-coil (Nishida, et al). Association near the C-termini of the α and β subunit ectodomains provided in vivo by association between the $\alpha_{IIb}$ and $\beta_3$ transmembrane domains (Luo, et al) is mimicked by the clasp (Takagi, et al). The clasped $\alpha_{IIb}\beta_3$ particles were 64% bent and 32% extended (with 4% unclassified) (FIG. 1F). Unclasped particles, in which the clasp was removed with TEV protease, were 44% bent and 52% extended. A third construct, which was identical to that used in crystallization, contained cysteines introduced in C-terminal portions of the $\alpha_{IIb}$ and $\beta_3$ subunits in positions that resulted in efficient disulfide bond formation in cell surface integrins. The disulfide-bonded construct was 100% bent.

The differing proportion of bent particles in the three preparations shows that tighter association near the C-termini correlates with maintenance of the bent conformation, and also, with resistance to activation on the cell surface (FIG. 2). This is in agreement with work on other soluble integrin preparations, and a large body of work on cell surface integrins, which has shown that association of the α and β subunit transmembrane and cytoplasmic domains stabilizes integrins in the low-affinity state and in the bent conformation (reviewed in Luo, et al).

Example 3

$\alpha_X\beta_2$ was clasped at its C-terminal residues shown herein in the following table. Following the protein sequence, generic coiled coil and hexameric histidine (SEQ ID NO: 105) tag were added to the C terminal of construct. Soluble expression of ectodomain was performed via transfecting 293S cells with PEI (Polyethylenimine) method. Following five days of incubation in 37° C., DMEM media containing 10% FCS and 10% $CO_2$, Western blotting with anti-His antibody was performed to investigate formation disulfide formation. Table below discloses SEQ ID NOS 60-69, respectively, in order of appearance.

5 constructs for both $\alpha_x$ and $\beta_2$ were transfected, and 25 (5×5) combinations of heterodimeric formation were tested by Western blotting. 5 constructs of $\alpha_x$ with P677C of $\beta_2$ constructs resulted in partial formation of disulfide linkage, whereas rest of heterodimeric combinations displayed completely formation dilsulfide. On the other hand, expression level of P677C of $\beta_2$ construct was comparable to wild type expression based on ELISA, and considerable lessening of expression level was observed for other 20 combinations.

TABLE 1

| X-ray diffraction data and refinement | | |
|---|---|---|
| Protein | $\alpha_{IIb}\beta_3$ ectodomain | $\alpha_{IIb}\beta_3$ headpiece |
| Spacegroup | $P4_1$ | $P6_2$ |
| Unit cell (a, b, c) (Å) | 81.3, 81.3, 654.6 | 332.1, 332.1, 88.3 |
| (α, β, γ) (°) | 90, 90, 90 | 90, 90, 120 |
| Wavelength (Å) | 0.97934 | 0.9760 |
| Resolution (Å) | 50-2.55 | 45-2.90 |
| Number of reflections (total/unique) | 614,293/135,066 | 1,251,268/122,126 |
| Completeness (%) | 98.6/93.9* | 98.3/93.9* |
| I/σ(I) | 12.2/2.1* | 17.4/3.0* |
| Rmerge (%)¶ | 7.1/56.6* | 9.7/60.2* |
| Rwork¶¶/Rfree‡‡ | 0.233/0.268 | 0.174/0.196 |
| RMSD: Bond (Å) | 0.003 | 0.006 |
| Angle (°) | 0.736 | 0.659 |
| Ramachandran plot** | 95.0%/4.6%/0.4% | 96.9%/2.9%/0.2% |
| PDB code | | (prev. 1TYE) |

*Asterisked numbers correspond to the last resolution shell.

¶$R_{merge} = \Sigma_h\Sigma_i|I_i(h) - \langle I(h)\rangle|/\Sigma_h\Sigma_i I_i(h)$, where $I_i(h)$ and $\langle I(h)\rangle$ are the ith and mean measurement of the intensity of reflection h.

¶¶$R_{work} = \Sigma_h||F_{obs}(h)| - |F_{calc}(h)||/\Sigma_h|F_{obs}(h)|$, where $F_{obs}(h)$ and $F_{calc}(h)$ are the observed and calculated structure factors, respectively. No I/σ cutoff was applied.

‡‡$R_{free}$ is the R value obtained for a test set of reflections consisting of a randomly selected 1.3% subset of the data set excluded from refinement.

**Residues in favorable, allowed, and outlier regions of the Ramachandran plot as reported by MOLPROBITY (Davis et al., 2007).

```
             PreCission/linkerLG /coiled coil         /His-tag
                                |
Human αX 1079 EKgcg------LQTLFQGP LG AQGEKELQALEKENAQLEWELQALEKELAQ-HHHHHH Human αX 1079 EKYgcg-----LQTLFQGP LG AQGEKELQALEKENAQLEWELQALEKELAQ-HHHHHH Human αX 1079 EKYKgcg----LQTLFQGP LG AQGEKELQALEKENAQLEWELQALEKELAQ-HHHHHH Human αX 1079 EKYKVgcg---LQTLFQGP LG AQGEKELQALEKENAQLEWELQALEKELAQ-HHHHHH Human αX 1079 EKYKVHgcg--LQTLFQGP LG AQGEKELQALEKENAQLEWELQALEKELAQ-HHHHHH PreCission/linkerLG /coiled coil         /His-tag
                                |
Human β2  672 ECgcg------LQTLFQGP LG AQGKKKLQALKKKNAQLKWKLQALKKKLAQ-HHHHHH Human β2  672 ECVgcg-----LQTLFQGP LG AQGKKKLQALKKKNAQLKWKLQALKKKLAQ-HHHHHH Human β2  672 ECVAgcg----LQTLFQGP LG AQGKKKLQALKKKNAQLKWKLQALKKKLAQ-HHHHHH Human β2  672 ECVAGgcg---LQTLFQGP LG AQGKKKLQALKKKNAQLKWKLQALKKKLAQ-HHHHHH Human β2  672 ECVAGPgcg--LQTLEQGP LG AQGKKKLQALKKKNAQLKWKLQALKKKLAQ-HHHHHH
```

TABLE 2

Variation in inter-domain angles in integrins[a].

| Domain interface | bent $\alpha_{IIb}\beta_3$[b] bent $\alpha_{IIb}\beta_3$ | bent $\alpha_{IIb}\beta_3$[c] bent $\alpha_V\beta_3$ | bent $\alpha_{IIb}\beta_3$[d] open $\alpha_{IIb}\beta_3$ | open $\alpha_{IIb}\beta_3$[e] open $\alpha_{IIb}\beta_3$ | bent $\beta_3$[f] frag $\beta_2$ | frag $\beta_2$[g] frag $\beta_2$ |
|---|---|---|---|---|---|---|
| α β-propeller-α thigh | 0.5° | 9.7-9.9° | — | — | — | — |
| α thigh-α calf1 | 1.3° | 19-20° | — | — | — | — |
| α calf1-α calf2 | 3.4° | 14-17° | — | — | — | — |
| β I-β hybrid | 0.2° | 6.7-6.7° | 58-70° | 1.2-12° | — | — |
| β hybrid-β PSI | 0.4° | 7.2-7.8° | 2.0-11° | 1.8-9.2° | 18-27° | 5.0-8.3° |
| β PSI-β I-EGF1 | 0.8° | — | 3.4-13° | 5.7-18° | 5.5-40° | 5.5-41° |
| β hybrid-β I-EGF1 | 0.5° | — | 6.8-23° | 11-26° | 29-51° | 3.7-46° |
| β I-EGF1-β I-EGF2 | 0.4° | — | — | — | 140-170° | 67° |
| β I-EGF2-β I-EGF3 | 1.2° | — | — | — | 8.4-8.5° | — |
| β I-EGF3-β I-EGF4 | 2.3° | 5.4-7.2° | — | — | — | — |
| β I-EGF4-β ankle | 1.2° | 10-11° | — | — | — | — |
| β I-ankle-β TD | 46°[h] | 18°[i] | — | — | — | — |
| α β-propeller-β I | 0.2° | 3.0-3.3° | 1.7-2.8° | 0.6-1.1° | — | — |

[a]Each pair of domains from two molecules were superposed using the first domain, and the change in angle upon superimposing the second domain was calculated. Dashes indicate where no comparison is possible, because only one or no domain pairs are available.
[b]Two molecules in current structure (1 × 1).
[c]Two molecules in current structure versus PDB code 1U8C (2 × 1).
[d]Two molecules in current structure versus PDB 2VDR and three molecules in PDB 1TYE (2 × 4).
[e]Comparisons among 2VDR and three molecules in 1TYE (3 × 4/2).
[f]Two molecules in current structure, and PDB 1U8C versus PDB 1YUK, PDB 2P26, and PDB 2P28 (3 × 3 to 3 × 1, depending on fragment length).
[g]comparisons among PDB 1YUK, 2P26, and 2P28 (3 to 1 comparisons depending on fragment length).
[h]Residues common to molecules 1 and 2 in βTD are used, 606-612
[i]$\alpha_{IIb}\beta_3$ molecule 1 compared to $\alpha_V\beta_3$

TABLE 3

αXβ2-GCG constructs prepared to investigate the clasping of C-terminal region of ectodomain.
Table discloses SEQ ID NOS 70-81, respectively, in order of appearance.

| | wild alphaX | resid # | alpha clasp1 | alpha clasp2 | alpha clasp3 | alpha clasp4 | alpha clasp5 | | resid # | beta clasp1 | beta clasp2 | beta clasp3 | beta clasp4 | beta clasp5 | wild beta2 | |
|---|---|---|---|---|---|---|---|---|---|---|---|---|---|---|---|---|
| Calf-2 | E | 1079 | E | E | E | E | E | | | | | | | | | βTD |
| | K | 1080 | K | K | K | K | K | | 672 | E | E | E | E | E | E | |
| | Y | 1081 | Y | Y | Y | Y | Y | | 673 | C | C | C | C | C | C | |
| | K | 1082 | G | K | K | K | K | | 674 | G | V | V | V | V | V | |
| | V | 1083 | | G | V | V | V | | 675 | | G | A | A | A | A | |
| | H | 1084 | G | | G | H | H | | 676 | G | | G | G | G | G | |
| | N(g)* | 1085 | Precission-C-H (PCH) | G | | G | N | | 677 | (PCH) | G | | G | P | P | |
| | P(c)* | 1086 | | (PCH) | G | | G | | 678 | | (PCH) | G | | G | N(d)* | |
| | T(g)* | 1087 | | | (PCH) | G | | | 679 | | | (PCH) | G | | I(g)* | Trans-membrane |
| | P | 1088 | | | | (PCH) | G | | 680 | | | | (PCH) | G | A(c)* | |
| Trans-membrane | L | 1089 | | | | | (PCH) | | 681 | | | | | (PCH) | A(g)* | |
| | I | 1090 | | | | | | | | | | | | | | |

Residues changed to Cys are always both preceded and followed by Gly to introduce local flexibility to Cys.
*Clasping sequence of crystallized αXβ2-GCG-TCSH construct are shown on wild type sequence as red and asterisked.

TABLE 4

| | | Constitutive disulfide[b] | | | Redox buffer treat. | | Cu-Ph oxidation/ intact call | |
|---|---|---|---|---|---|---|---|---|
| αIIbβ3 | | | | Av- | | Av- | | Av- |
| alpha | beta | Exp1 | Ex2 | erage | Exp1 | Exp2 | erage | Exp1 | erage |
| R957 | E686 | 28 | | 28 | 0 | | 0 | | |
| R957 | C687 | 2 | | 2 | | | | | |
| R957 | P688 | 95 | 82 | 88.5 | | | | | |
| R957 | G690 | 15 | | 15 | | | | | |
| R957 | P691 | 10 | | 10 | | | | | |
| R957 | D692 | 12 | | 12 | | | | | |
| A958 | E686 | 100 | | 100 | 54 | | 54 | | |
| A958 | C687 | 2 | | 2 | | | | | |

TABLE 4-continued

| αIIbβ3 | | Constitutive disulfideb | | | Redox buffer treat. | | | Cu-Ph oxidation/ intact call | |
|---|---|---|---|---|---|---|---|---|---|
| alpha | beta | Exp1 | Ex2 | Average | Exp1 | Exp2 | Average | Exp1 | Average |
| A958 | P688 | 96 | | 96 | | | | | |
| A958 | G690 | 12 | | 12 | | | | | |
| A958 | P691 | 15 | | 15 | | | | | |
| A958 | D692 | 8 | | 8 | | | | | |
| L959 | E686 | 94 | | 94 | | | | | |
| L959 | C687 | 2 | | 2 | | | | | |
| L959 | P688 | 98 | | 98 | 100 | | 100 | | |
| L959 | G690 | 30 | | 30 | | | | | |
| L959 | P691 | 12 | | 12 | | | | | |
| L959 | D692 | 2 | | 2 | | | | | |
| E960 | E686 | 92 | | 92 | 59 | | 59 | | |
| E960 | C687 | 3 | | 3 | | | | | |
| E960 | P688 | 91 | | 91 | 98 | | 98 | | |
| E960 | G690 | 77 | | 77 | | | | | |
| E960 | P691 | 64 | | 64 | | | | | |
| E960 | D692 | 15 | | 15 | | | | | |
| R962 | P691 | 100 | | 100 | 56 | | 56 | 100 | 100 |
| R962 | D692 | 67 | | 67 | 5 | 5 | 5 | 72 | 72 |
| R962 | I693 | 77 | | 77 | 3 | 3 | 3 | 82 | 82 |
| R962 | L694 | 8 | | 8 | 0 | 0 | 0 | 6 | 6 |
| R962 | V695 | 0 | | 0 | 0 | 0 | 0 | 0 | 0 |
| R962 | V696 | 0 | | 0 | 0 | 0 | 0 | 0 | 0 |
| R962 | L697 | 0 | | 0 | 0 | 0 | 0 | 0 | 0 |
| A963 | P691 | 100 | | 100 | 30 | 38 | 34 | 100 | 100 |
| A963 | D692 | 41 | | 41 | 2 | 5 | 3.5 | 44 | 44 |
| A963 | I693 | 100 | | 100 | 19 | 24 | 21.5 | 100 | 100 |
| A963 | L694 | 5 | | 5 | 0 | 0 | 0 | 13 | 13 |
| A963 | V695 | | | | 1 | 1 | 1 | 3 | 3 |
| A963 | V696 | | | | 0 | 2 | 1 | 13 | 13 |
| A963 | L697 | | | | 1 | 0 | 0.5 | 6 | 6 |
| I964 | P691 | 60 | | 60 | 61 | 54 | 57.5 | 59 | 59 |
| I964 | D692 | 77 | | 77 | 21 | 19 | 20 | 80 | 80 |
| I964 | I693 | 74 | | 74 | 90 | 89 | 89.5 | 92 | 92 |
| I964 | L694 | 33 | | 33 | 5 | 8 | 6.5 | 35 | 35 |
| I964 | V695 | 18 | | 18 | 4 | 6 | 5 | 16 | 16 |
| I964 | V696 | 31 | | 31 | 30 | 54 | 42 | 39 | 39 |
| I964 | L697 | 6 | | 6 | 5 | 6 | 5.5 | 6 | 6 |
| I964 | L698 | 0 | | 0 | 0 | 0 | 0 | 0 | 0 |

Values are % disulfide bond formation

TABLE 5

052504 FACS (LFA-1 disulfide mutants on 293T cell)

| | Sample No | Sample description | | X63 | Mean | | | | |
|---|---|---|---|---|---|---|---|---|---|
| | | | | | MHM24 | m24 | A03 | KIM127 (1) | KIM127 (2) |
| 5A | mock | — | — | | 6.34 | 6.17 | 6.27 | 6.79 | 5.54 |
| | #2 | E1061C | G676C | | 97.38 | 35.81 | 59.26 | 8.27 | 9.59 |
| | #3 | K1062C | G676C | | 117.13 | 57.43 | 67.16 | 11.14 | 15.81 |
| | #4 | Q1063C | G676C | | 95.90 | 47.81 | 61.04 | 12.12 | 12.15 |
| | #5 | K1062C | P677C | | 102.18 | 43.50 | 58.30 | 10.26 | 9.36 |
| | #6 | Q1063C | P677C | | 116.87 | 52.29 | 72.99 | 10.89 | 14.43 |
| | #7 | M1064C | P677C | | 125.86 | 52.95 | 77.00 | 10.77 | 11.85 |
| | #8 | Q1063C | N678C | | 88.46 | 38.63 | 52.54 | 8.54 | 12.25 |
| | #9 | M1064C | N678C | 4.06 | 147.12 | 57.10 | 88.01 | 10.03 | 12.09 |
| | WT | WT | WT | 5.96 | 158.96 | 66.32 | 105.85 | 12.15 | 13.91 |

Normalization

Mean value normalized with expression level (MHM24)

| | Sample No | Sample description | | X63 | MHM24 | m24 | A03 | KIM127 (1) | KIM127 (2) |
|---|---|---|---|---|---|---|---|---|---|
| 5B | mock | — | — | | 6.34 | — | — | — | — |
| | #2 | E1061C | G676C | | 97.38 | 0.33 | 0.58 | 0.016 | 0.044 |
| | #3 | K1062C | G676C | | 117.13 | 0.46 | 0.55 | 0.039 | 0.093 |
| | #4 | Q1063C | G676C | | 95.90 | 0.46 | 0.61 | 0.060 | 0.074 |
| | #5 | K1062C | P677C | | 102.18 | 0.39 | 0.54 | 0.036 | 0.040 |
| | #6 | Q1063C | P677C | | 116.87 | 0.42 | 0.60 | 0.037 | 0.080 |
| | #7 | M1064C | P677C | | 125.86 | 0.39 | 0.59 | 0.033 | 0.053 |
| | #8 | Q1063C | N678C | | 88.46 | 0.40 | 0.56 | 0.021 | 0.082 |
| | #9 | M1064C | N678C | 4.06 | 147.12 | 0.36 | 0.58 | 0.023 | 0.047 |
| | WT | WT | WT | 5.96 | 158.96 | 0.39 | 0.65 | 0.035 | 0.055 |

Normalization (WT is set to 1.0)

Relative to wild-type

| | Sample No | Sample description | | X63 | MHM24 | m24 | A03 | KIM127 (1) | KIM127 (2) |
|---|---|---|---|---|---|---|---|---|---|
| 5C | mock | — | — | | 6.34 | — | — | — | — |
| | #2 | E1061C | G676C | | 97.38 | 0.83 | 0.89 | 0.46 | 0.81 |
| | #3 | K1062C | G676C | | 117.13 | 1.17 | 0.84 | 1.12 | 1.69 |
| | #4 | Q1063C | G676C | | 95.90 | 1.18 | 0.94 | 1.69 | 1.35 |
| | #5 | K1062C | P677C | | 102.18 | 0.99 | 0.83 | 1.03 | 0.73 |
| | #6 | Q1063C | P677C | | 116.87 | 1.06 | 0.93 | 1.06 | 1.47 |
| | #7 | M1064C | P677C | | 125.86 | 0.99 | 0.91 | 0.95 | 0.96 |

TABLE 5-continued

|  |  |  |  |  |  |  |  |  |
|---|---|---|---|---|---|---|---|---|
| #8 | Q1063C | N678C |  | 88.46 | 1.00 | 0.86 | 0.61 | 1.49 |
| #9 | M1064C | N678C | 4.06 | 147.12 | 0.92 | 0.89 | 0.66 | 0.85 |
| WT | WT | WT | 5.96 | 158.96 | 1.00 | 1.00 | 1.00 | 1.00 |

Summary of WB and FACS result

|  |  |  | Relative to wild-type | | | | |
|---|---|---|---|---|---|---|---|
| Sample No | Sample description | disulfide | Expressio | m24 | A03 | KIM127 (1) | KIM127 (2) |
| 5D mock | — | — | − | − | — | — | — | — |
| #2 | E1061C | G676C | ++ | ++ | 0.83 | 0.89 | 0.46 | 0.81 |
| #3 | K1062C | G676C | ++ | ++ | 1.17 | 0.84 | 1.12 | 1.69 |
| #4 | Q1063C | G676C | + | ++ | 1.18 | 0.94 | 1.69 | 1.35 |
| #5 | K1062C | P677C | ++ | ++ | 0.99 | 0.83 | 1.03 | 0.73 |
| #6 | Q1063C | P677C | ++ | +++ | 1.06 | 0.93 | 1.06 | 1.47 |
| #7 | M1064C | P677C | ++ | +++ | 0.99 | 0.91 | 0.95 | 0.96 |
| #8 | Q1063C | N678C |  | ++ | 1.00 | 0.86 | 0.61 | 1.49 |
| #9 | M1064C | N678C | + | +++ | 0.92 | 0.89 | 0.66 | 0.85 |
| WT | WT | WT | − | +++ | 1.00 | 1.00 | 1.00 | 1.00 |

Summary of RB result

|  |  | ve to wild-type | |
|---|---|---|---|
| Sample No | Sample description | disulfide | Expression |
| 5E mock | — | — | − | − |
| #2 | E1061C | G676C | ++ | ++ |
| #3 | K1062C | G676C | ++ | ++ |

The invention claimed is:

1. An integrin polypeptide composition comprising a modified integrin polypeptide locked in a closed conformation comprising one extracellular alpha and one extracellular beta subunit wherein the alpha subunit comprises human integrin αIIb N terminal extracellular domain L959C mutant set forth in SEQ ID NO:48 or human integrin αIIb N terminal extracellular domain E960C mutant set forth in SEQ ID NO: 49, and wherein the beta subunit comprises human integrin β3 N terminal extracellular domain V664C mutant set forth in SEQ ID NO: 52 or human integrin β3 N terminal extracellular domain P688C mutant set forth in SEQ ID NO: 53.

2. The integrin polypeptide of claim 1, wherein the human integrin is human platelet integrin.

3. An integrin polypeptide composition comprising a modified integrin polypeptide locked in a closed conformation comprising a modified αIIb comprising SEQ ID NO: 48 and a modified β3 comprising SEQ ID NO: 53.

* * * * *

SEQUENCE LISTING

<160> NUMBER OF SEQ ID NOS: 105

<210> SEQ ID NO 1
<211> LENGTH: 159
<212> TYPE: PRT
<213> ORGANISM: Homo sapiens

<400> SEQUENCE: 1

Arg Asp Leu Ala Leu Ser Glu Gly Asp Ile His Thr Leu Gly Cys Gly
1               5                   10                  15

Val Ala Gln Cys Leu Lys Ile Val Cys Gln Val Gly Arg Leu Asp Arg
            20                  25                  30

Gly Lys Ser Ala Ile Leu Tyr Val Lys Ser Leu Leu Trp Thr Glu Thr
        35                  40                  45

Phe Met Asn Lys Glu Asn Gln Asn His Ser Tyr Ser Leu Lys Ser Ser
50                  55                  60

Ala Ser Phe Asn Val Ile Glu Phe Pro Tyr Lys Asn Leu Pro Ile Glu
65                  70                  75                  80

Asp Ile Thr Asn Ser Thr Leu Val Thr Thr Asn Val Thr Trp Gly Ile
                85                  90                  95

Gln Pro Ala Pro Met Pro Val Pro Val Trp Val Ile Ile Leu Ala Val
            100                 105                 110

Leu Ala Gly Leu Leu Leu Leu Ala Val Leu Val Phe Val Met Tyr Arg
        115                 120                 125

Met Gly Phe Phe Lys Arg Val Arg Pro Pro Gln Glu Glu Gln Glu Arg
130                 135                 140

Glu Gln Leu Gln Pro His Glu Asn Gly Glu Gly Asn Ser Glu Thr
145                 150                 155

<210> SEQ ID NO 2
<211> LENGTH: 159

<212> TYPE: PRT
<213> ORGANISM: Mus musculus

<400> SEQUENCE: 2

Arg Gly Leu Thr Leu Arg Glu Gly Asp Val His Thr Leu Gly Cys Gly
1               5                   10                  15

Ile Ala Lys Cys Leu Gln Ile Thr Cys Gln Val Gly Arg Leu Asp Arg
                20                  25                  30

Gly Lys Ser Ala Ile Leu Tyr Val Lys Ser Leu Leu Trp Thr Glu Thr
            35                  40                  45

Phe Met Asn Lys Glu Asn Gln Asn His Ser Tyr Ser Leu Lys Ser Ser
    50                  55                  60

Ala Ser Phe Asn Ile Ile Glu Phe Pro Tyr Lys Asn Leu Pro Ile Glu
65                  70                  75                  80

Asp Leu Phe Asn Ser Thr Leu Val Thr Thr Asn Ile Thr Trp Gly Ile
                85                  90                  95

Gln Pro Ala Pro Met Pro Val Pro Val Trp Val Ile Ile Leu Ala Val
            100                 105                 110

Leu Ala Gly Leu Leu Leu Leu Ala Val Leu Val Phe Val Met Tyr Arg
        115                 120                 125

Met Gly Phe Phe Lys Arg Val Arg Pro Pro Gln Glu Glu Gln Glu Arg
    130                 135                 140

Glu Gln Leu Gln Pro His Glu Asn Gly Glu Gly Asn Ser Glu Thr
145                 150                 155

<210> SEQ ID NO 3
<211> LENGTH: 153
<212> TYPE: PRT
<213> ORGANISM: Homo sapiens

<400> SEQUENCE: 3

Pro Ser Arg Ser Ser Ala Ser Ser Gly Pro Gln Ile Leu Lys Cys Pro
1               5                   10                  15

Glu Ala Glu Cys Phe Arg Leu Arg Cys Glu Leu Gly Pro Leu His Gln
                20                  25                  30

Gln Glu Ser Gln Ser Leu Gln Leu His Phe Arg Val Trp Ala Lys Thr
            35                  40                  45

Phe Leu Gln Arg Glu His Gln Pro Phe Ser Leu Gln Cys Glu Ala Val
    50                  55                  60

Tyr Lys Ala Leu Lys Met Pro Tyr Arg Ile Leu Pro Arg Gln Leu Pro
65                  70                  75                  80

Gln Lys Glu Arg Gln Val Ala Thr Ala Val Gln Trp Thr Lys Ala Glu
                85                  90                  95

Gly Ser Tyr Gly Val Pro Leu Trp Ile Ile Ile Leu Ala Ile Leu Phe
            100                 105                 110

Gly Leu Leu Leu Leu Gly Leu Leu Ile Tyr Ile Leu Tyr Lys Leu Gly
        115                 120                 125

Phe Phe Lys Arg Ser Leu Pro Tyr Gly Thr Ala Met Glu Lys Ala Gln
    130                 135                 140

Leu Lys Pro Pro Ala Thr Ser Asp Ala
145                 150

<210> SEQ ID NO 4
<211> LENGTH: 153
<212> TYPE: PRT
<213> ORGANISM: Mus musculus

<400> SEQUENCE: 4

```
Pro Gly Arg Ser Ser Thr Ala Ser Gly Thr Gln Val Leu Lys Cys Pro
1               5                   10                  15

Glu Ala Lys Cys Phe Arg Leu Arg Cys Glu Phe Gly Pro Leu His Arg
            20                  25                  30

Gln Glu Ser Arg Ser Leu Gln Leu His Phe Arg Val Trp Ala Lys Thr
        35                  40                  45

Phe Leu Gln Arg Glu Tyr Gln Pro Phe Ser Leu Gln Cys Glu Ala Val
    50                  55                  60

Tyr Glu Ala Leu Lys Met Pro Tyr Gln Ile Leu Pro Arg Gln Leu Pro
65                  70                  75                  80

Gln Lys Lys Leu Gln Val Ala Thr Ala Val Gln Trp Thr Lys Ala Glu
                85                  90                  95

Gly Ser Asn Gly Val Pro Leu Trp Ile Ile Leu Ala Ile Leu Phe
            100                 105                 110

Gly Leu Leu Leu Leu Gly Leu Leu Ile Tyr Val Leu Tyr Lys Leu Gly
            115                 120                 125

Phe Phe Lys Arg Ser Leu Pro Tyr Gly Thr Ala Met Glu Lys Ala Gln
    130                 135                 140

Leu Lys Pro Pro Ala Thr Ser Asp Ala
145                 150
```

<210> SEQ ID NO 5
<211> LENGTH: 143
<212> TYPE: PRT
<213> ORGANISM: Homo sapiens

<400> SEQUENCE: 5

```
Pro Glu Gln Pro Ser Arg Leu Gln Asp Pro Val Leu Val Ser Cys Asp
1               5                   10                  15

Ser Ala Pro Cys Thr Val Val Gln Cys Asp Leu Gln Glu Met Ala Arg
            20                  25                  30

Gly Gln Arg Ala Met Val Thr Val Leu Ala Phe Leu Trp Leu Pro Ser
        35                  40                  45

Leu Tyr Gln Arg Pro Leu Asp Gln Phe Val Leu Gln Ser His Ala Trp
    50                  55                  60

Phe Asn Val Ser Ser Leu Pro Tyr Ala Val Pro Pro Leu Ser Leu Pro
65                  70                  75                  80

Arg Gly Glu Ala Gln Val Trp Thr Gln Leu Leu Arg Ala Leu Glu Glu
                85                  90                  95

Arg Ala Ile Pro Ile Trp Trp Val Leu Val Gly Val Leu Gly Gly Leu
            100                 105                 110

Leu Leu Leu Thr Ile Leu Val Leu Ala Met Trp Lys Val Gly Phe Phe
            115                 120                 125

Lys Arg Asn Arg Pro Pro Leu Glu Glu Asp Asp Glu Glu Gly Glu
    130                 135                 140
```

<210> SEQ ID NO 6
<211> LENGTH: 143
<212> TYPE: PRT
<213> ORGANISM: Mus musculus

<400> SEQUENCE: 6

```
Gln Gly Pro Lys Pro Gly Gln Gln Asp Pro Val Leu Val Ser Cys Asp
1               5                   10                  15

Gly Ser Ala Ser Cys Thr Val Val Glu Cys Glu Leu Arg Glu Met Val
```

```
            20                  25                  30
Arg Gly Gln Arg Ala Met Val Thr Val Gln Ala Met Leu Gly Leu Ser
        35                  40                  45

Ser Leu Arg Gln Arg Pro Gln Glu Gln Phe Val Leu Gln Ser His Ala
 50                  55                  60

Trp Phe Asn Val Ser Ser Leu Pro Tyr Ser Val Pro Val Val Ser Leu
 65                  70                  75                  80

Pro Ser Gly Gln Ala Arg Val Gln Thr Gln Leu Leu Arg Ala Leu Glu
                 85                  90                  95

Glu Arg Ala Ile Pro Val Trp Trp Val Leu Val Gly Val Leu Gly Gly
                100                 105                 110

Leu Leu Leu Leu Thr Leu Leu Val Leu Ala Met Trp Lys Ala Gly Phe
            115                 120                 125

Phe Lys Arg Asn Arg Pro Pro Leu Glu Glu Asp Glu Glu Glu Glu
        130                 135                 140
```

<210> SEQ ID NO 7
<211> LENGTH: 159
<212> TYPE: PRT
<213> ORGANISM: Homo sapiens

<400> SEQUENCE: 7

```
Lys Arg Asp Val His Val Val Glu Phe His Arg Gln Ser Pro Ala Lys
 1               5                  10                  15

Ile Leu Asn Cys Thr Asn Ile Glu Cys Leu Gln Ile Ser Cys Ala Val
                 20                  25                  30

Gly Arg Leu Glu Gly Gly Glu Ser Ala Val Leu Lys Val Arg Ser Arg
             35                  40                  45

Leu Trp Ala His Thr Phe Leu Gln Arg Lys Asn Asp Pro Tyr Ala Leu
 50                  55                  60

Ala Ser Leu Val Ser Phe Glu Val Lys Lys Met Pro Tyr Thr Asp Gln
 65                  70                  75                  80

Pro Ala Lys Leu Pro Glu Gly Ser Ile Ala Ile Lys Thr Ser Val Ile
                 85                  90                  95

Trp Ala Thr Pro Asn Val Ser Phe Ser Ile Pro Leu Trp Val Ile Ile
                100                 105                 110

Leu Ala Ile Leu Leu Gly Leu Leu Val Leu Ala Ile Leu Thr Leu Ala
            115                 120                 125

Leu Trp Lys Cys Gly Phe Phe Asp Arg Ala Arg Pro Pro Gln Glu Asp
        130                 135                 140

Met Thr Asp Arg Glu Gln Leu Thr Asn Asp Lys Thr Pro Glu Ala
145                 150                 155
```

<210> SEQ ID NO 8
<211> LENGTH: 156
<212> TYPE: PRT
<213> ORGANISM: Homo sapiens

<400> SEQUENCE: 8

```
Phe Ala Glu Arg Lys Tyr Gln Thr Leu Asn Cys Ser Val Asn Val Asn
 1               5                  10                  15

Cys Val Asn Ile Arg Cys Pro Leu Arg Gly Leu Asp Ser Lys Ala Ser
                 20                  25                  30

Leu Ile Leu Arg Ser Arg Leu Trp Asn Ser Thr Phe Leu Glu Glu Tyr
             35                  40                  45

Ser Lys Leu Asn Tyr Leu Asp Ile Leu Met Arg Ala Phe Ile Asp Val
```

```
Thr Ala Ala Ala Glu Asn Ile Arg Leu Pro Asn Ala Gly Thr Gln Val
65                  70                  75                  80

Arg Val Thr Val Phe Pro Ser Lys Thr Val Ala Gln Tyr Ser Gly Val
                85                  90                  95

Pro Trp Trp Ile Ile Leu Val Ala Ile Leu Ala Gly Ile Leu Met Leu
            100                 105                 110

Ala Leu Leu Val Phe Ile Leu Trp Lys Cys Gly Phe Phe Lys Arg Asn
        115                 120                 125

Lys Lys Asp His Tyr Asp Ala Thr Tyr His Lys Ala Glu Ile His Ala
    130                 135                 140

Gln Pro Ser Asp Lys Glu Arg Leu Thr Ser Asp Ala
145                 150                 155

<210> SEQ ID NO 9
<211> LENGTH: 156
<212> TYPE: PRT
<213> ORGANISM: Mus musculus

<400> SEQUENCE: 9

Phe Pro Glu Arg Lys Tyr Gln Thr Leu Asn Cys Ser Val Asn Val Arg
1               5                   10                  15

Cys Val Asn Ile Arg Cys Pro Leu Arg Gly Leu Asp Thr Lys Ala Ser
            20                  25                  30

Leu Val Leu Cys Ser Arg Leu Trp Asn Ser Thr Phe Leu Glu Glu Tyr
        35                  40                  45

Ser Lys Leu Asn Tyr Leu Asp Ile Leu Val Arg Ala Ser Ile Asp Val
    50                  55                  60

Thr Ala Ala Gln Asn Ile Lys Leu Pro His Ala Gly Thr Gln Val
65                  70                  75                  80

Arg Val Thr Val Phe Pro Ser Lys Thr Val Ala Gln Tyr Ser Gly Val
                85                  90                  95

Ala Trp Trp Ile Ile Leu Leu Ala Val Leu Ala Gly Ile Leu Met Leu
            100                 105                 110

Ala Leu Leu Val Phe Leu Leu Trp Lys Cys Gly Phe Phe Lys Arg Asn
        115                 120                 125

Lys Lys Asp His Tyr Asp Ala Thr Tyr His Lys Ala Glu Ile His Thr
    130                 135                 140

Gln Pro Ser Asp Lys Glu Arg Leu Thr Ser Asp Ala
145                 150                 155

<210> SEQ ID NO 10
<211> LENGTH: 203
<212> TYPE: PRT
<213> ORGANISM: Homo sapiens

<400> SEQUENCE: 10

Trp Pro Val Ser Ser Ala Glu Lys Lys Asn Ile Thr Leu Asp Cys
1               5                   10                  15

Ala Arg Gly Thr Ala Asn Cys Val Val Phe Ser Cys Pro Leu Tyr Ser
            20                  25                  30

Phe Asp Arg Ala Ala Val Leu His Val Trp Gly Arg Leu Trp Asn Ser
        35                  40                  45

Thr Phe Leu Glu Glu Tyr Ser Ala Val Lys Ser Leu Glu Val Ile Val
    50                  55                  60

Arg Ala Asn Ile Thr Val Lys Ser Ser Ile Lys Asn Leu Met Leu Arg
```

```
              65                  70                  75                  80
Asp Ala Ser Thr Val Ile Pro Val Met Val Tyr Leu Asp Pro Met Ala
                85                  90                  95

Val Val Ala Glu Gly Val Pro Trp Trp Val Ile Leu Leu Ala Val Leu
            100                 105                 110

Ala Gly Leu Leu Val Leu Ala Leu Val Leu Leu Trp Lys Met
        115                 120                 125

Gly Phe Phe Lys Arg Ala Lys His Pro Glu Ala Thr Val Pro Gln Tyr
    130                 135                 140

His Ala Val Lys Ile Pro Arg Glu Asp Arg Gln Gln Phe Lys Glu Glu
145                 150                 155                 160

Lys Thr Gly Thr Ile Leu Arg Asn Asn Trp Gly Ser Pro Arg Arg Glu
                165                 170                 175

Gly Pro Asp Ala His Pro Ile Leu Ala Ala Asp Gly His Pro Glu Leu
            180                 185                 190

Gly Pro Asp Gly His Pro Gly Pro Gly Thr Ala
        195                 200
```

<210> SEQ ID NO 11
<211> LENGTH: 202
<212> TYPE: PRT
<213> ORGANISM: Mus musculus

<400> SEQUENCE: 11

```
Trp Pro Val Ser Ser Ala Glu Lys Arg Asn Val Thr Leu Asp Cys Ala
1               5                   10                  15

Gln Gly Thr Ala Lys Cys Val Val Phe Ser Cys Pro Leu Tyr Ser Phe
            20                  25                  30

Asp Arg Ala Ala Val Leu His Val Trp Gly Arg Leu Trp Asn Ser Thr
        35                  40                  45

Phe Leu Glu Glu Tyr Met Ala Val Lys Ser Leu Glu Val Ile Val Arg
    50                  55                  60

Ala Asn Ile Thr Val Lys Ser Ser Ile Lys Asn Leu Leu Leu Arg Asp
65                  70                  75                  80

Ala Ser Thr Val Ile Pro Val Met Val Tyr Leu Asp Pro Met Ala Val
                85                  90                  95

Val Val Glu Gly Val Pro Trp Trp Val Ile Leu Leu Ala Val Leu Ala
            100                 105                 110

Gly Leu Leu Val Leu Ala Leu Val Leu Leu Trp Lys Leu Gly
        115                 120                 125

Phe Phe Lys Arg Ala Lys His Pro Glu Ala Thr Val Pro Gln Tyr His
    130                 135                 140

Ala Val Lys Ile Pro Arg Glu Asp Arg Gln Gln Phe Lys Glu Lys
145                 150                 155                 160

Thr Gly Thr Ile Gln Arg Ser Asn Trp Gly Asn Ser Gln Trp Glu Gly
                165                 170                 175

Ser Asp Ala His Pro Ile Leu Ala Ala Asp Trp His Pro Glu Leu Gly
            180                 185                 190

Pro Asp Gly His Pro Val Pro Ala Thr Ala
        195                 200
```

<210> SEQ ID NO 12
<211> LENGTH: 202
<212> TYPE: PRT
<213> ORGANISM: Mus musculus

<400> SEQUENCE: 12

Trp Pro Val Ser Ser Ala Glu Lys Arg Asn Val Thr Leu Asp Cys Ala
1               5                   10                  15

Gln Gly Thr Ala Lys Cys Val Val Phe Ser Cys Pro Leu Tyr Ser Phe
                20                  25                  30

Asp Arg Ala Ala Val Leu His Val Trp Gly Arg Leu Trp Asn Ser Thr
            35                  40                  45

Phe Leu Glu Glu Tyr Met Ala Val Lys Ser Leu Glu Val Ile Val Arg
50                  55                  60

Ala Asn Ile Thr Val Lys Ser Ser Ile Lys Asn Leu Leu Leu Arg Asp
65                  70                  75                  80

Ala Ser Thr Val Ile Pro Val Met Val Tyr Leu Asp Pro Met Ala Val
                85                  90                  95

Val Val Glu Gly Val Pro Trp Trp Val Ile Leu Ala Val Leu Ala
                100                 105                 110

Gly Leu Leu Val Leu Ala Leu Leu Val Leu Leu Trp Lys Leu Gly
                115                 120                 125

Phe Phe Lys Arg Ala Lys His Pro Glu Ala Thr Val Pro Gln Tyr His
130                 135                 140

Ala Val Lys Ile Pro Arg Glu Asp Arg Gln Gln Phe Lys Glu Glu Lys
145                 150                 155                 160

Thr Gly Thr Ile Gln Arg Ser Asn Trp Gly Asn Ser Gln Trp Glu Gly
                165                 170                 175

Ser Asp Ala His Pro Ile Leu Ala Ala Asp Trp His Pro Glu Leu Gly
                180                 185                 190

Pro Asp Gly His Pro Val Pro Ala Thr Ala
                195                 200

<210> SEQ ID NO 13
<211> LENGTH: 162
<212> TYPE: PRT
<213> ORGANISM: Homo sapiens

<400> SEQUENCE: 13

Leu Ala Ala Ala Lys Lys Ala Lys Ser Glu Thr Val Leu Thr Cys Ala
1               5                   10                  15

Thr Gly Arg Ala His Cys Val Trp Leu Glu Cys Pro Ile Pro Asp Ala
                20                  25                  30

Pro Val Val Thr Asn Val Thr Val Lys Ala Arg Val Trp Asn Ser Thr
                35                  40                  45

Phe Ile Glu Asp Tyr Arg Asp Phe Asp Arg Val Arg Val Asn Gly Trp
50                  55                  60

Ala Thr Leu Phe Leu Arg Thr Ser Ile Pro Thr Ile Asn Met Glu Asn
65                  70                  75                  80

Lys Thr Thr Trp Phe Ser Val Asp Ile Asp Ser Glu Leu Val Glu Glu
                85                  90                  95

Leu Pro Ala Glu Ile Glu Leu Trp Leu Val Leu Val Ala Val Gly Ala
                100                 105                 110

Gly Leu Leu Leu Leu Gly Leu Ile Ile Leu Leu Leu Trp Lys Cys Gly
                115                 120                 125

Phe Phe Lys Arg Ala Arg Thr Arg Ala Leu Tyr Glu Ala Lys Arg Gln
130                 135                 140

Lys Ala Glu Met Lys Ser Gln Pro Ser Glu Thr Glu Arg Leu Thr Asp
145                 150                 155                 160

Asp Tyr

<210> SEQ ID NO 14
<211> LENGTH: 162
<212> TYPE: PRT
<213> ORGANISM: Mus musculus

<400> SEQUENCE: 14

```
Leu Ala Ala Ala Lys Ala Lys Ser Glu Thr Val Leu Thr Cys Ser
1               5                   10                  15

Asn Gly Arg Ala Arg Cys Val Trp Leu Glu Cys Pro Leu Pro Asp Thr
            20                  25                  30

Ser Asn Ile Thr Asn Val Thr Val Lys Ala Arg Val Trp Asn Ser Thr
        35                  40                  45

Phe Ile Glu Asp Tyr Lys Asp Phe Asp Arg Val Arg Val Asp Gly Trp
    50                  55                  60

Ala Thr Leu Phe Leu Arg Thr Ser Ile Pro Thr Ile Asn Met Glu Asn
65                  70                  75                  80

Lys Thr Thr Trp Phe Ser Val Asp Ile Asp Ser Glu Leu Val Glu Glu
                85                  90                  95

Leu Pro Ala Glu Ile Glu Leu Trp Leu Val Leu Val Ala Val Gly Ala
            100                 105                 110

Gly Leu Leu Leu Leu Gly Leu Ile Ile Leu Leu Leu Trp Lys Cys Gly
        115                 120                 125

Phe Phe Lys Arg Ala Arg Thr Arg Ala Leu Tyr Glu Ala Lys Arg Gln
    130                 135                 140

Lys Ala Glu Met Lys Ser Gln Pro Ser Glu Thr Glu Arg Leu Thr Asp
145                 150                 155                 160

Asp Tyr
```

<210> SEQ ID NO 15
<211> LENGTH: 154
<212> TYPE: PRT
<213> ORGANISM: Homo sapiens

<400> SEQUENCE: 15

```
Phe Leu Ser Lys Thr Asp Lys Arg Leu Leu Tyr Cys Ile Lys Ala Asp
1               5                   10                  15

Pro His Cys Leu Asn Phe Leu Cys Asn Phe Gly Lys Met Glu Ser Gly
            20                  25                  30

Lys Glu Ala Ser Val His Ile Gln Leu Glu Gly Arg Pro Ser Ile Leu
        35                  40                  45

Glu Met Asp Glu Thr Ser Ala Leu Lys Phe Glu Ile Arg Ala Thr Gly
    50                  55                  60

Phe Pro Glu Pro Asn Pro Arg Val Ile Glu Leu Asn Lys Asp Glu Asn
65                  70                  75                  80

Val Ala His Val Leu Leu Glu Gly Leu His His Gln Arg Pro Lys Arg
                85                  90                  95

Tyr Phe Thr Ile Val Ile Ile Ser Ser Ser Leu Leu Leu Gly Leu Ile
            100                 105                 110

Val Leu Leu Leu Ile Ser Tyr Val Met Trp Lys Ala Gly Phe Phe Lys
        115                 120                 125

Arg Gln Tyr Lys Ser Ile Leu Gln Glu Glu Asn Arg Arg Asp Ser Trp
    130                 135                 140

Ser Tyr Ile Asn Ser Lys Ser Asn Asp Asp
145                 150
```

<210> SEQ ID NO 16
<211> LENGTH: 154
<212> TYPE: PRT
<213> ORGANISM: Mus musculus

<400> SEQUENCE: 16

Phe Leu Ser Lys Thr Asp Lys Arg Leu Leu Tyr Cys Met Lys Ala Asp
1               5                   10                  15

Gln His Cys Leu Asp Phe Leu Cys Asn Phe Gly Lys Met Glu Ser Gly
            20                  25                  30

Lys Glu Ala Ser Val His Ile Gln Leu Glu Gly Arg Pro Ser Ile Leu
        35                  40                  45

Glu Met Asp Glu Thr Ser Ser Leu Lys Phe Glu Ile Lys Ala Thr Ala
    50                  55                  60

Phe Pro Glu Pro His Pro Lys Val Ile Glu Leu Asn Lys Asp Glu Asn
65                  70                  75                  80

Val Ala His Val Phe Leu Glu Gly Leu His His Gln Arg Pro Lys Arg
                85                  90                  95

His Phe Thr Ile Ile Ile Ile Thr Ile Ser Leu Leu Leu Gly Leu Ile
            100                 105                 110

Val Leu Leu Leu Ile Ser Cys Val Met Trp Lys Ala Gly Phe Phe Lys
        115                 120                 125

Arg Gln Tyr Lys Ser Ile Leu Gln Glu Glu Asn Arg Arg Asp Ser Trp
    130                 135                 140

Ser Tyr Val Asn Ser Lys Ser Asn Asp Asp
145                 150

<210> SEQ ID NO 17
<211> LENGTH: 156
<212> TYPE: PRT
<213> ORGANISM: Homo sapiens

<400> SEQUENCE: 17

Phe Phe Thr Lys Ser Gly Arg Lys Val Leu Asp Cys Glu Lys Pro Gly
1               5                   10                  15

Ile Ser Cys Leu Thr Ala His Cys Asn Phe Ser Ala Leu Ala Lys Glu
            20                  25                  30

Glu Ser Arg Thr Ile Asp Ile Tyr Met Leu Leu Asn Thr Glu Ile Leu
        35                  40                  45

Lys Lys Asp Ser Ser Ser Val Ile Gln Phe Met Ser Arg Ala Lys Val
    50                  55                  60

Lys Val Asp Pro Ala Leu Arg Val Val Glu Ile Ala His Gly Asn Pro
65                  70                  75                  80

Glu Glu Val Thr Val Val Phe Glu Ala Leu His Asn Leu Glu Pro Arg
                85                  90                  95

Gly Tyr Val Val Gly Trp Ile Ile Ala Ile Ser Leu Leu Val Gly Ile
            100                 105                 110

Leu Ile Phe Leu Leu Leu Ala Val Leu Leu Trp Lys Met Gly Phe Phe
        115                 120                 125

Arg Arg Arg Tyr Lys Glu Ile Ile Glu Ala Glu Lys Asn Arg Lys Glu
    130                 135                 140

Asn Glu Asp Ser Trp Asp Trp Val Gln Lys Asn Gln
145                 150                 155

<210> SEQ ID NO 18

```
<211> LENGTH: 125
<212> TYPE: PRT
<213> ORGANISM: Homo sapiens

<400> SEQUENCE: 18

Lys Arg Gly Thr Ile Leu Asp Cys Asn Thr Cys Lys Phe Ala Thr Ile
1               5                   10                  15

Thr Cys Asn Leu Thr Ser Ser Asp Ile Ser Gln Val Asn Val Ser Leu
            20                  25                  30

Ile Leu Trp Lys Pro Thr Phe Ile Lys Ser Tyr Phe Ser Ser Leu Asn
        35                  40                  45

Leu Thr Ile Arg Gly Glu Leu Arg Ser Glu Asn Ala Ser Leu Val Leu
    50                  55                  60

Ser Ser Ser Asn Gln Lys Arg Glu Leu Val Ile Gln Ile Ser Lys Asp
65                  70                  75                  80

Gly Leu Pro Gly Arg Val Pro Leu Trp Val Ile Leu Ser Ala Phe
                85                  90                  95

Ala Gly Leu Leu Leu Leu Met Leu Leu Ile Leu Ala Leu Trp Lys Ile
                100                 105                 110

Gly Phe Phe Lys Arg Pro Leu Lys Lys Met Glu Lys
        115                 120                 125

<210> SEQ ID NO 19
<211> LENGTH: 139
<212> TYPE: PRT
<213> ORGANISM: Homo sapiens

<400> SEQUENCE: 19

Arg His Thr Lys Glu Leu Asn Cys Arg Thr Ala Ser Cys Ser Asn Val
1               5                   10                  15

Thr Cys Trp Leu Lys Asp Val His Met Lys Gly Glu Tyr Phe Val Asn
            20                  25                  30

Val Thr Thr Arg Ile Trp Asn Gly Thr Phe Ala Ser Ser Thr Phe Gln
        35                  40                  45

Thr Val Gln Leu Thr Ala Ala Ala Glu Ile Asn Thr Tyr Asn Pro Glu
    50                  55                  60

Ile Tyr Val Ile Glu Asp Asn Thr Val Thr Ile Pro Leu Val Ile Met
65                  70                  75                  80

Lys Pro Asp Glu Lys Ala Glu Val Pro Thr Gly Val Ile Ile Gly Ser
                85                  90                  95

Ile Ile Ala Gly Ile Leu Leu Leu Ala Leu Val Ala Ile Leu Trp
                100                 105                 110

Lys Leu Gly Phe Phe Lys Arg Lys Tyr Glu Lys Met Thr Lys Asn Pro
        115                 120                 125

Asp Glu Ile Asp Glu Thr Thr Glu Leu Ser Ser
    130                 135

<210> SEQ ID NO 20
<211> LENGTH: 139
<212> TYPE: PRT
<213> ORGANISM: Mus musculus

<400> SEQUENCE: 20

Arg His Thr Lys Glu Leu Asp Cys Arg Thr Thr Ser Cys Ser Asn Ile
1               5                   10                  15

Thr Cys Trp Leu Lys Asp Leu His Met Lys Ala Glu Tyr Phe Ile Asn
            20                  25                  30
```

```
Val Thr Thr Arg Val Trp Asn Arg Thr Phe Ala Ala Ser Thr Phe Gln
         35                  40                  45

Thr Val Gln Leu Thr Ala Ala Glu Ile Asp Thr His Asn Pro Gln
 50                  55                  60

Leu Phe Val Ile Glu Glu Asn Ala Val Thr Ile Pro Leu Val Ile Met
 65                  70                  75                  80

Lys Pro Thr Glu Lys Ala Glu Val Pro Thr Gly Val Ile Gly Ser
                 85                  90                  95

Ile Ile Ala Gly Ile Leu Leu Leu Ala Met Thr Ala Gly Leu Trp
                100                 105                 110

Lys Leu Gly Phe Phe Lys Arg Gln Tyr Lys Lys Met Gly Gln Asn Pro
                115                 120                 125

Asp Glu Met Asp Glu Thr Thr Glu Leu Asn Ser
        130                 135
```

```
<210> SEQ ID NO 21
<211> LENGTH: 135
<212> TYPE: PRT
<213> ORGANISM: Homo sapiens

<400> SEQUENCE: 21

Gln His Thr Asn Arg Leu Asn Gly Ser Asn Thr Gln Cys Gln Val Val
 1               5                  10                  15

Arg Cys His Leu Gly Gln Leu Ala Lys Gly Thr Glu Val Ser Val Gly
                20                  25                  30

Leu Leu Arg Leu Val His Asn Glu Phe Phe Arg Arg Ala Lys Phe Lys
                35                  40                  45

Ser Leu Thr Val Val Ser Thr Phe Glu Leu Gly Thr Glu Glu Gly Ser
 50                  55                  60

Val Leu Gln Leu Thr Glu Ala Ser Arg Trp Ser Glu Ser Val Leu Glu
 65                  70                  75                  80

Val Val Gln Thr Arg Pro Ile Leu Ile Ser Leu Trp Ile Leu Ile Gly
                 85                  90                  95

Ser Val Leu Gly Gly Leu Leu Leu Leu Ala Leu Leu Val Phe Cys Leu
                100                 105                 110

Trp Lys Leu Gly Phe Phe Ala His Lys Lys Ile Pro Glu Glu Glu Lys
                115                 120                 125

Arg Glu Glu Lys Leu Glu Gln
        130                 135
```

```
<210> SEQ ID NO 22
<211> LENGTH: 136
<212> TYPE: PRT
<213> ORGANISM: Homo sapiens

<400> SEQUENCE: 22

Arg Arg Ala Pro Gln Leu Asn His Ser Asn Ser Asp Val Val Ser Ile
 1               5                  10                  15

Asn Cys Asn Ile Arg Leu Val Pro Asn Gln Glu Ile Asn Phe His Leu
                20                  25                  30

Leu Gly Asn Leu Trp Leu Arg Ser Leu Lys Ala Leu Lys Tyr Lys Ser
                35                  40                  45

Met Lys Ile Met Val Asn Ala Ala Leu Gln Arg Gln Phe His Ser Pro
 50                  55                  60

Phe Ile Phe Arg Glu Glu Asp Pro Ser Arg Gln Ile Val Phe Glu Ile
 65                  70                  75                  80
```

Ser Lys Gln Glu Asp Trp Gln Val Pro Ile Trp Ile Ile Val Gly Ser
                85                  90                  95

Thr Leu Gly Gly Leu Leu Leu Ala Leu Leu Val Leu Ala Leu Trp
            100                 105                 110

Lys Leu Gly Phe Phe Arg Ser Ala Arg Arg Arg Glu Pro Gly Leu
            115                 120                 125

Asp Pro Thr Pro Lys Val Leu Glu
            130                 135

<210> SEQ ID NO 23
<211> LENGTH: 136
<212> TYPE: PRT
<213> ORGANISM: Homo sapiens

<400> SEQUENCE: 23

Ser Ser Val Gln His Val Glu Glu Trp His Ser Val Ser Cys Val Ile
1               5                   10                  15

Ala Ser Asp Lys Glu Asn Val Thr Val Ala Ala Glu Ile Ser Trp Asp
            20                  25                  30

His Ser Glu Glu Leu Leu Lys Asp Val Thr Glu Leu Gln Ile Leu Gly
        35                  40                  45

Glu Ile Ser Phe Asn Lys Ser Leu Tyr Glu Gly Leu Asn Ala Glu Asn
    50                  55                  60

His Arg Thr Lys Ile Val Val Phe Leu Lys Asp Glu Lys Tyr His
65                  70                  75                  80

Ser Leu Pro Ile Ile Ile Lys Gly Ser Val Gly Gly Leu Leu Val Leu
                85                  90                  95

Ile Val Ile Leu Val Ile Leu Phe Lys Cys Gly Phe Phe Lys Arg Lys
            100                 105                 110

Tyr Gln Gln Leu Asn Leu Glu Ser Ile Arg Lys Ala Gln Leu Lys Ser
            115                 120                 125

Glu Asn Leu Leu Glu Glu Glu Asn
            130                 135

<210> SEQ ID NO 24
<211> LENGTH: 134
<212> TYPE: PRT
<213> ORGANISM: Mus musculus

<400> SEQUENCE: 24

Asp Pro Val Gln His Val Lys Glu Trp His Ser Val Val Cys Ala Ile
1               5                   10                  15

Thr Ser Asn Lys Glu Asn Val Thr Val Ala Ala Glu Ile Ser Val Gly
            20                  25                  30

His Thr Lys Gln Leu Leu Arg Asp Val Ser Glu Leu Pro Ile Leu Gly
        35                  40                  45

Glu Ile Ser Phe Asn Lys Ser Leu Tyr Glu Gly Leu Asn Ala Glu Asn
    50                  55                  60

His Arg Thr Lys Ile Val Val Ile Phe Leu Lys Glu Glu Glu Thr Arg
65                  70                  75                  80

Ser Leu Pro Leu Ile Ile Gly Ser Ser Ile Gly Gly Leu Leu Val Leu
                85                  90                  95

Val Val Ile Ile Ala Ile Leu Phe Lys Cys Gly Phe Phe Lys Arg Lys
            100                 105                 110

Tyr Gln Gln Leu Asn Leu Glu Ser Thr Arg Arg Ala Gln Leu Lys Ala
            115                 120                 125

```
Asp Ser Leu Leu Gln Asp
    130
```

<210> SEQ ID NO 25
<211> LENGTH: 152
<212> TYPE: PRT
<213> ORGANISM: Homo sapiens

<400> SEQUENCE: 25

```
Ser Arg Ser Pro Met Leu Asp Cys Ser Ile Ala Asp Cys Leu Gln Phe
1               5                   10                  15

Arg Cys Asp Val Pro Ser Phe Ser Val Gln Glu Glu Leu Asp Phe Thr
            20                  25                  30

Leu Lys Gly Asn Leu Ser Phe Gly Trp Val Arg Glu Thr Leu Gln Lys
        35                  40                  45

Lys Val Leu Val Val Ser Val Ala Glu Ile Thr Phe Asp Thr Ser Val
    50                  55                  60

Tyr Ser Gln Leu Pro Gly Gln Glu Ala Phe Met Arg Ala Val Met Glu
65                  70                  75                  80

Met Val Leu Glu Glu Asp Glu Val Tyr Asn Ala Ile Pro Ile Ile Met
                85                  90                  95

Gly Ser Ser Val Gly Ala Leu Leu Leu Ala Leu Ile Thr Ala Thr
            100                 105                 110

Leu Tyr Lys Leu Gly Phe Phe Lys Arg His Tyr Lys Glu Met Leu Glu
        115                 120                 125

Asp Lys Pro Glu Asp Thr Ala Thr Phe Ser Gly Asp Asp Phe Ser Cys
    130                 135                 140

Val Ala Pro Asn Val Pro Leu Ser
145                 150
```

<210> SEQ ID NO 26
<211> LENGTH: 149
<212> TYPE: PRT
<213> ORGANISM: Homo sapiens

<400> SEQUENCE: 26

```
Gln Lys Asn Pro Val Leu Asp Cys Ser Ile Ala Gly Cys Leu Arg Phe
1               5                   10                  15

Arg Cys Asp Val Pro Ser Phe Ser Val Gln Glu Glu Leu Asp Phe Thr
            20                  25                  30

Leu Lys Gly Asn Leu Ser Phe Gly Trp Val Arg Gln Ile Leu Gln Lys
        35                  40                  45

Lys Val Ser Val Val Ser Val Ala Glu Ile Thr Phe Asp Thr Ser Val
    50                  55                  60

Tyr Ser Gln Leu Pro Gly Gln Glu Ala Phe Met Arg Ala Val Thr Thr
65                  70                  75                  80

Thr Val Leu Glu Lys Tyr Lys Val His Asn Pro Thr Pro Leu Ile Val
                85                  90                  95

Gly Ser Ser Ile Gly Gly Leu Leu Leu Ala Leu Ile Thr Ala Val
            100                 105                 110

Leu Tyr Lys Val Gly Phe Phe Lys Arg Gln Tyr Lys Glu Met Met Glu
        115                 120                 125

Glu Ala Asn Gly Gln Ile Ala Pro Glu Asn Gly Thr Gln Thr Pro Ser
    130                 135                 140

Pro Pro Ser Glu Lys
145
```

<210> SEQ ID NO 27
<211> LENGTH: 146
<212> TYPE: PRT
<213> ORGANISM: Mus musculus

<400> SEQUENCE: 27

Gln Lys Ser Pro Val Leu Asp Cys Ser Ile Ala Asp Cys Leu His Leu
1               5                   10                  15

Arg Cys Asp Ile Pro Ser Leu Gly Ile Leu Asp Glu Leu Tyr Phe Ile
            20                  25                  30

Leu Lys Gly Asn Leu Ser Phe Gly Trp Ile Ser Gln Thr Leu Gln Lys
        35                  40                  45

Lys Val Leu Leu Leu Ser Glu Ala Glu Ile Thr Phe Asn Thr Ser Val
    50                  55                  60

Tyr Ser Gln Leu Pro Gly Gln Glu Ala Phe Leu Arg Ala Val Thr Lys
65                  70                  75                  80

Thr Val Leu Glu Met Tyr Lys Val His Asn Pro Val Pro Leu Ile Val
                85                  90                  95

Gly Ser Ser Val Gly Gly Leu Leu Leu Ala Ile Ile Thr Ala Ile
            100                 105                 110

Leu Tyr Lys Ala Gly Phe Phe Lys Arg Gln Tyr Lys Glu Met Leu Glu
        115                 120                 125

Glu Ala Asn Gly Gln Phe Val Ser Asp Gly Thr Pro Thr Pro Gln Val
    130                 135                 140

Ala Gln
145

<210> SEQ ID NO 28
<211> LENGTH: 138
<212> TYPE: PRT
<213> ORGANISM: Homo sapiens

<400> SEQUENCE: 28

Arg Lys Ala Pro Val Val Asn Cys Ser Ile Ala Val Cys Gln Arg Ile
1               5                   10                  15

Gln Cys Asp Ile Pro Phe Phe Gly Ile Gln Glu Glu Phe Asn Ala Thr
            20                  25                  30

Leu Lys Gly Asn Leu Ser Phe Asp Trp Tyr Ile Lys Thr Ser His Asn
        35                  40                  45

His Leu Leu Ile Val Ser Thr Ala Glu Ile Leu Phe Asn Asp Ser Val
    50                  55                  60

Phe Thr Leu Leu Pro Gly Gln Gly Ala Phe Val Arg Ser Val Thr Glu
65                  70                  75                  80

Thr Lys Val Glu Pro Phe Glu Val Pro Asn Pro Leu Pro Leu Ile Val
                85                  90                  95

Gly Ser Ser Val Gly Gly Leu Leu Leu Ala Leu Ile Thr Ala Ala
            100                 105                 110

Leu Tyr Lys Leu Gly Phe Phe Lys Arg Gln Tyr Lys Asp Met Met Ser
        115                 120                 125

Glu Gly Gly Pro Pro Gly Ala Glu Pro Gln
    130                 135

<210> SEQ ID NO 29
<211> LENGTH: 138
<212> TYPE: PRT
<213> ORGANISM: Mus musculus

<400> SEQUENCE: 29

Glu Arg Thr Pro Val Leu Asn Cys Ser Val Ala Val Cys Lys Arg Ile
1               5                   10                  15

Gln Cys Asp Leu Pro Ser Phe Asn Thr Gln Glu Ile Phe Asn Val Thr
            20                  25                  30

Leu Lys Gly Asn Leu Ser Phe Asp Trp Tyr Ile Lys Thr Ser His Gly
        35                  40                  45

His Leu Leu Leu Val Ser Ser Thr Glu Ile Leu Phe Asn Asp Ser Ala
    50                  55                  60

Phe Ala Leu Leu Pro Gly Gln Glu Ser Tyr Val Arg Ser Val Thr Glu
65                  70                  75                  80

Thr Lys Val Glu Pro Tyr Glu Val His Asn Pro Val Pro Leu Ile Val
                85                  90                  95

Gly Ser Ser Ile Gly Gly Leu Val Leu Leu Ala Leu Ile Thr Ala Gly
            100                 105                 110

Leu Tyr Lys Leu Gly Phe Phe Lys Arg Gln Tyr Lys Asp Met Met Asn
        115                 120                 125

Glu Ala Ala Pro Gln Asp Ala Pro Pro Gln
    130                 135

<210> SEQ ID NO 30
<211> LENGTH: 163
<212> TYPE: PRT
<213> ORGANISM: Homo sapiens

<400> SEQUENCE: 30

Asp Ala Ala Glu Pro Cys Leu Pro Gly Ala Leu Phe Arg Cys Pro Val
1               5                   10                  15

Val Phe Arg Gln Glu Ile Leu Val Gln Val Ile Gly Thr Leu Glu Leu
            20                  25                  30

Val Gly Glu Ile Glu Ala Ser Ser Met Phe Ser Leu Cys Ser Ser Leu
        35                  40                  45

Ser Ile Ser Phe Asn Ser Ser Lys His Phe His Leu Tyr Gly Ser Asn
    50                  55                  60

Ala Ser Leu Ala Gln Val Val Met Lys Val Asp Val Val Tyr Glu Lys
65                  70                  75                  80

Gln Met Leu Tyr Leu Tyr Val Leu Ser Gly Ile Gly Gly Leu Leu Leu
                85                  90                  95

Leu Leu Leu Ile Phe Ile Val Leu Tyr Lys Val Gly Phe Phe Lys Arg
            100                 105                 110

Asn Leu Lys Glu Lys Met Glu Ala Gly Arg Gly Val Pro Asn Gly Ile
        115                 120                 125

Pro Ala Glu Asp Ser Glu Gln Leu Ala Ser Gly Gln Glu Ala Gly Asp
    130                 135                 140

Pro Gly Cys Leu Lys Pro Leu His Glu Lys Asp Ser Glu Ser Gly Gly
145                 150                 155                 160

Gly Lys Asp

<210> SEQ ID NO 31
<211> LENGTH: 159
<212> TYPE: PRT
<213> ORGANISM: Mus musculus

<400> SEQUENCE: 31

Ser Glu Ala Glu Gln Pro Cys Leu Pro Gly Val Gln Phe Arg Cys Pro
1               5                   10                  15

```
Ile Val Phe Arg Trp Glu Ile Leu Ile Gln Val Thr Gly Thr Val Glu
             20                  25                  30

Leu Ser Lys Glu Ile Lys Ala Ser Ser Thr Leu Ser Leu Cys Ser Ser
         35                  40                  45

Leu Ser Val Ser Phe Asn Ser Ser Lys His Phe His Leu Tyr Gly Ser
     50                  55                  60

Lys Ala Ser Glu Ala Gln Val Leu Val Lys Val Asp Leu Ile His Glu
 65                  70                  75                  80

Lys Glu Met Leu His Val Tyr Val Leu Ser Gly Ile Gly Gly Leu Val
                 85                  90                  95

Leu Leu Phe Leu Ile Phe Leu Ala Leu Tyr Lys Val Gly Phe Phe Lys
            100                 105                 110

Arg Asn Leu Lys Glu Lys Met Glu Ala Asp Gly Gly Val Pro Asn Gly
        115                 120                 125

Ser Pro Pro Glu Asp Thr Asp Pro Leu Ala Val Pro Gly Glu Glu Thr
    130                 135                 140

Lys Asp Met Gly Cys Leu Glu Pro Leu Arg Glu Ser Asp Lys Asp
145                 150                 155

<210> SEQ ID NO 32
<211> LENGTH: 778
<212> TYPE: PRT
<213> ORGANISM: Homo sapiens

<400> SEQUENCE: 32

Gln Thr Asp Glu Asn Arg Cys Leu Lys Ala Asn Ala Lys Ser Cys Gly
1               5                   10                  15

Glu Cys Ile Gln Ala Gly Pro Asn Cys Gly Trp Cys Thr Asn Ser Thr
             20                  25                  30

Phe Leu Gln Glu Gly Met Pro Thr Ser Ala Arg Cys Asp Asp Leu Glu
         35                  40                  45

Ala Leu Lys Lys Lys Gly Cys Pro Pro Asp Asp Ile Glu Asn Pro Arg
     50                  55                  60

Gly Ser Lys Asp Ile Lys Lys Asn Lys Asn Val Thr Asn Arg Ser Lys
 65                  70                  75                  80

Gly Thr Ala Glu Lys Leu Lys Pro Glu Asp Ile His Gln Ile Gln Pro
                 85                  90                  95

Gln Gln Leu Val Leu Arg Leu Arg Ser Gly Glu Pro Gln Thr Phe Thr
            100                 105                 110

Leu Lys Phe Lys Arg Ala Glu Asp Tyr Pro Ile Asp Leu Tyr Tyr Leu
        115                 120                 125

Met Asp Leu Ser Tyr Ser Met Lys Asp Asp Leu Glu Asn Val Lys Ser
    130                 135                 140

Leu Gly Thr Asp Leu Met Asn Glu Met Arg Arg Ile Thr Ser Asp Phe
145                 150                 155                 160

Arg Ile Gly Phe Gly Ser Phe Val Glu Lys Thr Val Met Pro Tyr Ile
                165                 170                 175

Ser Thr Thr Pro Ala Lys Leu Arg Asn Pro Cys Thr Ser Glu Gln Asn
            180                 185                 190

Cys Thr Thr Pro Phe Ser Tyr Lys Asn Val Leu Ser Leu Thr Asn Lys
        195                 200                 205

Gly Glu Val Phe Asn Glu Leu Val Gly Lys Gln Arg Ile Ser Gly Asn
    210                 215                 220

Leu Asp Ser Pro Glu Gly Gly Phe Asp Ala Ile Met Gln Val Ala Val
```

```
            225                 230                 235                 240
Cys Gly Ser Leu Ile Gly Trp Arg Asn Val Thr Arg Leu Leu Val Phe
                245                 250                 255

Ser Thr Asp Ala Gly Phe His Phe Ala Gly Asp Gly Lys Leu Gly Gly
                260                 265                 270

Ile Val Leu Pro Asn Asp Gly Gln Cys His Leu Glu Asn Asn Met Tyr
                275                 280                 285

Thr Met Ser His Tyr Tyr Asp Tyr Pro Ser Ile Ala His Leu Val Gln
        290                 295                 300

Lys Leu Ser Glu Asn Asn Ile Gln Thr Ile Phe Ala Val Thr Glu Glu
305                 310                 315                 320

Phe Gln Pro Val Tyr Lys Glu Leu Lys Asn Leu Ile Pro Lys Ser Ala
                325                 330                 335

Val Gly Thr Leu Ser Ala Asn Ser Ser Asn Val Ile Gln Leu Ile Ile
                340                 345                 350

Asp Ala Tyr Asn Ser Leu Ser Ser Glu Val Ile Leu Glu Asn Gly Lys
                355                 360                 365

Leu Ser Glu Gly Val Thr Ile Ser Tyr Lys Ser Tyr Cys Lys Asn Gly
    370                 375                 380

Val Asn Gly Thr Gly Glu Asn Gly Arg Lys Cys Ser Asn Ile Ser Ile
385                 390                 395                 400

Gly Asp Glu Val Gln Phe Glu Ile Ser Ile Thr Ser Asn Lys Cys Pro
                405                 410                 415

Lys Lys Asp Ser Asp Ser Phe Lys Ile Arg Pro Leu Gly Phe Thr Glu
                420                 425                 430

Glu Val Glu Val Ile Leu Gln Tyr Ile Cys Glu Cys Glu Cys Gln Ser
            435                 440                 445

Glu Gly Ile Pro Glu Ser Pro Lys Cys His Glu Gly Asn Gly Thr Phe
    450                 455                 460

Glu Cys Gly Ala Cys Arg Cys Asn Glu Gly Arg Val Gly Arg His Cys
465                 470                 475                 480

Glu Cys Ser Thr Asp Glu Val Asn Ser Glu Asp Met Asp Ala Tyr Cys
                485                 490                 495

Arg Lys Glu Asn Ser Ser Glu Ile Cys Ser Asn Asn Gly Glu Cys Val
                500                 505                 510

Cys Gly Gln Cys Val Cys Arg Lys Arg Asp Asn Thr Asn Glu Ile Tyr
                515                 520                 525

Ser Gly Lys Phe Cys Glu Cys Asp Asn Phe Asn Cys Asp Arg Ser Asn
    530                 535                 540

Gly Leu Ile Cys Gly Gly Asn Gly Val Cys Lys Cys Arg Val Cys Glu
545                 550                 555                 560

Cys Asn Pro Asn Tyr Thr Gly Ser Ala Cys Asp Cys Ser Leu Asp Thr
                565                 570                 575

Ser Thr Cys Glu Ala Ser Asn Gly Gln Ile Cys Asn Gly Arg Gly Ile
                580                 585                 590

Cys Glu Cys Gly Val Cys Lys Cys Thr Asp Pro Lys Phe Gln Gly Gln
            595                 600                 605

Thr Cys Glu Met Cys Gln Thr Cys Leu Gly Val Cys Ala Glu His Lys
    610                 615                 620

Glu Cys Val Gln Cys Arg Ala Phe Asn Lys Gly Glu Lys Lys Asp Thr
625                 630                 635                 640

Cys Thr Gln Glu Cys Ser Tyr Phe Asn Ile Thr Lys Val Glu Ser Arg
                645                 650                 655
```

```
Asp Lys Leu Pro Gln Pro Val Gln Pro Asp Pro Val Ser His Cys Lys
            660                 665                 670
Glu Lys Asp Val Asp Asp Cys Trp Phe Tyr Phe Thr Tyr Ser Val Asn
        675                 680                 685
Gly Asn Asn Glu Val Met Val His Val Val Glu Asn Pro Glu Cys Pro
    690                 695                 700
Thr Gly Pro Asp Ile Ile Pro Ile Val Ala Gly Val Val Ala Gly Ile
705                 710                 715                 720
Val Leu Ile Gly Leu Ala Leu Leu Ile Trp Lys Leu Leu Met Ile
                725                 730                 735
Ile His Asp Arg Arg Glu Phe Ala Lys Phe Glu Lys Glu Lys Met Asn
            740                 745                 750
Ala Lys Trp Asp Thr Gly Glu Asn Pro Ile Tyr Lys Ser Ala Val Thr
        755                 760                 765
Thr Val Val Asn Pro Lys Tyr Glu Gly Lys
    770                 775
```

<210> SEQ ID NO 33
<211> LENGTH: 778
<212> TYPE: PRT
<213> ORGANISM: Mus musculus

<400> SEQUENCE: 33

```
Gln Thr Asp Lys Asn Arg Cys Leu Lys Ala Asn Ala Lys Ser Cys Gly
1               5                   10                  15
Glu Cys Ile Gln Ala Gly Pro Asn Cys Gly Trp Cys Thr Asn Thr Thr
            20                  25                  30
Phe Leu Gln Glu Gly Met Pro Thr Ser Ala Arg Cys Asp Asp Leu Glu
        35                  40                  45
Ala Leu Lys Lys Lys Gly Cys Gln Pro Ser Asp Ile Glu Asn Pro Arg
    50                  55                  60
Gly Ser Gln Thr Ile Lys Lys Asn Lys Asn Val Thr Asn Arg Ser Lys
65                  70                  75                  80
Gly Met Ala Glu Lys Leu Arg Pro Glu Asp Ile Thr Gln Ile Gln Pro
            85                  90                  95
Gln Gln Leu Leu Leu Lys Leu Arg Ser Gly Glu Pro Gln Lys Phe Thr
        100                 105                 110
Leu Lys Phe Lys Arg Ala Glu Asp Tyr Pro Ile Asp Leu Tyr Tyr Leu
    115                 120                 125
Met Asp Leu Ser Tyr Ser Met Lys Asp Asp Leu Glu Asn Val Lys Ser
    130                 135                 140
Leu Gly Thr Asp Leu Met Asn Glu Met Arg Arg Ile Thr Ser Asp Phe
145                 150                 155                 160
Arg Ile Gly Phe Gly Ser Phe Val Glu Lys Thr Val Met Pro Tyr Ile
                165                 170                 175
Ser Thr Thr Pro Ala Lys Leu Arg Asn Pro Cys Thr Ser Glu Gln Asn
            180                 185                 190
Cys Thr Ser Pro Phe Ser Tyr Lys Asn Val Leu Ser Leu Thr Asp Arg
        195                 200                 205
Gly Glu Phe Phe Asn Glu Leu Val Gly Gln Gln Arg Ile Ser Gly Asn
    210                 215                 220
Leu Asp Ser Pro Glu Gly Gly Phe Asp Ala Ile Met Gln Val Ala Val
225                 230                 235                 240
Cys Gly Ser Leu Ile Gly Trp Arg Asn Val Thr Arg Leu Leu Val Phe
```

```
                  245                 250                 255
Ser Thr Asp Ala Gly Phe His Phe Ala Gly Asp Gly Lys Leu Gly Gly
                260                 265                 270
Ile Val Leu Pro Asn Asp Gly Gln Cys His Leu Glu Asn Asn Val Tyr
                275                 280                 285
Thr Met Ser His Tyr Tyr Asp Tyr Pro Ser Ile Ala His Leu Val Gln
                290                 295                 300
Lys Leu Ser Glu Asn Asn Ile Gln Thr Ile Phe Ala Val Thr Glu Glu
305                 310                 315                 320
Phe Gln Pro Val Tyr Lys Glu Leu Lys Asn Leu Ile Pro Lys Ser Ala
                325                 330                 335
Val Gly Thr Leu Ser Gly Asn Ser Ser Asn Val Ile Gln Leu Ile Ile
                340                 345                 350
Asp Ala Tyr Asn Ser Leu Ser Ser Glu Val Ile Leu Glu Asn Ser Lys
                355                 360                 365
Leu Pro Asp Gly Val Thr Ile Asn Tyr Lys Ser Tyr Cys Lys Asn Gly
                370                 375                 380
Val Asn Gly Thr Gly Glu Asn Gly Arg Lys Cys Ser Asn Ile Ser Ile
385                 390                 395                 400
Gly Asp Glu Val Gln Phe Glu Ile Ser Ile Thr Ala Asn Lys Cys Pro
                405                 410                 415
Asn Lys Glu Ser Glu Thr Ile Lys Ile Lys Pro Leu Gly Phe Thr Glu
                420                 425                 430
Glu Val Glu Val Val Leu Gln Phe Ile Cys Lys Cys Asn Cys Gln Ser
                435                 440                 445
His Gly Ile Pro Ala Ser Pro Lys Cys His Glu Gly Asn Gly Thr Phe
                450                 455                 460
Glu Cys Gly Ala Cys Arg Cys Asn Glu Gly Arg Val Gly Arg His Cys
465                 470                 475                 480
Glu Cys Ser Thr Asp Glu Val Asn Ser Glu Asp Met Asp Ala Tyr Cys
                485                 490                 495
Arg Lys Glu Asn Ser Ser Glu Ile Cys Ser Asn Asn Gly Glu Cys Val
                500                 505                 510
Cys Gly Gln Cys Val Cys Arg Lys Arg Asp Asn Thr Asn Glu Ile Tyr
                515                 520                 525
Ser Gly Lys Phe Cys Glu Cys Asp Asn Phe Asn Cys Asp Arg Ser Asn
                530                 535                 540
Gly Leu Ile Cys Gly Gly Asn Gly Val Cys Arg Cys Arg Val Cys Glu
545                 550                 555                 560
Cys Tyr Pro Asn Tyr Thr Gly Ser Ala Cys Asp Cys Ser Leu Asp Thr
                565                 570                 575
Gly Pro Cys Leu Ala Ser Asn Gly Gln Ile Cys Asn Gly Arg Gly Ile
                580                 585                 590
Cys Glu Cys Gly Ala Cys Lys Cys Thr Asp Pro Lys Phe Gln Gly Pro
                595                 600                 605
Thr Cys Glu Thr Cys Gln Thr Cys Leu Gly Val Cys Ala Glu His Lys
                610                 615                 620
Glu Cys Val Gln Cys Arg Ala Phe Asn Lys Gly Glu Lys Lys Asp Thr
625                 630                 635                 640
Cys Ala Gln Glu Cys Ser His Phe Asn Leu Thr Lys Val Glu Ser Arg
                645                 650                 655
Glu Lys Leu Pro Gln Pro Val Gln Val Asp Pro Val Thr His Cys Lys
                660                 665                 670
```

Glu Lys Asp Ile Asp Asp Cys Trp Phe Tyr Phe Thr Tyr Ser Val Asn
            675                 680                 685

Gly Asn Asn Glu Ala Ile Val His Val Val Glu Thr Pro Asp Cys Pro
            690                 695                 700

Thr Gly Pro Asp Ile Ile Pro Ile Val Ala Gly Val Val Ala Gly Ile
705                 710                 715                 720

Val Leu Ile Gly Leu Ala Leu Leu Ile Trp Lys Leu Leu Met Ile
            725                 730                 735

Ile His Asp Arg Arg Glu Phe Ala Lys Phe Glu Lys Glu Lys Met Asn
            740                 745                 750

Ala Lys Trp Asp Thr Gly Glu Asn Pro Ile Tyr Lys Ser Ala Val Thr
            755                 760                 765

Thr Val Val Asn Pro Lys Tyr Glu Gly Lys
            770                 775

<210> SEQ ID NO 34
<211> LENGTH: 747
<212> TYPE: PRT
<213> ORGANISM: Homo sapiens

<400> SEQUENCE: 34

Gln Glu Cys Thr Lys Phe Lys Val Ser Ser Cys Arg Glu Cys Ile Glu
1               5                   10                  15

Ser Gly Pro Gly Cys Thr Trp Cys Gln Lys Leu Asn Phe Thr Gly Pro
            20                  25                  30

Gly Asp Pro Asp Ser Ile Arg Cys Asp Thr Arg Pro Gln Leu Leu Met
            35                  40                  45

Arg Gly Cys Ala Ala Asp Asp Ile Met Asp Pro Thr Ser Leu Ala Glu
        50                  55                  60

Thr Gln Glu Asp His Asn Gly Gly Gln Lys Gln Leu Ser Pro Gln Lys
65                  70                  75                  80

Val Thr Leu Tyr Leu Arg Pro Gly Gln Ala Ala Ala Phe Asn Val Thr
                85                  90                  95

Phe Arg Arg Ala Lys Gly Tyr Pro Ile Asp Leu Tyr Tyr Leu Met Asp
            100                 105                 110

Leu Ser Tyr Ser Met Leu Asp Asp Leu Arg Asn Val Lys Lys Leu Gly
            115                 120                 125

Gly Asp Leu Leu Arg Ala Leu Asn Glu Ile Thr Glu Ser Gly Arg Ile
        130                 135                 140

Gly Phe Gly Ser Phe Val Asp Lys Thr Val Leu Pro Phe Val Asn Thr
145                 150                 155                 160

His Pro Asp Lys Leu Arg Asn Pro Cys Pro Asn Lys Glu Lys Glu Cys
                165                 170                 175

Gln Pro Pro Phe Ala Phe Arg His Val Leu Lys Leu Thr Asn Asn Ser
            180                 185                 190

Asn Gln Phe Gln Thr Glu Val Gly Lys Gln Leu Ile Ser Gly Asn Leu
            195                 200                 205

Asp Ala Pro Glu Gly Gly Leu Asp Ala Met Met Gln Val Ala Ala Cys
        210                 215                 220

Pro Glu Glu Ile Gly Trp Arg Asn Val Thr Arg Leu Leu Val Phe Ala
225                 230                 235                 240

Thr Asp Asp Gly Phe His Phe Ala Gly Asp Gly Lys Leu Gly Ala Ile
                245                 250                 255

Leu Thr Pro Asn Asp Gly Arg Cys His Leu Glu Asp Asn Leu Tyr Lys

```
                  260                 265                 270
Arg Ser Asn Glu Phe Asp Tyr Pro Ser Val Gly Gln Leu Ala His Lys
            275                 280                 285

Leu Ala Glu Asn Asn Ile Gln Pro Ile Phe Ala Val Thr Ser Arg Met
            290                 295                 300

Val Lys Thr Tyr Glu Lys Leu Thr Glu Ile Ile Pro Lys Ser Ala Val
305                 310                 315                 320

Gly Glu Leu Ser Glu Asp Ser Ser Asn Val Val His Leu Ile Lys Asn
                325                 330                 335

Ala Tyr Asn Lys Leu Ser Ser Arg Val Phe Leu Asp His Asn Ala Leu
            340                 345                 350

Pro Asp Thr Leu Lys Val Thr Tyr Asp Ser Phe Cys Ser Asn Gly Val
            355                 360                 365

Thr His Arg Asn Gln Pro Arg Gly Asp Cys Asp Gly Val Gln Ile Asn
            370                 375                 380

Val Pro Ile Thr Phe Gln Val Lys Val Thr Ala Thr Glu Cys Ile Gln
385                 390                 395                 400

Glu Gln Ser Phe Val Ile Arg Ala Leu Gly Phe Thr Asp Ile Val Thr
                405                 410                 415

Val Gln Val Leu Pro Gln Cys Glu Cys Arg Cys Arg Asp Gln Ser Arg
            420                 425                 430

Asp Arg Ser Leu Cys His Gly Lys Gly Phe Leu Glu Cys Gly Ile Cys
            435                 440                 445

Arg Cys Asp Thr Gly Tyr Ile Gly Lys Asn Cys Glu Cys Gln Thr Gln
            450                 455                 460

Gly Arg Ser Ser Gln Glu Leu Glu Gly Ser Cys Arg Lys Asp Asn Asn
465                 470                 475                 480

Ser Ile Ile Cys Ser Gly Leu Gly Asp Cys Val Cys Gly Gln Cys Leu
                485                 490                 495

Cys His Thr Ser Asp Val Pro Gly Lys Leu Ile Tyr Gly Gln Tyr Cys
            500                 505                 510

Glu Cys Asp Thr Ile Asn Cys Glu Arg Tyr Asn Gly Gln Val Cys Gly
            515                 520                 525

Gly Pro Gly Arg Gly Leu Cys Phe Cys Gly Lys Cys Arg Cys His Pro
            530                 535                 540

Gly Phe Glu Gly Ser Ala Cys Gln Cys Glu Arg Thr Thr Glu Gly Cys
545                 550                 555                 560

Leu Asn Pro Arg Arg Val Glu Cys Ser Gly Arg Gly Arg Cys Arg Cys
                565                 570                 575

Asn Val Cys Glu Cys His Ser Gly Tyr Gln Leu Pro Leu Cys Gln Glu
            580                 585                 590

Cys Pro Gly Cys Pro Ser Pro Cys Gly Lys Tyr Ile Ser Cys Ala Glu
            595                 600                 605

Cys Leu Lys Phe Glu Lys Gly Pro Phe Gly Lys Asn Cys Ser Ala Ala
            610                 615                 620

Cys Pro Gly Leu Gln Leu Ser Asn Asn Pro Val Lys Gly Arg Thr Cys
625                 630                 635                 640

Lys Glu Arg Asp Ser Glu Gly Cys Trp Val Ala Tyr Thr Leu Glu Gln
                645                 650                 655

Gln Asp Gly Met Asp Arg Tyr Leu Ile Tyr Val Asp Glu Ser Arg Glu
            660                 665                 670

Cys Val Ala Gly Pro Asn Ile Ala Ala Ile Val Gly Gly Thr Val Ala
            675                 680                 685
```

```
Gly Ile Val Leu Ile Gly Ile Leu Leu Val Ile Trp Lys Ala Leu
            690                 695                 700

Ile His Leu Ser Asp Leu Arg Glu Tyr Arg Arg Phe Glu Lys Glu Lys
705                 710                 715                 720

Leu Lys Ser Gln Trp Asn Asn Asp Asn Pro Leu Phe Lys Ser Ala Thr
                725                 730                 735

Thr Thr Val Met Asn Pro Lys Phe Ala Glu Ser
740                 745
```

<210> SEQ ID NO 35
<211> LENGTH: 748
<212> TYPE: PRT
<213> ORGANISM: Mus musculus

<400> SEQUENCE: 35

```
Gln Glu Cys Thr Lys Tyr Lys Val Ser Ser Cys Arg Asp Cys Ile Gln
1               5                   10                  15

Ser Gly Pro Gly Cys Ser Trp Cys Gln Lys Leu Asn Phe Thr Gly Pro
                20                  25                  30

Gly Glu Pro Asp Ser Leu Arg Cys Asp Thr Arg Ala Gln Leu Leu Leu
            35                  40                  45

Lys Gly Cys Pro Ala Asp Asp Ile Met Asp Pro Arg Ser Ile Ala Asn
50                  55                  60

Pro Glu Phe Asp Gln Arg Gly Gln Arg Lys Gln Leu Ser Pro Gln Lys
65                  70                  75                  80

Val Thr Leu Tyr Leu Arg Pro Gly Gln Ala Ala Ala Phe Asn Val Thr
                85                  90                  95

Phe Arg Arg Ala Lys Gly Tyr Pro Ile Asp Leu Tyr Tyr Leu Met Asp
            100                 105                 110

Leu Ser Tyr Ser Met Leu Asp Asp Leu Asn Asn Val Lys Lys Leu Gly
        115                 120                 125

Gly Asp Leu Leu Gln Ala Leu Asn Glu Ile Thr Glu Ser Gly Arg Ile
    130                 135                 140

Gly Phe Gly Ser Phe Val Asp Lys Thr Val Leu Pro Phe Val Asn Thr
145                 150                 155                 160

His Pro Glu Lys Leu Arg Asn Pro Cys Pro Asn Lys Glu Lys Ala Cys
                165                 170                 175

Gln Pro Pro Phe Ala Phe Arg His Val Leu Lys Leu Thr Asp Asn Ser
            180                 185                 190

Asn Gln Phe Gln Thr Glu Val Gly Lys Gln Leu Ile Ser Gly Asn Leu
        195                 200                 205

Asp Ala Pro Glu Gly Gly Leu Asp Ala Ile Met Gln Val Ala Ala Cys
    210                 215                 220

Pro Glu Glu Ile Gly Trp Arg Asn Val Thr Arg Leu Leu Val Phe Ala
225                 230                 235                 240

Thr Asp Asp Gly Phe His Phe Ala Gly Asp Gly Lys Leu Gly Ala Ile
                245                 250                 255

Leu Thr Pro Asn Asp Gly Arg Cys His Leu Glu Asp Asn Met Tyr Lys
            260                 265                 270

Arg Ser Asn Glu Phe Asp Tyr Pro Ser Val Gly Gln Leu Ala His Lys
        275                 280                 285

Leu Ser Glu Ser Asn Ile Gln Pro Ile Phe Ala Val Thr Lys Lys Met
    290                 295                 300

Val Lys Thr Tyr Glu Lys Leu Thr Glu Ile Ile Pro Lys Ser Ala Val
```

```
              305                 310                 315                 320
        Gly Glu Leu Ser Asp Asp Ser Ser Asn Val Val Gln Leu Ile Lys Asn
                        325                 330                 335

Ala Tyr Tyr Lys Leu Ser Ser Arg Val Phe Leu Asp His Ser Thr Leu
                        340                 345                 350

Pro Asp Thr Leu Lys Val Thr Tyr Asp Ser Phe Cys Ser Asn Gly Ala
                        355                 360                 365

Ser Ser Ile Gly Lys Ser Arg Gly Asp Cys Asp Gly Val Gln Ile Asn
            370                 375                 380

Asn Pro Val Thr Phe Gln Val Lys Val Met Ala Ser Glu Cys Ile Gln
        385                 390                 395                 400

Glu Gln Ser Phe Val Ile Arg Ala Leu Gly Phe Thr Asp Thr Val Thr
                        405                 410                 415

Val Gln Val Arg Pro Gln Cys Glu Cys Gln Cys Arg Asp Gln Ser Arg
                        420                 425                 430

Glu Gln Ser Leu Cys Gly Gly Lys Gly Val Met Glu Cys Gly Ile Cys
                        435                 440                 445

Arg Cys Glu Ser Gly Tyr Ile Gly Lys Asn Cys Glu Cys Gln Thr Gln
            450                 455                 460

Gly Arg Ser Ser Gln Glu Leu Glu Arg Asn Cys Arg Lys Asp Asn Ser
        465                 470                 475                 480

Ser Ile Val Cys Ser Gly Leu Gly Asp Cys Ile Cys Gly Gln Cys Val
                        485                 490                 495

Cys His Thr Ser Asp Val Pro Asn Lys Glu Ile Phe Gly Gln Tyr Cys
                        500                 505                 510

Glu Cys Asp Asn Val Asn Cys Glu Arg Tyr Asn Ser Gln Val Cys Gly
                        515                 520                 525

Gly Ser Asp Arg Gly Ser Cys Asn Cys Gly Lys Cys Ser Cys Lys Pro
            530                 535                 540

Gly Tyr Glu Gly Ser Ala Cys Gln Cys Gln Arg Ser Thr Thr Gly Cys
        545                 550                 555                 560

Leu Asn Ala Arg Leu Val Glu Cys Ser Gly Arg Gly His Cys Gln Cys
                        565                 570                 575

Asn Arg Cys Ile Cys Asp Glu Gly Tyr Gln Pro Met Cys Glu Asp
                        580                 585                 590

Cys Pro Ser Cys Gly Ser His Cys Arg Asp Asn His Thr Ser Cys Ala
                        595                 600                 605

Glu Cys Leu Lys Phe Asp Lys Gly Pro Phe Glu Lys Asn Cys Ser Val
                        610                 615                 620

Gln Cys Ala Gly Met Thr Leu Gln Thr Ile Pro Leu Lys Lys Lys Pro
        625                 630                 635                 640

Cys Lys Glu Arg Asp Ser Glu Gly Cys Trp Ile Thr Tyr Thr Leu Gln
                        645                 650                 655

Gln Lys Asp Gly Arg Asn Ile Tyr Asn Ile His Val Glu Asp Ser Leu
                        660                 665                 670

Glu Cys Val Lys Gly Pro Asn Val Ala Ala Ile Val Gly Gly Thr Val
                        675                 680                 685

Val Gly Val Val Leu Ile Gly Val Leu Leu Val Ile Trp Lys Ala
                        690                 695                 700

Leu Thr His Leu Thr Asp Leu Arg Glu Tyr Arg Arg Phe Glu Lys Glu
        705                 710                 715                 720

Lys Leu Lys Ser Gln Trp Asn Asn Asp Asn Pro Leu Phe Lys Ser Ala
                        725                 730                 735
```

Thr Thr Thr Val Met Asn Pro Lys Phe Ala Glu Ser
            740                 745

<210> SEQ ID NO 36
<211> LENGTH: 762
<212> TYPE: PRT
<213> ORGANISM: Homo sapiens

<400> SEQUENCE: 36

Gly Pro Asn Ile Cys Thr Thr Arg Gly Val Ser Ser Cys Gln Gln Cys
1               5                   10                  15

Leu Ala Val Ser Pro Met Cys Ala Trp Cys Ser Asp Glu Ala Leu Pro
            20                  25                  30

Leu Gly Ser Pro Arg Cys Asp Leu Lys Glu Asn Leu Leu Lys Asp Asn
        35                  40                  45

Cys Ala Pro Glu Ser Ile Glu Phe Pro Val Ser Glu Ala Arg Val Leu
    50                  55                  60

Glu Asp Arg Pro Leu Ser Asp Lys Gly Ser Gly Asp Ser Ser Gln Val
65                  70                  75                  80

Thr Gln Val Ser Pro Gln Arg Ile Ala Leu Arg Leu Arg Pro Asp Asp
                85                  90                  95

Ser Lys Asn Phe Ser Ile Gln Val Arg Gln Val Glu Asp Tyr Pro Val
            100                 105                 110

Asp Ile Tyr Tyr Leu Met Asp Leu Ser Tyr Ser Met Lys Asp Asp Leu
        115                 120                 125

Trp Ser Ile Gln Asn Leu Gly Thr Lys Leu Ala Thr Gln Met Arg Lys
    130                 135                 140

Leu Thr Ser Asn Leu Arg Ile Gly Phe Gly Ala Phe Val Asp Lys Pro
145                 150                 155                 160

Val Ser Pro Tyr Met Tyr Ile Ser Pro Pro Glu Ala Leu Glu Asn Pro
                165                 170                 175

Cys Tyr Asp Met Lys Thr Thr Cys Leu Pro Met Phe Gly Tyr Lys His
            180                 185                 190

Val Leu Thr Leu Thr Asp Gln Val Thr Arg Phe Asn Glu Glu Val Lys
        195                 200                 205

Lys Gln Ser Val Ser Arg Asn Arg Asp Ala Pro Glu Gly Gly Phe Asp
    210                 215                 220

Ala Ile Met Gln Ala Thr Val Cys Asp Glu Lys Ile Gly Trp Arg Asn
225                 230                 235                 240

Asp Ala Ser His Leu Leu Val Phe Thr Thr Asp Ala Lys Thr His Ile
                245                 250                 255

Ala Leu Asp Gly Arg Leu Ala Gly Ile Val Gln Pro Asn Asp Gly Gln
            260                 265                 270

Cys His Val Gly Ser Asp Asn His Tyr Ser Ala Ser Thr Thr Met Asp
        275                 280                 285

Tyr Pro Ser Leu Gly Leu Met Thr Glu Lys Leu Ser Gln Lys Asn Ile
    290                 295                 300

Asn Leu Ile Phe Ala Val Thr Glu Asn Val Val Asn Leu Tyr Gln Asn
305                 310                 315                 320

Tyr Ser Glu Leu Ile Pro Gly Thr Thr Val Gly Val Leu Ser Met Asp
                325                 330                 335

Ser Ser Asn Val Leu Gln Leu Ile Val Asp Ala Tyr Gly Lys Ile Arg
            340                 345                 350

Ser Lys Val Glu Leu Glu Val Arg Asp Leu Pro Glu Glu Leu Ser Leu

-continued

```
                355                 360                 365
Ser Phe Asn Ala Thr Cys Leu Asn Asn Glu Val Ile Pro Gly Leu Lys
370                 375                 380

Ser Cys Met Gly Leu Lys Ile Gly Asp Thr Val Ser Phe Ser Ile Glu
385                 390                 395                 400

Ala Lys Val Arg Gly Cys Pro Gln Glu Lys Glu Lys Ser Phe Thr Ile
                405                 410                 415

Lys Pro Val Gly Phe Lys Asp Ser Leu Ile Val Gln Val Thr Phe Asp
                420                 425                 430

Cys Asp Cys Ala Cys Gln Ala Gln Ala Glu Pro Asn Ser His Arg Cys
                435                 440                 445

Asn Asn Gly Asn Gly Thr Phe Glu Cys Gly Val Cys Arg Cys Gly Pro
450                 455                 460

Gly Trp Leu Gly Ser Gln Cys Glu Cys Ser Glu Asp Tyr Arg Pro
465                 470                 475                 480

Ser Gln Gln Asp Glu Cys Ser Pro Arg Glu Gly Gln Pro Val Cys Ser
                485                 490                 495

Gln Arg Gly Glu Cys Leu Cys Gly Gln Cys Val Cys His Ser Ser Asp
                500                 505                 510

Phe Gly Lys Ile Thr Gly Lys Tyr Cys Glu Cys Asp Asp Phe Ser Cys
                515                 520                 525

Val Arg Tyr Lys Gly Glu Met Cys Ser Gly His Gly Gln Cys Ser Cys
530                 535                 540

Gly Asp Cys Leu Cys Asp Ser Asp Trp Thr Gly Tyr Tyr Cys Asn Cys
545                 550                 555                 560

Thr Thr Arg Thr Asp Thr Cys Met Ser Ser Asn Gly Leu Leu Cys Ser
                565                 570                 575

Gly Arg Gly Lys Cys Glu Cys Gly Ser Cys Val Cys Ile Gln Pro Gly
                580                 585                 590

Ser Tyr Gly Asp Thr Cys Glu Lys Cys Pro Thr Cys Pro Asp Ala Cys
                595                 600                 605

Thr Phe Lys Lys Glu Cys Val Glu Cys Lys Lys Phe Asp Arg Gly Ala
610                 615                 620

Leu His Asp Glu Asn Thr Cys Asn Arg Tyr Cys Arg Asp Glu Ile Glu
625                 630                 635                 640

Ser Val Lys Glu Leu Lys Asp Thr Gly Lys Asp Ala Val Asn Cys Thr
                645                 650                 655

Tyr Lys Asn Glu Asp Asp Cys Val Val Arg Phe Gln Tyr Tyr Glu Asp
                660                 665                 670

Ser Ser Gly Lys Ser Ile Leu Tyr Val Val Glu Glu Pro Glu Cys Pro
                675                 680                 685

Lys Gly Pro Asp Ile Leu Val Val Leu Leu Ser Val Met Gly Ala Ile
                690                 695                 700

Leu Leu Ile Gly Leu Ala Ala Leu Leu Ile Trp Lys Leu Leu Ile Thr
705                 710                 715                 720

Ile His Asp Arg Lys Glu Phe Ala Lys Phe Glu Glu Glu Arg Ala Arg
                725                 730                 735

Ala Lys Trp Asp Thr Ala Asn Asn Pro Leu Tyr Lys Glu Ala Thr Ser
                740                 745                 750

Thr Phe Thr Asn Ile Thr Tyr Arg Gly Thr
                755                 760
```

<210> SEQ ID NO 37

<211> LENGTH: 762
<212> TYPE: PRT
<213> ORGANISM: Mus musculus

<400> SEQUENCE: 37

```
Glu Ser Asn Ile Cys Thr Thr Arg Gly Val Asn Ser Cys Gln Gln Cys
1               5                   10                  15

Leu Ala Val Ser Pro Val Cys Ala Trp Cys Ser Asp Glu Thr Leu Ser
            20                  25                  30

Gln Gly Ser Pro Arg Cys Asn Leu Lys Glu Asn Leu Leu Lys Asp Asn
        35                  40                  45

Cys Ala Pro Glu Ser Ile Glu Phe Pro Val Ser Glu Ala Gln Ile Leu
    50                  55                  60

Glu Ala Arg Pro Leu Ser Ser Lys Gly Ser Gly Ser Ser Ala Gln Ile
65                  70                  75                  80

Thr Gln Val Ser Pro Gln Arg Ile Val Leu Arg Leu Arg Pro Asp Asp
                85                  90                  95

Ser Lys Ile Phe Ser Leu Gln Val Arg Gln Val Glu Asp Tyr Pro Val
            100                 105                 110

Asp Ile Tyr Tyr Leu Met Asp Leu Ser Phe Ser Met Lys Asp Asp Leu
        115                 120                 125

Ser Ser Ile Gln Thr Leu Gly Thr Lys Leu Ala Ser Gln Met Arg Lys
    130                 135                 140

Leu Thr Ser Asn Leu Arg Ile Gly Phe Gly Ala Phe Val Asp Lys Pro
145                 150                 155                 160

Val Ser Pro Tyr Met Tyr Ile Ser Pro Pro Gln Ala Ile Lys Asn Pro
                165                 170                 175

Cys Tyr Asn Met Lys Asn Ala Cys Leu Pro Met Phe Gly Tyr Lys His
            180                 185                 190

Val Leu Thr Leu Thr Asp Gln Val Ser Arg Phe Asn Glu Glu Val Lys
        195                 200                 205

Lys Gln Ser Val Ser Arg Asn Arg Asp Ala Pro Glu Gly Gly Phe Asp
    210                 215                 220

Ala Ile Met Gln Ala Thr Val Cys Asp Glu Lys Ile Gly Trp Arg Asn
225                 230                 235                 240

Asp Ala Ser His Leu Leu Val Phe Thr Thr Asp Ala Lys Thr His Ile
                245                 250                 255

Ala Leu Asp Gly Arg Leu Ala Gly Ile Val Leu Pro Asn Asp Gly His
            260                 265                 270

Cys His Ile Gly Thr Asp Asn His Tyr Ser Ala Ser Thr Thr Met Asp
        275                 280                 285

Tyr Pro Ser Leu Gly Leu Met Thr Glu Lys Leu Ser Gln Lys Asn Ile
    290                 295                 300

Asn Leu Ile Phe Ala Val Thr Glu Asn Val Val Ser Leu Tyr Gln Asn
305                 310                 315                 320

Tyr Ser Glu Leu Ile Pro Gly Thr Thr Val Gly Val Leu Ser Asp Asp
                325                 330                 335

Ser Ser Asn Val Leu Gln Leu Ile Val Asp Ala Tyr Gly Lys Ile Arg
            340                 345                 350

Ser Lys Val Glu Leu Glu Val Arg Asp Leu Pro Gly Glu Leu Ser Leu
        355                 360                 365

Ser Phe Asn Ala Thr Cys Leu Asn Asn Glu Val Ile Pro Gly Leu Lys
    370                 375                 380

Ser Cys Val Gly Leu Lys Ile Gly Asp Thr Val Ser Phe Ser Ile Glu
```

```
                385                 390                 395                 400
        Ala Lys Val Arg Gly Cys Pro Gln Glu Lys Glu Gln Ser Phe Thr Ile
                        405                 410                 415
        Lys Pro Val Gly Phe Lys Asp Ser Leu Thr Val Gln Val Thr Phe Asp
                        420                 425                 430
        Cys Asp Cys Ala Cys Gln Ala Phe Ala Gln Pro Ser Ser Pro Arg Cys
                        435                 440                 445
        Asn Asn Gly Asn Gly Thr Phe Glu Cys Gly Val Cys Arg Cys Asp Gln
                450                 455                 460
        Gly Trp Leu Gly Ser Met Cys Glu Cys Ser Glu Asp Tyr Arg Pro
        465                 470                 475                 480
        Ser Gln Gln Glu Glu Cys Ser Pro Lys Glu Gly Gln Pro Ile Cys Ser
                            485                 490                 495
        Gln Arg Gly Glu Cys Leu Cys Gly Gln Cys Val Cys His Ser Ser Asp
                        500                 505                 510
        Phe Gly Lys Ile Thr Gly Lys Tyr Cys Glu Cys Asp Asp Phe Ser Cys
                        515                 520                 525
        Val Arg Tyr Lys Gly Glu Met Cys Ser Gly His Gly Gln Cys Asn Cys
                530                 535                 540
        Gly Asp Cys Val Cys Asp Ser Asp Trp Thr Gly Tyr Tyr Cys Asn Cys
        545                 550                 555                 560
        Thr Thr Arg Thr Asp Thr Cys Met Ser Thr Asn Gly Leu Leu Cys Ser
                        565                 570                 575
        Gly Arg Gly Asn Cys Glu Cys Gly Ser Cys Val Cys Val Gln Pro Gly
                        580                 585                 590
        Ser Tyr Gly Asp Thr Cys Glu Lys Cys Pro Thr Cys Pro Asp Ala Cys
                        595                 600                 605
        Ser Phe Lys Lys Glu Cys Val Glu Cys Lys Lys Phe Asn Arg Gly Thr
                        610                 615                 620
        Leu His Glu Glu Asn Thr Cys Ser Arg Tyr Cys Arg Asp Asp Ile Glu
        625                 630                 635                 640
        Gln Val Lys Glu Leu Thr Asp Thr Gly Lys Asn Ala Val Asn Cys Thr
                        645                 650                 655
        Tyr Lys Asn Glu Asp Asp Cys Val Val Arg Phe Gln Tyr Tyr Glu Asp
                        660                 665                 670
        Thr Ser Gly Arg Ala Val Leu Tyr Val Val Glu Glu Pro Glu Cys Pro
                        675                 680                 685
        Lys Gly Pro Asp Ile Leu Val Val Leu Leu Ser Val Met Gly Ala Ile
                        690                 695                 700
        Leu Leu Ile Gly Leu Ala Thr Leu Leu Ile Trp Lys Leu Leu Ile Thr
        705                 710                 715                 720
        Ile His Asp Arg Lys Glu Phe Ala Lys Phe Glu Glu Glu Arg Ala Arg
                        725                 730                 735
        Ala Lys Trp Asp Thr Ala Asn Asn Pro Leu Tyr Lys Glu Ala Thr Ser
                        740                 745                 750
        Thr Phe Thr Asn Ile Thr Tyr Arg Gly Thr
                        755                 760

<210> SEQ ID NO 38
<211> LENGTH: 772
<212> TYPE: PRT
<213> ORGANISM: Homo sapiens

<400> SEQUENCE: 38
```

```
Asn Arg Cys Lys Lys Ala Pro Val Lys Ser Cys Thr Glu Cys Val Arg
1               5                   10                  15

Val Asp Lys Asp Cys Ala Tyr Cys Thr Asp Glu Met Phe Arg Asp Arg
            20                  25                  30

Arg Cys Asn Thr Gln Ala Glu Leu Leu Ala Ala Gly Cys Gln Arg Glu
            35                  40                  45

Ser Ile Val Val Met Glu Ser Ser Phe Gln Ile Thr Glu Glu Thr Gln
    50                  55                  60

Ile Asp Thr Thr Leu Arg Arg Ser Gln Met Ser Pro Gln Gly Leu Arg
65                  70                  75                  80

Val Arg Leu Arg Pro Gly Glu Glu Arg His Phe Glu Leu Glu Val Phe
                85                  90                  95

Glu Pro Leu Glu Ser Pro Val Asp Leu Tyr Ile Leu Met Asp Phe Ser
            100                 105                 110

Asn Ser Met Ser Asp Asp Leu Asp Asn Leu Lys Lys Met Gly Gln Asn
            115                 120                 125

Leu Ala Arg Val Leu Ser Gln Leu Thr Ser Asp Tyr Thr Ile Gly Phe
    130                 135                 140

Gly Lys Phe Val Asp Lys Val Ser Val Pro Gln Thr Asp Met Arg Pro
145                 150                 155                 160

Glu Lys Leu Lys Glu Pro Trp Pro Asn Ser Asp Pro Pro Phe Ser Phe
            165                 170                 175

Lys Asn Val Ile Ser Leu Thr Glu Asp Val Asp Glu Phe Arg Asn Lys
            180                 185                 190

Leu Gln Gly Glu Arg Ile Ser Gly Asn Leu Asp Ala Pro Glu Gly Gly
    195                 200                 205

Phe Asp Ala Ile Leu Gln Thr Ala Val Cys Thr Arg Asp Ile Gly Trp
    210                 215                 220

Arg Pro Asp Ser Thr His Leu Leu Val Phe Ser Thr Glu Ser Ala Phe
225                 230                 235                 240

His Tyr Glu Ala Asp Gly Ala Asn Val Leu Ala Gly Ile Met Ser Arg
            245                 250                 255

Asn Asp Glu Arg Cys His Leu Asp Thr Thr Gly Thr Tyr Thr Gln Tyr
            260                 265                 270

Arg Thr Gln Asp Tyr Pro Ser Val Pro Thr Leu Val Arg Leu Leu Ala
    275                 280                 285

Lys His Asn Ile Ile Pro Ile Phe Ala Val Thr Asn Tyr Ser Tyr Ser
    290                 295                 300

Tyr Tyr Glu Lys Leu His Thr Tyr Phe Pro Val Ser Ser Leu Gly Val
305                 310                 315                 320

Leu Gln Glu Asp Ser Ser Asn Ile Val Glu Leu Leu Glu Glu Ala Phe
            325                 330                 335

Asn Arg Ile Arg Ser Asn Leu Asp Ile Arg Ala Leu Asp Ser Pro Arg
            340                 345                 350

Gly Leu Arg Thr Glu Val Thr Ser Lys Met Phe Gln Lys Thr Arg Thr
            355                 360                 365

Gly Ser Phe His Ile Arg Arg Gly Glu Val Gly Ile Tyr Gln Val Gln
    370                 375                 380

Leu Arg Ala Leu Glu His Val Asp Gly Thr His Val Cys Gln Leu Pro
385                 390                 395                 400

Glu Asp Gln Lys Gly Asn Ile His Leu Lys Pro Ser Phe Ser Asp Gly
            405                 410                 415

Leu Lys Met Asp Ala Gly Ile Ile Cys Asp Val Cys Thr Cys Glu Leu
```

```
            420                 425                 430
Gln Lys Glu Val Arg Ser Ala Arg Cys Ser Phe Asn Gly Asp Phe Val
            435                 440                 445

Cys Gly Gln Cys Val Cys Ser Glu Gly Trp Ser Gly Gln Thr Cys Asn
            450                 455                 460

Cys Ser Thr Gly Ser Leu Ser Asp Ile Gln Pro Cys Leu Arg Glu Gly
465                 470                 475                 480

Glu Asp Lys Pro Cys Ser Gly Arg Gly Glu Cys Gln Cys Gly His Cys
                485                 490                 495

Val Cys Tyr Gly Glu Gly Arg Tyr Glu Gly Gln Phe Cys Glu Tyr Asp
            500                 505                 510

Asn Phe Gln Cys Pro Arg Thr Ser Gly Phe Leu Cys Asn Asp Arg Gly
            515                 520                 525

Arg Cys Ser Met Gly Gln Cys Val Cys Glu Pro Gly Trp Thr Gly Pro
            530                 535                 540

Ser Cys Asp Cys Pro Leu Ser Asn Ala Thr Cys Ile Asp Ser Asn Gly
545                 550                 555                 560

Gly Ile Cys Asn Gly Arg Gly His Cys Glu Cys Gly Arg Cys His Cys
                565                 570                 575

His Gln Gln Ser Leu Tyr Thr Asp Thr Ile Cys Glu Ile Asn Tyr Ser
            580                 585                 590

Ala Ile His Pro Gly Leu Cys Glu Asp Leu Arg Ser Cys Val Gln Cys
            595                 600                 605

Gln Ala Trp Gly Thr Gly Glu Lys Lys Gly Arg Thr Cys Glu Glu Cys
            610                 615                 620

Asn Phe Lys Val Lys Met Val Asp Glu Leu Lys Arg Ala Glu Glu Val
625                 630                 635                 640

Val Val Arg Cys Ser Phe Arg Asp Glu Asp Asp Cys Thr Tyr Ser
                645                 650                 655

Tyr Thr Met Glu Gly Asp Gly Ala Pro Gly Pro Asn Ser Thr Val Leu
            660                 665                 670

Val His Lys Lys Asp Cys Pro Pro Gly Ser Phe Trp Trp Leu Ile
            675                 680                 685

Pro Leu Leu Leu Leu Leu Leu Pro Leu Leu Ala Leu Leu Leu Leu
            690                 695                 700

Cys Trp Lys Tyr Cys Ala Cys Lys Ala Cys Leu Ala Leu Leu Pro
705                 710                 715                 720

Cys Cys Asn Arg Gly His Met Val Gly Phe Lys Glu Asp His Tyr Met
                725                 730                 735

Leu Arg Glu Asn Leu Met Ala Ser Asp His Leu Asp Thr Pro Met Leu
            740                 745                 750

Arg Ser Gly Asn Leu Lys Gly Arg Asp Val Val Arg Trp Lys Val Thr
            755                 760                 765

Asn Asn Met Gln
    770

<210> SEQ ID NO 39
<211> LENGTH: 771
<212> TYPE: PRT
<213> ORGANISM: Mus musculus

<400> SEQUENCE: 39

Asn Arg Cys Lys Lys Ala Gln Val Lys Ser Cys Thr Glu Cys Ile Arg
1               5                   10                  15
```

```
Val Asp Lys Ser Cys Ala Tyr Cys Thr Asp Glu Leu Phe Lys Glu Arg
            20                  25                  30

Arg Cys Asn Thr Gln Ala Asp Val Leu Ala Ala Gly Cys Arg Gly Glu
        35                  40                  45

Ser Ile Leu Val Met Glu Ser Ser Leu Glu Ile Thr Glu Asn Thr Gln
    50                  55                  60

Ile Val Thr Ser Leu His Arg Ser Gln Val Ser Pro Gln Gly Leu Gln
65                  70                  75                  80

Val Arg Leu Arg Arg Gly Glu Glu Arg Thr Phe Val Phe Gln Val Phe
                85                  90                  95

Glu Pro Leu Glu Ser Pro Val Asp Leu Tyr Ile Leu Met Asp Phe Ser
            100                 105                 110

Asn Ser Met Ser Asp Asp Leu Asp Asn Leu Lys Gln Met Gly Gln Asn
        115                 120                 125

Leu Ala Lys Ile Leu Arg Gln Leu Thr Ser Asp Tyr Thr Ile Gly Phe
    130                 135                 140

Gly Lys Phe Val Asp Lys Val Ser Val Pro Gln Thr Asp Met Arg Pro
145                 150                 155                 160

Glu Lys Leu Lys Glu Pro Trp Pro Asn Ser Asp Pro Pro Phe Ser Phe
                165                 170                 175

Lys Asn Val Ile Ser Leu Thr Glu Asn Val Glu Glu Phe Trp Asn Lys
            180                 185                 190

Leu Gln Gly Glu Arg Ile Ser Gly Asn Leu Asp Ala Pro Glu Gly Gly
        195                 200                 205

Phe Asp Ala Ile Leu Gln Thr Ala Val Cys Thr Arg Asp Ile Gly Trp
    210                 215                 220

Arg Ala Asp Ser Thr His Leu Leu Val Phe Ser Thr Glu Ser Ala Phe
225                 230                 235                 240

His Tyr Glu Ala Asp Gly Ala Asn Val Leu Ala Gly Ile Met Asn Arg
                245                 250                 255

Asn Asp Glu Lys Cys His Leu Asp Ala Ser Gly Ala Tyr Thr Gln Tyr
            260                 265                 270

Lys Thr Gln Asp Tyr Pro Ser Val Pro Thr Leu Val Arg Leu Leu Ala
        275                 280                 285

Lys His Asn Ile Ile Pro Ile Phe Ala Val Thr Asn Tyr Ser Tyr Ser
    290                 295                 300

Tyr Tyr Glu Lys Leu His Lys Tyr Phe Pro Val Ser Ser Leu Gly Val
305                 310                 315                 320

Leu Gln Glu Asp Ser Ser Asn Ile Val Glu Leu Leu Glu Glu Ala Phe
                325                 330                 335

Tyr Arg Ile Arg Ser Asn Leu Asp Ile Arg Ala Leu Asp Ser Pro Arg
            340                 345                 350

Gly Leu Arg Thr Glu Val Thr Ser Asp Thr Leu Gln Lys Thr Glu Thr
        355                 360                 365

Gly Ser Phe His Ile Lys Arg Gly Glu Val Gly Thr Tyr Asn Val His
    370                 375                 380

Leu Arg Ala Val Glu Asp Ile Asp Gly Thr His Val Cys Gln Leu Ala
385                 390                 395                 400

Lys Glu Asp Gln Gly Gly Asn Ile His Leu Lys Pro Ser Phe Ser Asp
                405                 410                 415

Gly Leu Arg Met Asp Ala Ser Val Ile Cys Asp Val Cys Pro Cys Glu
            420                 425                 430

Leu Gln Lys Glu Val Arg Ser Ala Arg Cys His Phe Arg Gly Asp Phe
```

```
                    435                 440                 445
Met Cys Gly His Cys Val Cys Asn Glu Gly Trp Ser Gly Lys Thr Cys
            450                 455                 460

Asn Cys Ser Thr Gly Ser Leu Ser Asp Thr Gln Pro Cys Leu Arg Glu
465                 470                 475                 480

Gly Glu Asp Lys Pro Cys Ser Gly His Gly Glu Cys Gln Cys Gly Arg
                485                 490                 495

Cys Val Cys Tyr Gly Glu Gly Arg Tyr Glu Gly His Phe Cys Glu Tyr
            500                 505                 510

Asp Asn Phe Gln Cys Pro Arg Thr Ser Gly Phe Leu Cys Asn Asp Arg
                515                 520                 525

Gly Arg Cys Ser Met Gly Glu Cys Val Cys Glu Pro Gly Trp Thr Gly
            530                 535                 540

Arg Ser Cys Asp Cys Pro Leu Ser Asn Ala Thr Cys Ile Asp Ser Asn
545                 550                 555                 560

Gly Gly Ile Cys Asn Gly Arg Gly Tyr Cys Glu Cys Gly Arg Cys His
                565                 570                 575

Cys Asn Gln Gln Ser Leu Tyr Thr Asp Thr Thr Cys Glu Ile Asn Tyr
            580                 585                 590

Ser Ala Ile Leu Gly Leu Cys Glu Asp Leu Arg Ser Cys Val Gln Cys
                595                 600                 605

Gln Ala Trp Gly Thr Gly Glu Lys Lys Gly Arg Ala Cys Asp Asp Cys
            610                 615                 620

Pro Phe Lys Val Lys Met Val Asp Glu Leu Lys Lys Glu Glu Val Val
625                 630                 635                 640

Glu Tyr Cys Ser Phe Arg Asp Glu Asp Asp Cys Thr Tyr Ser Tyr
                645                 650                 655

Asn Val Glu Gly Asp Gly Ser Pro Gly Pro Asn Ser Thr Val Leu Val
                660                 665                 670

His Lys Lys Lys Asp Cys Leu Pro Ala Pro Ser Trp Trp Leu Ile Pro
            675                 680                 685

Leu Leu Ile Phe Leu Leu Leu Leu Ala Leu Leu Leu Leu Leu Cys
690                 695                 700

Trp Lys Tyr Cys Ala Cys Cys Lys Ala Cys Leu Gly Leu Leu Pro Cys
705                 710                 715                 720

Cys Asn Arg Gly His Met Val Gly Phe Lys Glu Asp His Tyr Met Leu
                725                 730                 735

Arg Glu Asn Leu Met Ala Ser Asp His Leu Asp Thr Pro Met Leu Arg
            740                 745                 750

Ser Gly Asn Leu Lys Gly Arg Asp Thr Val Arg Trp Lys Ile Thr Asn
            755                 760                 765

Asn Val Gln
    770

<210> SEQ ID NO 40
<211> LENGTH: 775
<212> TYPE: PRT
<213> ORGANISM: Homo sapiens

<400> SEQUENCE: 40

Gly Leu Asn Ile Cys Thr Ser Gly Ser Ala Thr Ser Cys Glu Glu Cys
1               5                   10                  15

Leu Leu Ile His Pro Lys Cys Ala Trp Cys Ser Lys Glu Asp Phe Gly
                20                  25                  30
```

```
Ser Pro Arg Ser Ile Thr Ser Arg Cys Asp Leu Arg Ala Asn Leu Val
        35                  40                  45
Lys Asn Gly Cys Gly Gly Glu Ile Glu Ser Pro Ala Ser Ser Phe His
 50                  55                  60
Val Leu Arg Ser Leu Pro Leu Ser Ser Lys Gly Ser Gly Ser Ala Gly
 65                  70                  75                  80
Trp Asp Val Ile Gln Met Thr Pro Gln Glu Ile Ala Val Asn Leu Arg
                 85                  90                  95
Pro Gly Asp Lys Thr Thr Phe Gln Leu Gln Val Arg Gln Val Glu Tyr
                100                 105                 110
Pro Val Asp Leu Tyr Tyr Leu Met Asp Leu Ser Leu Ser Met Lys Asp
            115                 120                 125
Asp Leu Asp Asn Ile Arg Ser Leu Gly Thr Lys Leu Ala Glu Glu Met
    130                 135                 140
Arg Lys Leu Thr Ser Asn Phe Arg Leu Gly Phe Gly Ser Phe Val Asp
145                 150                 155                 160
Lys Asp Ile Ser Pro Phe Ser Tyr Thr Ala Pro Arg Tyr Gln Thr Asn
                165                 170                 175
Pro Cys Ile Gly Tyr Lys Leu Phe Pro Asn Cys Val Pro Ser Phe Gly
            180                 185                 190
Phe Arg His Leu Leu Pro Leu Thr Asp Arg Val Asp Ser Phe Asn Glu
        195                 200                 205
Glu Val Arg Lys Gln Arg Val Ser Arg Asn Arg Asp Ala Pro Glu Gly
    210                 215                 220
Gly Phe Asp Ala Val Leu Gln Ala Ala Val Cys Lys Glu Lys Ile Gly
225                 230                 235                 240
Trp Arg Lys Asp Ala Leu His Leu Leu Val Phe Thr Thr Asp Asp Val
                245                 250                 255
Pro His Ile Ala Leu Asp Gly Lys Leu Gly Gly Leu Val Gln Pro His
            260                 265                 270
Asp Gly Gln Cys His Leu Asn Glu Ala Asn Glu Tyr Thr Ala Ser Asn
        275                 280                 285
Gln Met Asp Tyr Pro Ser Leu Ala Leu Leu Gly Glu Lys Leu Ala Glu
    290                 295                 300
Asn Asn Ile Asn Leu Ile Phe Ala Val Thr Lys Asn His Tyr Met Leu
305                 310                 315                 320
Tyr Lys Asn Phe Thr Ala Leu Ile Pro Gly Thr Thr Val Glu Ile Leu
                325                 330                 335
Asp Gly Asp Ser Lys Asn Ile Ile Gln Leu Ile Ile Asn Ala Tyr Asn
            340                 345                 350
Ser Ile Arg Ser Lys Val Glu Leu Ser Val Trp Asp Gln Pro Glu Asp
        355                 360                 365
Leu Asn Leu Phe Phe Thr Ala Thr Cys Gln Asp Gly Val Ser Tyr Pro
    370                 375                 380
Gly Gln Arg Lys Cys Glu Gly Leu Lys Ile Gly Asp Thr Ala Ser Phe
385                 390                 395                 400
Glu Val Ser Leu Glu Ala Arg Ser Cys Pro Ser Arg His Thr Glu His
                405                 410                 415
Val Phe Ala Leu Arg Pro Val Gly Phe Arg Asp Ser Leu Glu Val Gly
            420                 425                 430
Val Thr Tyr Asn Cys Thr Cys Gly Cys Ser Val Gly Leu Glu Pro Asn
        435                 440                 445
Ser Ala Arg Cys Asn Gly Ser Gly Thr Tyr Val Cys Gly Leu Cys Glu
```

```
                    450                 455                 460
Cys Ser Pro Gly Tyr Leu Gly Thr Arg Cys Glu Cys Gln Asp Gly Glu
465                 470                 475                 480

Asn Gln Ser Val Tyr Gln Asn Leu Cys Arg Glu Ala Glu Gly Lys Pro
                485                 490                 495

Leu Cys Ser Gly Arg Gly Asp Cys Ser Cys Asn Gln Cys Ser Cys Phe
            500                 505                 510

Glu Ser Glu Phe Gly Lys Ile Tyr Gly Pro Phe Cys Gly Cys Asp Asn
        515                 520                 525

Phe Ser Cys Ala Arg Asn Lys Gly Val Leu Cys Ser Gly His Gly Glu
    530                 535                 540

Cys His Cys Gly Glu Cys Lys Cys His Ala Gly Tyr Ile Gly Asp Asn
545                 550                 555                 560

Cys Asn Cys Ser Thr Asp Ile Ser Thr Cys Arg Gly Arg Asp Gly Gln
                565                 570                 575

Ile Cys Ser Glu Arg Gly His Cys Leu Cys Gly Gln Cys Gln Cys Thr
            580                 585                 590

Glu Pro Gly Ala Phe Gly Glu Met Cys Glu Lys Cys Pro Thr Cys Pro
        595                 600                 605

Asp Ala Cys Ser Thr Lys Arg Asp Cys Val Glu Cys Pro Leu Leu His
    610                 615                 620

Ser Gly Lys Pro Asp Asn Gln Thr Cys His Ser Leu Cys Arg Asp Glu
625                 630                 635                 640

Val Ile Thr Trp Val Asp Thr Ile Val Lys Asp Asp Gln Glu Ala Val
                645                 650                 655

Leu Cys Phe Tyr Lys Thr Ala Lys Asp Cys Val Met Met Phe Thr Tyr
            660                 665                 670

Val Glu Leu Pro Ser Gly Lys Ser Asn Leu Thr Val Leu Arg Glu Pro
        675                 680                 685

Glu Cys Gly Asn Thr Pro Asn Ala Met Thr Ile Leu Leu Ala Val Val
    690                 695                 700

Gly Ser Ile Leu Leu Val Gly Leu Ala Leu Leu Ala Ile Trp Lys Leu
705                 710                 715                 720

Leu Val Thr Ile His Asp Arg Arg Glu Phe Ala Lys Phe Gln Ser Glu
                725                 730                 735

Arg Ser Arg Ala Arg Tyr Glu Met Ala Ser Asn Pro Leu Tyr Arg Lys
            740                 745                 750

Pro Ile Ser Thr His Thr Val Asp Phe Thr Phe Asn Lys Phe Asn Lys
        755                 760                 765

Ser Tyr Asn Gly Thr Val Asp
        770                 775

<210> SEQ ID NO 41
<211> LENGTH: 776
<212> TYPE: PRT
<213> ORGANISM: Mus musculus

<400> SEQUENCE: 41

Gly Leu Asn Ile Cys Thr Ser Gly Ser Ala Thr Ser Cys Glu Glu Cys
1               5                   10                  15

Leu Leu Ile His Pro Lys Cys Ala Trp Cys Ser Lys Glu Tyr Phe Gly
                20                  25                  30

Asn Pro Arg Ser Ile Thr Ser Arg Cys Asp Leu Lys Ala Asn Leu Ile
            35                  40                  45
```

```
Arg Asn Gly Cys Glu Gly Glu Ile Glu Ser Pro Ala Ser Ser Thr His
 50                  55                  60
Val Leu Arg Asn Leu Pro Leu Ser Cys Lys Gly Ser Ser Ala Thr Gly
 65                  70                  75                  80
Ser Asp Val Ile Gln Met Thr Pro Gln Glu Ile Ala Val Ser Leu Arg
                 85                  90                  95
Pro Gly Glu Gln Thr Thr Phe Gln Leu Gln Val Arg Gln Val Glu Asp
            100                 105                 110
Tyr Pro Val Asp Leu Tyr Tyr Leu Met Asp Leu Ser Leu Ser Met Lys
            115                 120                 125
Asp Asp Leu Glu Asn Ile Arg Ser Leu Gly Thr Lys Leu Ala Glu Glu
130                 135                 140
Met Arg Lys Leu Thr Ser Asn Phe Arg Leu Gly Phe Gly Ser Phe Val
145                 150                 155                 160
Asp Lys Asp Ile Ser Pro Phe Ser Tyr Thr Ala Pro Arg Tyr Gln Thr
                165                 170                 175
Asn Pro Cys Ile Gly Tyr Lys Leu Phe Pro Asn Cys Val Pro Ser Phe
            180                 185                 190
Gly Phe Arg His Leu Leu Pro Leu Thr Asp Arg Val Asp Ser Phe Asn
            195                 200                 205
Glu Glu Val Arg Lys Gln Arg Val Ser Arg Asn Arg Asp Ala Pro Glu
210                 215                 220
Gly Gly Phe Asp Ala Val Leu Gln Ala Ala Val Cys Lys Glu Lys Ile
225                 230                 235                 240
Gly Trp Arg Lys Asp Ala Leu His Leu Leu Val Phe Thr Thr Asp Asp
                245                 250                 255
Val Pro His Ile Ala Leu Asp Gly Lys Leu Gly Gly Leu Val Gln Pro
            260                 265                 270
His Asp Gly Gln Cys His Leu Asn Glu Ala Asn Glu Tyr Thr Ala Ser
            275                 280                 285
Asn Gln Met Asp Tyr Pro Ser Leu Ala Leu Leu Gly Glu Lys Leu Ala
290                 295                 300
Glu Asn Asn Ile Asn Leu Ile Phe Ala Val Thr Lys Asn His Tyr Met
305                 310                 315                 320
Leu Tyr Lys Asn Phe Thr Ala Leu Ile Pro Gly Thr Thr Val Glu Ile
                325                 330                 335
Leu His Gly Asp Ser Lys Asn Ile Ile Gln Leu Ile Ile Asn Ala Tyr
            340                 345                 350
Ser Ser Ile Arg Ala Lys Val Glu Leu Ser Val Trp Asp Gln Pro Glu
            355                 360                 365
Asp Leu Asn Leu Phe Phe Thr Ala Thr Cys Gln Asp Gly Ile Ser Tyr
370                 375                 380
Pro Gly Gln Arg Lys Cys Glu Gly Leu Lys Ile Gly Asp Thr Ala Ser
385                 390                 395                 400
Phe Glu Val Ser Val Glu Ala Arg Ser Cys Pro Gly Arg Gln Ala Ala
                405                 410                 415
Gln Ser Phe Thr Leu Arg Pro Val Gly Phe Arg Asp Ser Leu Gln Val
            420                 425                 430
Glu Val Ala Tyr Asn Cys Thr Cys Gly Cys Ser Thr Gly Leu Glu Pro
            435                 440                 445
Asn Ser Ala Arg Cys Ser Gly Asn Gly Thr Tyr Thr Cys Gly Leu Cys
450                 455                 460
Glu Cys Asp Pro Gly Tyr Leu Gly Thr Arg Cys Glu Cys Gln Glu Gly
```

Glu Asn Gln Ser Gly Tyr Gln Asn Leu Cys Arg Glu Ala Gly Lys
465                 470                 475                 480
                485                 490                 495

Pro Leu Cys Ser Gly Arg Gly Glu Cys Ser Cys Asn Gln Cys Ser Cys
                500                 505                 510

Phe Glu Ser Glu Phe Gly Arg Ile Tyr Gly Pro Phe Cys Glu Cys Asp
            515                 520                 525

Ser Phe Ser Cys Ala Arg Asn Lys Gly Val Leu Cys Ser Gly His Gly
        530                 535                 540

Glu Cys His Cys Gly Glu Cys Lys Cys His Ala Gly Tyr Ile Gly Asp
545                 550                 555                 560

Asn Cys Asn Cys Ser Thr Asp Val Ser Thr Cys Arg Ala Lys Asp Gly
                565                 570                 575

Gln Ile Cys Ser Asp Arg Gly Arg Cys Val Cys Gly Gln Cys Gln Cys
            580                 585                 590

Thr Glu Pro Gly Ala Phe Gly Glu Thr Cys Glu Lys Cys Pro Thr Cys
        595                 600                 605

Pro Asp Ala Cys Ser Ser Lys Arg Asp Cys Val Glu Cys Leu Leu Leu
610                 615                 620

His Gln Gly Lys Pro Asp Asn Gln Thr Cys His His Gln Cys Lys Asp
625                 630                 635                 640

Glu Val Ile Thr Trp Val Asp Thr Ile Val Lys Asp Asp Gln Glu Ala
                645                 650                 655

Val Leu Cys Phe Tyr Lys Thr Ala Lys Asp Cys Val Met Met Phe Ser
            660                 665                 670

Tyr Thr Glu Leu Pro Asn Gly Arg Ser Asn Leu Thr Val Leu Arg Glu
        675                 680                 685

Pro Glu Cys Gly Ser Ala Pro Asn Ala Met Thr Ile Leu Leu Ala Val
            690                 695                 700

Val Gly Ser Ile Leu Leu Ile Gly Met Ala Leu Leu Ala Ile Trp Lys
705                 710                 715                 720

Leu Leu Val Thr Ile His Asp Arg Arg Glu Phe Ala Lys Phe Gln Ser
                725                 730                 735

Glu Arg Ser Arg Ala Arg Tyr Glu Met Ala Ser Asn Pro Leu Tyr Arg
            740                 745                 750

Lys Pro Ile Ser Thr His Thr Val Asp Phe Ala Phe Asn Lys Phe Asn
        755                 760                 765

Lys Ser Tyr Asn Gly Ser Val Asp
770                 775

<210> SEQ ID NO 42
<211> LENGTH: 771
<212> TYPE: PRT
<213> ORGANISM: Homo sapiens

<400> SEQUENCE: 42

His Val Gln Gly Gly Cys Ala Leu Gly Gly Ala Glu Thr Cys Glu Asp
1               5                   10                  15

Cys Leu Leu Ile Gly Pro Gln Cys Ala Trp Cys Ala Gln Glu Asn Phe
                20                  25                  30

Thr His Pro Ser Gly Val Gly Glu Arg Cys Asp Thr Pro Ala Asn Leu
            35                  40                  45

Leu Ala Lys Gly Cys Gln Leu Asn Phe Ile Glu Asn Pro Val Ser Gln
        50                  55                  60

Val Glu Ile Leu Lys Asn Lys Pro Leu Ser Val Gly Arg Gln Lys Asn
65                  70                  75                  80

Ser Ser Asp Ile Val Gln Ile Ala Pro Gln Ser Leu Ile Leu Lys Leu
            85                  90                  95

Arg Pro Gly Gly Ala Gln Thr Leu Gln Val His Val Arg Gln Thr Glu
            100                 105                 110

Asp Tyr Pro Val Asp Leu Tyr Tyr Leu Met Asp Leu Ser Ala Ser Met
            115                 120                 125

Asp Asp Asp Leu Asn Thr Ile Lys Glu Leu Gly Ser Arg Leu Ser Lys
        130                 135                 140

Glu Met Ser Lys Leu Thr Ser Asn Phe Arg Leu Gly Phe Gly Ser Phe
145                 150                 155                 160

Val Glu Lys Pro Val Ser Pro Phe Val Lys Thr Thr Pro Glu Glu Ile
                165                 170                 175

Ala Asn Pro Cys Ser Ser Ile Pro Tyr Phe Cys Leu Pro Thr Phe Gly
            180                 185                 190

Phe Lys His Ile Leu Pro Leu Thr Asn Asp Ala Glu Arg Phe Asn Glu
            195                 200                 205

Ile Val Lys Asn Gln Lys Ile Ser Ala Asn Ile Asp Thr Pro Glu Gly
        210                 215                 220

Gly Phe Asp Ala Ile Met Gln Ala Ala Val Cys Lys Glu Lys Ile Gly
225                 230                 235                 240

Trp Arg Asn Asp Ser Leu His Leu Leu Val Phe Val Ser Asp Ala Asp
                245                 250                 255

Ser His Phe Gly Met Asp Ser Lys Leu Ala Gly Ile Val Ile Pro Asn
            260                 265                 270

Asp Gly Leu Cys His Leu Asp Ser Lys Asn Glu Tyr Ser Met Ser Thr
        275                 280                 285

Val Leu Glu Tyr Pro Thr Ile Gly Gln Leu Ile Asp Lys Leu Val Gln
290                 295                 300

Asn Asn Val Leu Leu Ile Phe Ala Val Thr Gln Glu Gln Val His Leu
305                 310                 315                 320

Tyr Glu Asn Tyr Ala Lys Leu Ile Pro Gly Ala Thr Val Gly Leu Leu
                325                 330                 335

Gln Lys Asp Ser Gly Asn Ile Leu Gln Leu Ile Ile Ser Ala Tyr Glu
            340                 345                 350

Glu Leu Arg Ser Glu Val Glu Leu Glu Val Leu Gly Asp Thr Glu Gly
            355                 360                 365

Leu Asn Leu Ser Phe Thr Ala Ile Cys Asn Asn Gly Thr Leu Phe Gln
        370                 375                 380

His Gln Lys Lys Cys Ser His Met Lys Val Gly Asp Thr Ala Ser Phe
385                 390                 395                 400

Ser Val Thr Val Asn Ile Pro His Cys Glu Arg Arg Ser Arg His Ile
                405                 410                 415

Ile Ile Lys Pro Val Gly Leu Gly Asp Ala Leu Glu Leu Leu Val Ser
            420                 425                 430

Pro Glu Cys Asn Cys Asp Cys Gln Lys Glu Val Glu Val Asn Ser Ser
            435                 440                 445

Lys Cys His His Gly Asn Gly Ser Phe Gln Cys Gly Val Cys Ala Cys
        450                 455                 460

His Pro Gly His Met Gly Pro Arg Cys Glu Cys Gly Glu Asp Met Leu
465                 470                 475                 480

Ser Thr Asp Ser Cys Lys Glu Ala Pro Asp His Pro Ser Cys Ser Gly

```
            485                 490                 495
Arg Gly Asp Cys Tyr Cys Gly Gln Cys Ile Cys His Leu Ser Pro Tyr
            500                 505                 510

Gly Asn Ile Tyr Gly Pro Tyr Cys Gln Cys Asp Asn Phe Ser Cys Val
            515                 520                 525

Arg His Lys Gly Leu Leu Cys Gly Gly Asn Gly Asp Cys Asp Cys Gly
            530                 535                 540

Glu Cys Val Cys Arg Ser Gly Trp Thr Gly Glu Tyr Cys Asn Cys Thr
545                 550                 555                 560

Thr Ser Thr Asp Ser Cys Val Ser Glu Asp Gly Val Leu Cys Ser Gly
            565                 570                 575

Arg Gly Asp Cys Val Cys Gly Lys Cys Val Cys Thr Asn Pro Gly Ala
            580                 585                 590

Ser Gly Pro Thr Cys Glu Arg Cys Pro Thr Cys Gly Asp Pro Cys Asn
            595                 600                 605

Ser Lys Arg Ser Cys Ile Glu Cys His Leu Ser Ala Ala Gly Gln Ala
            610                 615                 620

Arg Glu Glu Cys Val Asp Lys Cys Lys Leu Ala Gly Ala Thr Ile Ser
625                 630                 635                 640

Glu Glu Glu Asp Phe Ser Lys Asp Gly Ser Val Ser Cys Ser Leu Gln
                    645                 650                 655

Gly Glu Asn Glu Cys Leu Ile Thr Phe Leu Ile Thr Thr Asp Asn Glu
            660                 665                 670

Gly Lys Thr Ile Ile His Ser Ile Asn Glu Lys Asp Cys Pro Lys Pro
            675                 680                 685

Pro Asn Ile Pro Met Ile Met Leu Gly Val Ser Leu Ala Ile Leu Leu
690                 695                 700

Ile Gly Val Val Leu Leu Cys Ile Trp Lys Leu Leu Val Ser Phe His
705                 710                 715                 720

Asp Arg Lys Glu Val Ala Lys Phe Glu Ala Glu Arg Ser Lys Ala Lys
                    725                 730                 735

Trp Gln Thr Gly Thr Asn Pro Leu Tyr Arg Gly Ser Thr Ser Thr Phe
            740                 745                 750

Lys Asn Val Thr Tyr Lys His Arg Glu Lys Gln Lys Val Asp Leu Ser
            755                 760                 765

Thr Asp Cys
    770

<210> SEQ ID NO 43
<211> LENGTH: 770
<212> TYPE: PRT
<213> ORGANISM: Mus musculus

<400> SEQUENCE: 43

His Val Gln Gly Gly Cys Ala Trp Gly Gly Ala Glu Ser Cys Ser Asp
1               5                   10                  15

Cys Leu Leu Thr Gly Pro His Cys Ala Trp Cys Ser Gln Glu Asn Phe
            20                  25                  30

Thr His Leu Ser Gly Ala Gly Glu Arg Cys Asp Thr Pro Ala Asn Leu
        35                  40                  45

Leu Ala Lys Gly Cys Gln Leu Pro Phe Ile Glu Asn Pro Val Ser Arg
    50                  55                  60

Ile Glu Val Leu Gln Asn Lys Pro Leu Ser Val Gly Arg Gln Lys Asn
65                  70                  75                  80
```

```
Ser Ser Asp Ile Val Gln Ile Ala Pro Gln Ser Leu Val Leu Lys Leu
            85                  90                  95

Arg Pro Gly Arg Glu Gln Thr Leu Gln Val Gln Val Arg Gln Thr Glu
100                 105                 110

Asp Tyr Pro Val Asp Leu Tyr Tyr Leu Met Asp Leu Ser Ala Ser Met
            115                 120                 125

Asp Asp Asp Leu Asn Thr Ile Lys Glu Leu Gly Ser Arg Leu Ala Lys
130                 135                 140

Glu Met Ser Lys Leu Thr Ser Asn Phe Arg Leu Gly Phe Gly Ser Phe
145                 150                 155                 160

Val Glu Lys Pro Val Ser Pro Phe Met Lys Thr Thr Pro Glu Glu Ile
            165                 170                 175

Thr Asn Pro Cys Ser Ser Ile Pro Tyr Phe Cys Leu Pro Thr Phe Gly
            180                 185                 190

Phe Lys His Ile Leu Pro Leu Thr Asp Asp Ala Glu Arg Phe Asn Glu
            195                 200                 205

Ile Val Arg Lys Gln Lys Ile Ser Ala Asn Ile Asp Thr Pro Glu Gly
            210                 215                 220

Gly Phe Asp Ala Ile Met Gln Ala Ala Val Cys Lys Glu Lys Ile Gly
225                 230                 235                 240

Trp Arg Asn Asp Ser Leu His Leu Leu Val Phe Val Ser Asp Ala Asp
                245                 250                 255

Ser His Phe Gly Met Asp Ser Lys Leu Ala Gly Ile Val Ile Pro Asn
            260                 265                 270

Asp Gly Leu Cys His Leu Asp His Arg Asn Glu Tyr Ser Met Ser Thr
            275                 280                 285

Val Leu Glu Tyr Pro Thr Ile Gly Gln Leu Ile Asp Lys Leu Val Gln
            290                 295                 300

Asn Asn Val Leu Leu Ile Phe Ala Val Thr Gln Glu Gln Val His Leu
305                 310                 315                 320

Tyr Glu Asn Tyr Ala Lys Leu Ile Pro Gly Ala Thr Val Gly Leu Leu
            325                 330                 335

Gln Lys Asp Ser Gly Asn Ile Leu Gln Leu Ile Ile Ser Ala Tyr Glu
            340                 345                 350

Glu Leu Arg Ser Glu Val Glu Leu Glu Val Leu Gly Asp Thr Glu Gly
            355                 360                 365

Leu Asn Leu Ser Phe Thr Ala Leu Cys Asn Asn Gly Val Leu Phe Pro
            370                 375                 380

His Gln Lys Lys Cys Ser His Met Lys Val Gly Asp Thr Ala Ser Phe
385                 390                 395                 400

Asn Val Thr Val Ser Val Ser Asn Cys Glu Lys Arg Ser Arg Asn Leu
                405                 410                 415

Ile Ile Lys Pro Val Gly Leu Gly Asp Thr Leu Glu Ile Leu Val Ser
            420                 425                 430

Ala Glu Cys Asp Cys Asp Cys Gln Arg Glu Ile Glu Thr Asn Ser Ser
            435                 440                 445

Lys Cys His Asn Gly Asn Gly Ser Phe Gln Cys Gly Val Cys Thr Cys
            450                 455                 460

Asn Pro Gly His Met Gly Pro His Cys Glu Cys Gly Glu Asp Met Val
465                 470                 475                 480

Ser Thr Asp Ser Cys Lys Glu Ser Pro Gly His Pro Ser Cys Ser Gly
            485                 490                 495

Arg Gly Asp Cys Tyr Cys Gly Gln Cys Ile Cys His Leu Ser Pro Tyr
```

```
                    500                 505                 510
Gly Ser Ile Tyr Gly Pro Tyr Cys Gln Cys Asp Asn Phe Ser Cys Leu
        515                 520                 525

Arg His Lys Gly Leu Leu Cys Gly Asp Asn Gly Asp Cys Asp Cys Gly
        530                 535                 540

Glu Cys Val Cys Arg Asp Gly Trp Thr Gly Glu Tyr Cys Asn Cys Thr
545                 550                 555                 560

Thr Asn Arg Asp Ser Cys Thr Ser Glu Asp Gly Val Leu Cys Ser Gly
                565                 570                 575

Arg Gly Asp Cys Val Cys Gly Lys Cys Val Cys Arg Asn Pro Gly Ala
            580                 585                 590

Ser Gly Pro Thr Cys Glu Arg Cys Pro Thr Cys Gly Asp Pro Cys Asn
        595                 600                 605

Ser Lys Arg Ser Cys Ile Glu Cys Tyr Leu Ser Ala Asp Gly Gln Ala
    610                 615                 620

Gln Glu Glu Cys Ala Asp Lys Cys Lys Ala Ile Gly Ala Thr Ile Ser
625                 630                 635                 640

Glu Glu Asp Phe Ser Lys Asp Thr Ser Val Ser Cys Ser Leu Gln Gly
                645                 650                 655

Glu Asn Glu Cys Leu Ile Thr Phe Leu Ile Thr Thr Asp Asn Glu Gly
            660                 665                 670

Lys Thr Ile Ile His Asn Ile Asn Glu Lys Asp Cys Pro Lys Pro Pro
        675                 680                 685

Asn Ile Pro Met Ile Met Leu Gly Val Ser Leu Ala Ile Leu Leu Ile
    690                 695                 700

Gly Val Val Leu Leu Cys Ile Trp Lys Leu Leu Val Ser Phe His Asp
705                 710                 715                 720

Arg Lys Glu Val Ala Lys Phe Glu Ala Glu Arg Ser Lys Ala Lys Trp
                725                 730                 735

Gln Thr Gly Thr Asn Pro Leu Tyr Arg Gly Ser Thr Ser Thr Phe Lys
            740                 745                 750

Asn Val Thr Tyr Lys His Arg Glu Lys His Lys Ala Gly Leu Ser Ser
        755                 760                 765

Asp Gly
    770

<210> SEQ ID NO 44
<211> LENGTH: 779
<212> TYPE: PRT
<213> ORGANISM: Homo sapiens

<400> SEQUENCE: 44

Glu Leu Asp Ala Lys Ile Pro Ser Thr Gly Asp Ala Thr Glu Trp Arg
1               5                   10                  15

Asn Pro His Leu Ser Met Leu Gly Ser Cys Gln Pro Ala Pro Ser Cys
            20                  25                  30

Gln Lys Cys Ile Leu Ser His Pro Ser Cys Ala Trp Cys Lys Gln Leu
        35                  40                  45

Asn Phe Thr Ala Ser Gly Glu Ala Glu Ala Arg Arg Cys Ala Arg Arg
    50                  55                  60

Glu Glu Leu Leu Ala Arg Gly Cys Pro Leu Glu Glu Leu Glu Glu Pro
65                  70                  75                  80

Arg Gly Gln Gln Glu Val Leu Gln Asp Gln Pro Leu Ser Gln Gly Ala
                85                  90                  95
```

```
Arg Gly Glu Gly Ala Thr Gln Leu Ala Pro Gln Arg Val Arg Val Thr
                100                 105                 110

Leu Arg Pro Gly Glu Pro Gln Gln Leu Gln Val Arg Phe Leu Arg Ala
        115                 120                 125

Glu Gly Tyr Pro Val Asp Leu Tyr Tyr Leu Met Asp Leu Ser Tyr Ser
    130                 135                 140

Met Lys Asp Asp Leu Glu Arg Val Arg Gln Leu Gly His Ala Leu Leu
145                 150                 155                 160

Val Arg Leu Gln Glu Val Thr His Ser Val Arg Ile Gly Phe Gly Ser
                165                 170                 175

Phe Val Asp Lys Thr Val Leu Pro Phe Val Ser Thr Val Pro Ser Lys
        180                 185                 190

Leu Arg His Pro Cys Pro Thr Arg Leu Glu Arg Cys Gln Ser Pro Phe
    195                 200                 205

Ser Phe His His Val Leu Ser Leu Thr Gly Asp Ala Gln Ala Phe Glu
    210                 215                 220

Arg Glu Val Gly Arg Gln Ser Val Ser Gly Asn Leu Asp Ser Pro Glu
225                 230                 235                 240

Gly Gly Phe Asp Ala Ile Leu Gln Ala Ala Leu Cys Gln Glu Gln Ile
                245                 250                 255

Gly Trp Arg Asn Val Ser Arg Leu Leu Val Phe Thr Ser Asp Asp Thr
        260                 265                 270

Phe His Thr Ala Gly Asp Gly Lys Leu Gly Gly Ile Phe Met Pro Ser
    275                 280                 285

Asp Gly His Cys His Leu Asp Ser Asn Gly Leu Tyr Ser Arg Ser Thr
    290                 295                 300

Glu Phe Asp Tyr Pro Ser Val Gly Gln Val Ala Gln Ala Leu Ser Ala
305                 310                 315                 320

Ala Asn Ile Gln Pro Ile Phe Ala Val Thr Ser Ala Ala Leu Pro Val
                325                 330                 335

Tyr Gln Glu Leu Ser Lys Leu Ile Pro Lys Ser Ala Val Gly Glu Leu
        340                 345                 350

Ser Glu Asp Ser Ser Asn Val Val Gln Leu Ile Met Asp Ala Tyr Asn
    355                 360                 365

Ser Leu Ser Ser Thr Val Thr Leu Glu His Ser Ser Leu Pro Pro Gly
    370                 375                 380

Val His Ile Ser Tyr Glu Ser Gln Cys Glu Gly Pro Glu Lys Arg Glu
385                 390                 395                 400

Gly Lys Ala Glu Asp Arg Gly Gln Cys Asn His Val Arg Ile Asn Gln
                405                 410                 415

Thr Val Thr Phe Trp Val Ser Leu Gln Ala Thr His Cys Leu Pro Glu
        420                 425                 430

Pro His Leu Leu Arg Leu Arg Ala Leu Gly Phe Ser Glu Glu Leu Ile
    435                 440                 445

Val Glu Leu His Thr Leu Cys Asp Cys Asn Cys Ser Asp Thr Gln Pro
    450                 455                 460

Gln Ala Pro His Cys Ser Asp Gly Gln Gly His Leu Gln Cys Gly Val
465                 470                 475                 480

Cys Ser Cys Ala Pro Gly Arg Leu Gly Arg Leu Cys Glu Cys Ser Val
                485                 490                 495

Ala Glu Leu Ser Ser Pro Asp Leu Glu Ser Gly Cys Arg Ala Pro Asn
        500                 505                 510

Gly Thr Gly Pro Leu Cys Ser Gly Lys Gly His Cys Gln Cys Gly Arg
```

```
                515                 520                 525
Cys Ser Cys Ser Gly Gln Ser Ser Gly His Leu Cys Glu Cys Asp Asp
        530                 535                 540
Ala Ser Cys Glu Arg His Glu Gly Ile Leu Cys Gly Gly Phe Gly Arg
545                 550                 555                 560
Cys Gln Cys Gly Val Cys His Cys His Ala Asn Arg Thr Gly Arg Ala
                565                 570                 575
Cys Glu Cys Ser Gly Asp Met Asp Ser Cys Ile Ser Pro Glu Gly Gly
        580                 585                 590
Leu Cys Ser Gly His Gly Arg Cys Lys Cys Asn Arg Cys Gln Cys Leu
            595                 600                 605
Asp Gly Tyr Tyr Gly Ala Leu Cys Asp Gln Cys Pro Gly Cys Lys Thr
        610                 615                 620
Pro Cys Glu Arg His Arg Asp Cys Ala Glu Cys Gly Ala Phe Arg Thr
625                 630                 635                 640
Gly Pro Leu Ala Thr Asn Cys Ser Thr Ala Cys Ala His Thr Asn Val
                645                 650                 655
Thr Leu Ala Leu Ala Pro Ile Leu Asp Asp Gly Trp Cys Lys Glu Arg
        660                 665                 670
Thr Leu Asp Asn Gln Leu Phe Phe Phe Leu Val Glu Asp Asp Ala Arg
            675                 680                 685
Gly Thr Val Val Leu Arg Val Arg Pro Gln Glu Lys Gly Ala Asp His
        690                 695                 700
Thr Gln Ala Ile Val Leu Gly Cys Val Gly Gly Ile Val Ala Val Gly
705                 710                 715                 720
Leu Gly Leu Val Leu Ala Tyr Arg Leu Ser Val Glu Ile Tyr Asp Arg
                725                 730                 735
Arg Glu Tyr Ser Arg Phe Glu Lys Glu Gln Gln Gln Leu Asn Trp Lys
        740                 745                 750
Gln Asp Ser Asn Pro Leu Tyr Lys Ser Ala Ile Thr Thr Thr Ile Asn
            755                 760                 765
Pro Arg Phe Gln Glu Ala Asp Ser Pro Thr Leu
        770                 775

<210> SEQ ID NO 45
<211> LENGTH: 786
<212> TYPE: PRT
<213> ORGANISM: Mus musculus

<400> SEQUENCE: 45

Glu Leu Asp Thr Lys Ile Thr Ser Ser Gly Glu Ala Ala Glu Trp Glu
1               5                   10                  15
Asp Pro Asp Leu Ser Leu Gln Gly Ser Cys Gln Pro Val Pro Ser Cys
            20                  25                  30
Gln Lys Cys Ile Leu Ser His Pro Ser Cys Ala Trp Cys Lys Gln Leu
        35                  40                  45
Asn Phe Thr Ala Ser Gly Glu Ala Glu Ala Arg Arg Cys Ala Arg Arg
    50                  55                  60
Glu Glu Leu Leu Ala Arg Gly Cys Pro Ala Gln Glu Leu Glu Pro
65                  70                  75                  80
Arg Gly Arg Gln Glu Val Leu Gln Asp Lys Pro Leu Ser Gln Gly Asp
                85                  90                  95
Arg Gly Glu Gly Ala Thr Gln Leu Pro Gln Arg Ile Arg Val Thr Leu
            100                 105                 110
```

-continued

```
Arg Pro Gly Glu Pro Gln Lys Phe Arg Val Arg Phe Leu Arg Ala Ala
        115                 120                 125
Gly Tyr Pro Val Asp Leu Tyr Tyr Leu Met Asp Leu Ser Tyr Ser Met
130                 135                 140
Lys Asp Asp Leu Glu Arg Val Arg Gln Leu Gly His Ala Leu Leu Val
145                 150                 155                 160
Arg Leu Gln Glu Val Thr His Ser Val Arg Ile Gly Phe Gly Ser Phe
                165                 170                 175
Val Asp Lys Thr Val Leu Pro Phe Val Ser Thr Val Pro Ser Lys Leu
            180                 185                 190
His His Pro Cys Pro Ser Arg Leu Glu Arg Cys Gln Pro Pro Phe Ser
        195                 200                 205
Phe His His Val Leu Ser Leu Thr Gly Asp Ala Gln Ala Phe Glu Arg
    210                 215                 220
Glu Val Gly Arg Gln Asn Val Ser Gly Asn Leu Asp Ser Pro Glu Gly
225                 230                 235                 240
Gly Phe Asp Ala Ile Leu Gln Ala Ala Leu Cys Gln Glu Gln Ile Gly
                245                 250                 255
Trp Arg Asn Val Ser Arg Leu Leu Val Phe Thr Ser Asp Asp Thr Phe
            260                 265                 270
His Thr Ala Gly Asp Gly Lys Leu Gly Gly Ile Phe Met Pro Ser Asp
        275                 280                 285
Gly Arg Cys His Leu Asp Ser Asn Gly Val Tyr Thr Asn Ser Ala Glu
    290                 295                 300
Phe Asp Tyr Pro Ser Val Gly Gln Val Ala Gln Ala Leu Thr Ala Ala
305                 310                 315                 320
Asn Ile Gln Pro Ile Phe Ala Val Thr Gly Ala Thr Leu Pro Val Tyr
                325                 330                 335
Gln Glu Leu Arg Gln Leu Ile Pro Lys Ser Ala Val Gly Glu Leu Ser
            340                 345                 350
Glu Asp Ser Ser Asn Val Val Gln Leu Ile Met Asp Ala Tyr Asp Ser
        355                 360                 365
Leu Ser Ser Thr Val Thr Leu Glu His Ser Pro Leu Pro Pro Gly Val
    370                 375                 380
Ser Ile Ser Phe Glu Ser His Cys Lys Gly Pro Glu Lys Thr Glu Gly
385                 390                 395                 400
Glu Ala Gly Asp Arg Gly Gln Cys Asn Asp Val Arg Val Asn Gln Thr
                405                 410                 415
Val Asp Phe Trp Val Thr Leu Gln Ala Thr His Cys Leu Pro Glu Ala
            420                 425                 430
His Val Leu Arg Leu Trp Ala Leu Gly Phe Ser Glu Glu Leu Thr Val
        435                 440                 445
Glu Leu His Thr Val Cys Asp Cys Asn Cys Gly Asp Ala Gln Pro His
    450                 455                 460
Ala Pro Tyr Cys Ser Asp Gly Gln Gly Asp Leu Gln Cys Gly Ile Cys
465                 470                 475                 480
Ser Cys Ala Pro Gly Arg Leu Gly Gln Leu Cys Glu Cys Ser Glu Ala
                485                 490                 495
Asp Leu Ser Ser Pro Asp Leu Glu Ser Gly Cys Arg Ala Pro Asn Gly
            500                 505                 510
Thr Gly Pro Leu Cys Ser Gly Lys Gly Arg Cys Gln Cys Gly Arg Cys
        515                 520                 525
Ser Cys Ser Gly Gln Ser Ser Gly His Leu Cys Glu Cys Asp Asp Ala
```

```
                530                 535                 540
Ser Cys Glu Arg His Glu Gly Ile Leu Cys Gly Gly Phe Gly His Cys
545                 550                 555                 560

Gln Cys Gly Val Cys His Cys His Ala Asn His Thr Gly Arg Ala Cys
                565                 570                 575

Glu Cys Ser Lys Ser Val Asp Ser Cys Val Ser Pro Glu Gly Gly Leu
                580                 585                 590

Cys Ser Gly His Gly Tyr Cys Lys Cys Asn Arg Cys Gln Cys Leu Asp
                595                 600                 605

Gly Tyr Tyr Gly Ala Leu Cys Asp Gln Cys Leu Gly Cys Lys Ser Pro
610                 615                 620

Cys Glu Gln Tyr Arg Asp Cys Ala Glu Cys Gly Ala Phe Gly Thr Gly
625                 630                 635                 640

Pro Leu Ala Ala Asn Cys Ser Val Val Cys Ala Asp Val Asn Val Thr
                645                 650                 655

Leu Thr Leu Ala Pro Asn Leu Asp Asp Gly Trp Cys Lys Glu Arg Thr
                660                 665                 670

Ile Asp Asn Gln Leu Phe Phe Phe Leu Val Glu His Ala Ala Ser Gly
                675                 680                 685

Ile Val Leu Arg Val Arg Pro Gln Glu Lys Gly Val Asp His Thr Arg
                690                 695                 700

Ala Ile Ile Leu Gly Cys Thr Gly Gly Ile Val Ala Val Gly Leu Gly
705                 710                 715                 720

Leu Val Leu Ala Tyr Arg Leu Ser Val Glu Ile Tyr Asp Arg Arg Glu
                725                 730                 735

Tyr Arg Arg Phe Glu Lys Glu Gln Gln Gln Leu Asn Trp Lys Gln Asp
                740                 745                 750

Asn Asn Pro Leu Tyr Lys Ser Ala Ile Thr Thr Thr Val Asn Pro Arg
                755                 760                 765

Phe Gln Gly Thr Asn Gly Arg Ser Pro Ser Leu Ser Leu Thr Arg Glu
                770                 775                 780

Ala Asp
785

<210> SEQ ID NO 46
<211> LENGTH: 727
<212> TYPE: PRT
<213> ORGANISM: Homo sapiens

<400> SEQUENCE: 46

Glu Asp Asn Arg Cys Ala Ser Ser Asn Ala Ala Ser Cys Ala Arg Cys
1               5                   10                  15

Leu Ala Leu Gly Pro Glu Cys Gly Trp Cys Val Gln Glu Asp Phe Ile
                20                  25                  30

Ser Gly Gly Ser Arg Ser Glu Arg Cys Asp Ile Val Ser Asn Leu Ile
            35                  40                  45

Ser Lys Gly Cys Ser Val Asp Ser Ile Glu Tyr Pro Ser Val His Val
        50                  55                  60

Ile Ile Pro Thr Glu Asn Glu Ile Asn Thr Gln Val Thr Pro Gly Glu
65                  70                  75                  80

Val Ser Ile Gln Leu Arg Pro Gly Ala Glu Ala Asn Phe Met Leu Lys
                85                  90                  95

Val His Pro Leu Lys Lys Tyr Pro Val Asp Leu Tyr Tyr Leu Val Asp
                100                 105                 110
```

-continued

```
Val Ser Ala Ser Met His Asn Asn Ile Glu Lys Leu Asn Ser Val Gly
            115                 120                 125

Asn Asp Leu Ser Arg Lys Met Ala Phe Phe Ser Arg Asp Phe Arg Leu
130                 135                 140

Gly Phe Gly Ser Tyr Val Asp Lys Thr Val Ser Pro Tyr Ile Ser Ile
145                 150                 155                 160

His Pro Glu Arg Ile His Asn Gln Cys Ser Asp Tyr Asn Leu Asp Cys
                165                 170                 175

Met Pro Pro His Gly Tyr Ile His Val Leu Ser Leu Thr Glu Asn Ile
            180                 185                 190

Thr Glu Phe Glu Lys Ala Val His Arg Gln Lys Ile Ser Gly Asn Ile
            195                 200                 205

Asp Thr Pro Glu Gly Gly Phe Asp Ala Met Leu Gln Ala Ala Val Cys
210                 215                 220

Glu Ser His Ile Gly Trp Arg Lys Glu Ala Lys Arg Leu Leu Leu Val
225                 230                 235                 240

Met Thr Asp Gln Thr Ser His Leu Ala Leu Asp Ser Lys Leu Ala Gly
                245                 250                 255

Ile Val Val Pro Asn Asp Gly Asn Cys His Leu Lys Asn Asn Val Tyr
            260                 265                 270

Val Lys Ser Thr Thr Met Glu His Pro Ser Leu Gly Gln Leu Ser Glu
            275                 280                 285

Lys Leu Ile Asp Asn Asn Ile Asn Val Ile Phe Ala Val Gln Gly Lys
290                 295                 300

Gln Phe His Trp Tyr Lys Asp Leu Leu Pro Leu Leu Pro Gly Thr Ile
305                 310                 315                 320

Ala Gly Glu Ile Glu Ser Lys Ala Ala Asn Leu Asn Asn Leu Val Val
                325                 330                 335

Glu Ala Tyr Gln Lys Leu Ile Ser Glu Val Lys Val Gln Val Glu Asn
            340                 345                 350

Gln Val Gln Gly Ile Tyr Phe Asn Ile Thr Ala Ile Cys Pro Asp Gly
            355                 360                 365

Ser Arg Lys Pro Gly Met Glu Gly Cys Arg Asn Val Thr Ser Asn Asp
370                 375                 380

Glu Val Leu Phe Asn Val Thr Val Thr Met Lys Lys Cys Asp Val Thr
385                 390                 395                 400

Gly Gly Lys Asn Tyr Ala Ile Ile Lys Pro Ile Gly Phe Asn Glu Thr
                405                 410                 415

Ala Lys Ile His Ile His Arg Asn Cys Ser Cys Gln Cys Glu Asp Asn
            420                 425                 430

Arg Gly Pro Lys Gly Lys Cys Val Asp Glu Thr Phe Leu Asp Ser Lys
            435                 440                 445

Cys Phe Gln Cys Asp Glu Asn Lys Cys His Phe Asp Glu Asp Gln Phe
450                 455                 460

Ser Ser Glu Ser Cys Lys Ser His Lys Asp Gln Pro Val Cys Ser Gly
465                 470                 475                 480

Arg Gly Val Cys Val Cys Gly Lys Cys Ser Cys His Lys Ile Lys Leu
                485                 490                 495

Gly Lys Val Tyr Gly Lys Tyr Cys Glu Lys Asp Phe Ser Cys Pro
            500                 505                 510

Tyr His His Gly Asn Leu Cys Ala Gly His Gly Glu Cys Glu Ala Gly
            515                 520                 525

Arg Cys Gln Cys Phe Ser Gly Trp Glu Gly Asp Arg Cys Gln Cys Pro
```

```
              530              535              540
Ser Ala Ala Gln His Cys Val Asn Ser Lys Gly Gln Val Cys Ser
545                 550                 555                 560

Gly Arg Gly Thr Cys Val Cys Gly Arg Cys Glu Cys Thr Asp Pro Arg
                565                 570                 575

Ser Ile Gly Arg Phe Cys Glu His Cys Pro Thr Cys Tyr Thr Ala Cys
                580                 585                 590

Lys Glu Asn Trp Asn Cys Met Gln Cys Leu His Pro His Asn Leu Ser
                595                 600                 605

Gln Ala Ile Leu Asp Gln Cys Lys Thr Ser Cys Ala Leu Met Glu Gln
610                 615                 620

Gln His Tyr Val Asp Gln Thr Ser Glu Cys Phe Ser Ser Pro Ser Tyr
625                 630                 635                 640

Leu Arg Ile Phe Phe Ile Ile Phe Ile Val Thr Phe Leu Ile Gly Leu
                645                 650                 655

Leu Lys Val Leu Ile Ile Arg Gln Val Ile Leu Gln Trp Asn Ser Asn
                660                 665                 670

Lys Ile Lys Ser Ser Ser Asp Tyr Arg Val Ser Ala Ser Lys Lys Asp
                675                 680                 685

Lys Leu Ile Leu Gln Ser Val Cys Thr Arg Ala Val Thr Tyr Arg Arg
                690                 695                 700

Glu Lys Pro Glu Glu Ile Lys Met Asp Ile Ser Lys Leu Asn Ala His
705                 710                 715                 720

Glu Thr Phe Arg Cys Asn Phe
                725

<210> SEQ ID NO 47
<211> LENGTH: 649
<212> TYPE: PRT
<213> ORGANISM: Mus musculus

<400> SEQUENCE: 47

Gln Leu Cys Thr Lys Asp Asn Val Ser Thr Cys Gln Asp Cys Ile Arg
1               5                   10                  15

Ser Gly Pro Ser Cys Ala Trp Cys Gln Lys Leu Asn Phe Thr Gly Arg
                20                  25                  30

Gly Glu Pro Asp Ser Val Arg Cys Asp Thr Pro Glu Gln Leu Leu Leu
            35                  40                  45

Lys Gly Cys Thr Ser Glu Tyr Leu Val Asp Pro Lys Ser Leu Ala Glu
    50                  55                  60

Ser Gln Glu Asp Lys Glu Arg Asp Gln Arg Gln Leu Ser Pro Arg Asn
65                  70                  75                  80

Val Thr Val Phe Leu Arg Pro Gly Gln Ala Ala Thr Phe Lys Val Asp
                85                  90                  95

Phe Gln Arg Thr Gln Asp Asn Ser Val Asp Leu Tyr Phe Leu Met Gly
                100                 105                 110

Leu Ser Gly Ser Ala Gln Gly His Leu Ser Asn Val Gln Thr Leu Gly
            115                 120                 125

Ser Asp Leu Leu Lys Ala Leu Asn Glu Ile Ser Arg Ser Gly Arg Ile
130                 135                 140

Gly Phe Gly Ser Ile Val Asn Met Thr Phe Gln His Ile Leu Lys Leu
145                 150                 155                 160

Thr Ala Asp Ser Ser Gln Phe Gln Arg Glu Leu Arg Lys Gln Leu Val
                165                 170                 175
```

-continued

```
Ser Gly Lys Leu Ala Thr Pro Lys Gly Gln Leu Asp Ala Val Val Gln
            180                 185                 190

Val Ala Ile Cys Leu Gly Glu Ile Gly Trp Arg Asn Gly Thr Arg Phe
        195                 200                 205

Leu Val Leu Val Thr Asp Asn Asp Phe His Leu Ala Lys Asp Lys Thr
    210                 215                 220

Leu Gly Thr Arg Gln Asn Thr Ser Asp Gly Arg Cys His Leu Asp Asp
225                 230                 235                 240

Gly Met Tyr Arg Ser Arg Gly Glu Pro Asp Tyr Gln Ser Val Val Gln
                245                 250                 255

Leu Ala Ser Lys Leu Ala Glu Asn Asn Ile Gln Pro Ile Phe Val Val
            260                 265                 270

Pro Ser Arg Met Val Lys Thr Tyr Glu Lys Leu Thr Thr Phe Ile Pro
        275                 280                 285

Lys Leu Thr Ile Gly Glu Leu Ser Asp Asp Ser Ser Asn Val Ala Gln
    290                 295                 300

Leu Ile Arg Asn Ala Tyr Ser Lys Leu Ser Ser Ile Val Val Leu Asn
305                 310                 315                 320

His Ser Thr Ile Pro Ser Ile Leu Lys Val Thr Tyr Asp Ser Tyr Cys
                325                 330                 335

Ser Asn Gly Thr Ser Asn Pro Gly Lys Pro Ser Gly Asp Cys Ser Gly
            340                 345                 350

Val Gln Ile Asn Asp Gln Val Thr Phe Gln Val Asn Ile Thr Ala Ser
        355                 360                 365

Glu Cys Phe Arg Glu Gln Phe Phe Phe Ile Gln Ala Leu Gly Phe Met
    370                 375                 380

Asp Ser Val Thr Val Arg Val Leu Pro Leu Cys Glu Cys Gln Cys Gln
385                 390                 395                 400

Glu Gln Ser Gln His His Ser Leu Cys Gly Gly Lys Gly Ala Met Glu
                405                 410                 415

Cys Gly Ile Cys Arg Cys Asn Ser Gly Tyr Ala Gly Lys Asn Cys Glu
            420                 425                 430

Cys Gln Thr Gln Gly Pro Ser Ser Gln Asp Leu Glu Gly Ser Cys Arg
        435                 440                 445

Lys Asp Asn Ser Ser Ile Met Cys Ser Gly Leu Gly Asp Cys Ile Cys
450                 455                 460

Gly Gln Cys Glu Cys His Thr Ser Asp Ile Pro Asn Lys Glu Ile Tyr
465                 470                 475                 480

Gly Gln Tyr Cys Glu Cys Asp Asn Val Asn Cys Glu Arg Tyr Asp Gly
                485                 490                 495

Gln Val Cys Gly Gly Pro Glu Arg Gly His Cys Ser Cys Gly Arg Cys
            500                 505                 510

Phe Cys Arg Tyr Ser Phe Val Gly Ser Ala Cys Gln Cys Arg Met Ser
        515                 520                 525

Thr Ser Gly Cys Leu Asn Asn Arg Met Val Glu Cys Ser Gly His Gly
    530                 535                 540

Arg Cys Tyr Cys Asn Arg Cys Leu Cys Asp Pro Gly Tyr Gln Pro Pro
545                 550                 555                 560

Leu Cys Glu Lys Arg Pro Gly Tyr Phe His Arg Cys Ser Glu Tyr Tyr
                565                 570                 575

Ser Cys Ala Arg Cys Leu Lys Asp Asn Ser Ala Ile Lys Cys Arg Glu
            580                 585                 590

Cys Trp Asn Leu Leu Phe Ser Asn Thr Pro Phe Ser Asn Lys Thr Cys
```

```
              595                 600                 605
Met Thr Glu Arg Asp Ser Glu Gly Cys Trp Thr Thr Tyr Thr Leu Tyr
              610                 615                 620

Gln Pro Asp Gln Ser Asp Ile Asn Ser Ile Tyr Ile Lys Glu Ser Leu
625                 630                 635                 640

Val Cys Ala Glu Ile Ser Asn Thr Thr
                645
```

<210> SEQ ID NO 48
<211> LENGTH: 18
<212> TYPE: PRT
<213> ORGANISM: Homo sapiens

<400> SEQUENCE: 48

```
Arg Gly Glu Ala Gln Val Trp Thr Gln Leu Leu Arg Ala Cys Glu Glu
1               5                   10                  15

Arg Ala
```

<210> SEQ ID NO 49
<211> LENGTH: 18
<212> TYPE: PRT
<213> ORGANISM: Homo sapiens

<400> SEQUENCE: 49

```
Arg Gly Glu Ala Gln Val Trp Thr Gln Leu Leu Arg Ala Leu Cys Glu
1               5                   10                  15

Arg Ala
```

<210> SEQ ID NO 50
<211> LENGTH: 19
<212> TYPE: PRT
<213> ORGANISM: Homo sapiens

<400> SEQUENCE: 50

```
Thr Asn Ser Thr Leu Val Thr Thr Asn Val Thr Trp Gly Cys Gln Pro
1               5                   10                  15

Ala Pro Met
```

<210> SEQ ID NO 51
<211> LENGTH: 19
<212> TYPE: PRT
<213> ORGANISM: Homo sapiens

<400> SEQUENCE: 51

```
Thr Asn Ser Thr Leu Val Thr Thr Asn Val Thr Trp Gly Ile Cys Pro
1               5                   10                  15

Ala Pro Met
```

<210> SEQ ID NO 52
<211> LENGTH: 28
<212> TYPE: PRT
<213> ORGANISM: Homo sapiens

<400> SEQUENCE: 52

```
Cys Cys Val Arg Phe Gln Tyr Tyr Glu Asp Ser Ser Gly Lys Ser Ile
1               5                   10                  15

Leu Tyr Val Val Glu Glu Pro Glu Cys Pro Lys Gly
                20                  25
```

<210> SEQ ID NO 53

```
<211> LENGTH: 28
<212> TYPE: PRT
<213> ORGANISM: Homo sapiens

<400> SEQUENCE: 53

Cys Val Val Arg Phe Gln Tyr Tyr Glu Asp Ser Ser Gly Lys Ser Ile
1               5                   10                  15

Leu Tyr Val Val Glu Glu Pro Glu Cys Cys Lys Gly
            20                  25

<210> SEQ ID NO 54
<211> LENGTH: 26
<212> TYPE: PRT
<213> ORGANISM: Homo sapiens

<400> SEQUENCE: 54

Cys Cys Ile Thr Phe Leu Ile Thr Thr Asp Asn Glu Gly Lys Thr His
1               5                   10                  15

Ser Ile Asn Glu Lys Asp Cys Pro Lys Pro
            20                  25

<210> SEQ ID NO 55
<211> LENGTH: 26
<212> TYPE: PRT
<213> ORGANISM: Homo sapiens

<400> SEQUENCE: 55

Cys Leu Ile Thr Phe Leu Ile Thr Thr Asp Asn Glu Gly Lys Thr His
1               5                   10                  15

Ser Ile Asn Glu Lys Asp Cys Cys Lys Pro
            20                  25

<210> SEQ ID NO 56
<211> LENGTH: 19
<212> TYPE: PRT
<213> ORGANISM: Homo sapiens

<400> SEQUENCE: 56

Cys Cys Leu Met Glu Gln Gln His Tyr Val Asp Gln Thr Ser Glu Cys
1               5                   10                  15

Phe Ser Ser

<210> SEQ ID NO 57
<211> LENGTH: 19
<212> TYPE: PRT
<213> ORGANISM: Homo sapiens

<400> SEQUENCE: 57

Cys Ala Leu Met Glu Gln Gln His Tyr Val Asp Gln Thr Ser Glu Cys
1               5                   10                  15

Cys Ser Ser

<210> SEQ ID NO 58
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gln Leu Leu Arg Ala Leu Glu Glu Arg Ala Thr Gly Gly Leu Glu Asn
1               5                   10                  15
```

```
Leu Tyr Phe Gln Gly Gly Glu Asn Ala Gln Cys Glu Lys Glu Leu Gln
                20                  25                  30

Ala Leu Glu Lys Glu Asn Ala Gln Leu Glu Trp Glu Leu Gln Ala Leu
            35                  40                  45

Glu Lys Glu Leu Ala Gln Trp Ser His Pro Gln Phe Glu Lys
    50                  55                  60
```

```
<210> SEQ ID NO 59
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Val Val Glu Glu Pro Glu Cys Pro Lys Gly Thr Ser Gly Leu Glu Asn
1               5                   10                  15

Leu Tyr Phe Gln Gly Gly Lys Asn Ala Gln Cys Lys Lys Lys Leu Gln
                20                  25                  30

Ala Leu Lys Lys Lys Asn Ala Gln Leu Lys Trp Lys Leu Gln Ala Leu
            35                  40                  45

Lys Lys Lys Leu Ala Gln Gly Gly His His His His His His
    50                  55                  60
```

```
<210> SEQ ID NO 60
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Glu Lys Gly Cys Gly Leu Gln Thr Leu Phe Gln Gly Pro Leu Gly Ala
1               5                   10                  15

Gln Gly Glu Lys Glu Leu Gln Ala Leu Glu Lys Glu Asn Ala Gln Leu
                20                  25                  30

Glu Trp Glu Leu Gln Ala Leu Glu Lys Glu Leu Ala Gln His His His
            35                  40                  45

His His His
    50
```

```
<210> SEQ ID NO 61
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Glu Lys Tyr Gly Cys Gly Leu Gln Thr Leu Phe Gln Gly Pro Leu Gly
1               5                   10                  15

Ala Gln Gly Glu Lys Glu Leu Gln Ala Leu Glu Lys Glu Asn Ala Gln
                20                  25                  30

Leu Glu Trp Glu Leu Gln Ala Leu Glu Lys Glu Leu Ala Gln His His
            35                  40                  45

His His His His
    50
```

<210> SEQ ID NO 62
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Glu Lys Tyr Lys Gly Cys Gly Leu Gln Thr Leu Phe Gln Gly Pro Leu
1               5                   10                  15

Gly Ala Gln Gly Glu Lys Glu Leu Gln Ala Leu Glu Lys Glu Asn Ala
            20                  25                  30

Gln Leu Glu Trp Glu Leu Gln Ala Leu Glu Lys Glu Leu Ala Gln His
        35                  40                  45

His His His His His
    50

<210> SEQ ID NO 63
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Glu Lys Tyr Lys Val Gly Cys Gly Leu Gln Thr Leu Phe Gln Gly Pro
1               5                   10                  15

Leu Gly Ala Gln Gly Glu Lys Glu Leu Gln Ala Leu Glu Lys Glu Asn
            20                  25                  30

Ala Gln Leu Glu Trp Glu Leu Gln Ala Leu Glu Lys Glu Leu Ala Gln
        35                  40                  45

His His His His His His
    50

<210> SEQ ID NO 64
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Glu Lys Tyr Lys Val His Gly Cys Gly Leu Gln Thr Leu Phe Gln Gly
1               5                   10                  15

Pro Leu Gly Ala Gln Gly Glu Lys Glu Leu Gln Ala Leu Glu Lys Glu
            20                  25                  30

Asn Ala Gln Leu Glu Trp Glu Leu Gln Ala Leu Glu Lys Glu Leu Ala
        35                  40                  45

Gln His His His His His His
    50                  55

<210> SEQ ID NO 65
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

```
Glu Cys Gly Cys Gly Leu Gln Thr Leu Phe Gln Gly Pro Leu Gly Ala
1               5                   10                  15

Gln Gly Lys Lys Lys Leu Gln Ala Leu Lys Lys Lys Asn Ala Gln Leu
            20                  25                  30

Lys Trp Lys Leu Gln Ala Leu Lys Lys Lys Leu Ala Gln His His His
        35                  40                  45

His His His
    50

<210> SEQ ID NO 66
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Glu Cys Val Gly Cys Gly Leu Gln Thr Leu Phe Gln Gly Pro Leu Gly
1               5                   10                  15

Ala Gln Gly Lys Lys Lys Leu Gln Ala Leu Lys Lys Lys Asn Ala Gln
            20                  25                  30

Leu Lys Trp Lys Leu Gln Ala Leu Lys Lys Lys Leu Ala Gln His His
        35                  40                  45

His His His His
    50

<210> SEQ ID NO 67
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Glu Cys Val Ala Gly Cys Gly Leu Gln Thr Leu Phe Gln Gly Pro Leu
1               5                   10                  15

Gly Ala Gln Gly Lys Lys Lys Leu Gln Ala Leu Lys Lys Lys Asn Ala
            20                  25                  30

Gln Leu Lys Trp Lys Leu Gln Ala Leu Lys Lys Lys Leu Ala Gln His
        35                  40                  45

His His His His His
    50

<210> SEQ ID NO 68
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Glu Cys Val Ala Gly Gly Cys Gly Leu Gln Thr Leu Phe Gln Gly Pro
1               5                   10                  15

Leu Gly Ala Gln Gly Lys Lys Lys Leu Gln Ala Leu Lys Lys Lys Asn
            20                  25                  30

Ala Gln Leu Lys Trp Lys Leu Gln Ala Leu Lys Lys Lys Leu Ala Gln
        35                  40                  45
```

His His His His His His
    50

<210> SEQ ID NO 69
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Glu Cys Val Ala Gly Pro Gly Cys Gly Leu Gln Thr Leu Phe Gln Gly
1               5                   10                  15

Pro Leu Gly Ala Gln Gly Lys Lys Lys Leu Gln Ala Leu Lys Lys Lys
            20                  25                  30

Asn Ala Gln Leu Lys Trp Lys Leu Gln Ala Leu Lys Lys Lys Leu Ala
        35                  40                  45

Gln His His His His His His
    50                  55

<210> SEQ ID NO 70
<211> LENGTH: 12
<212> TYPE: PRT
<213> ORGANISM: Homo sapiens

<400> SEQUENCE: 70

Glu Lys Tyr Lys Val His Asn Pro Thr Pro Leu Ile
1               5                   10

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Glu Lys Tyr Gly Cys Gly
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Glu Lys Tyr Lys Gly Cys Gly
1               5

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Glu Lys Tyr Lys Val Gly Cys Gly
1               5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Glu Lys Tyr Lys Val His Gly Cys Gly
1               5

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Glu Lys Tyr Lys Val His Asn Gly Cys Gly
1               5                   10

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Glu Cys Gly Cys Gly
1               5

<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Glu Cys Val Gly Cys Gly
1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Glu Cys Val Ala Gly Cys Gly
1               5

<210> SEQ ID NO 79
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 79

Glu Cys Val Ala Gly Gly Cys Gly
1               5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Glu Cys Val Ala Gly Pro Gly Cys Gly
1               5

<210> SEQ ID NO 81
<211> LENGTH: 10
<212> TYPE: PRT
<213> ORGANISM: Homo sapiens

<400> SEQUENCE: 81

Glu Cys Val Ala Gly Pro Asn Ile Ala Ala
1               5                   10

<210> SEQ ID NO 82
<211> LENGTH: 4
<212> TYPE: PRT
<213> ORGANISM: Unknown
<220> FEATURE:
<223> OTHER INFORMATION: Description of Unknown: Integrin alpha sequence

<400> SEQUENCE: 82

Arg Ala Leu Glu
1

<210> SEQ ID NO 83
<211> LENGTH: 7
<212> TYPE: PRT
<213> ORGANISM: Unknown
<220> FEATURE:
<223> OTHER INFORMATION: Description of Unknown: Integrin beta sequence

<400> SEQUENCE: 83

Pro Asp Ile Leu Val Val Leu
1               5

<210> SEQ ID NO 84
<211> LENGTH: 8
<212> TYPE: PRT
<213> ORGANISM: Unknown
<220> FEATURE:
<223> OTHER INFORMATION: Description of Unknown: Integrin beta sequence

<400> SEQUENCE: 84

Pro Asp Ile Leu Val Val Leu Leu
1               5

<210> SEQ ID NO 85
<211> LENGTH: 29
<212> TYPE: PRT
<213> ORGANISM: Homo sapiens

<400> SEQUENCE: 85

Leu Tyr Gly Ser Asn Ala Ser Leu Ala Gln Val Val Met Lys Val Asp
1               5                   10                  15
```

Val Val Tyr Glu Lys Gln Met Leu Tyr Leu Tyr Val Leu
            20                  25

<210> SEQ ID NO 86
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Leu Tyr Gly Ser Asn Ala Ser Leu Ala Gln Val Val Met Lys Val Asp
1               5                   10                  15

Val Val Tyr Cys Lys Gln Met Leu Tyr Leu Tyr Val Leu
            20                  25

<210> SEQ ID NO 87
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Leu Tyr Gly Ser Asn Ala Ser Leu Ala Gln Val Val Met Lys Val Asp
1               5                   10                  15

Val Val Tyr Glu Cys Gln Met Leu Tyr Leu Tyr Val Leu
            20                  25

<210> SEQ ID NO 88
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Leu Tyr Gly Ser Asn Ala Ser Leu Ala Gln Val Val Met Lys Val Asp
1               5                   10                  15

Val Val Tyr Glu Lys Cys Met Leu Tyr Leu Tyr Val Leu
            20                  25

<210> SEQ ID NO 89
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Leu Tyr Gly Ser Asn Ala Ser Leu Ala Gln Val Val Met Lys Val Asp
1               5                   10                  15

Val Val Tyr Glu Lys Gln Cys Leu Tyr Leu Tyr Val Leu
            20                  25

<210> SEQ ID NO 90
<211> LENGTH: 29
<212> TYPE: PRT
<213> ORGANISM: Homo sapiens

<400> SEQUENCE: 90

```
Met Asp Arg Tyr Leu Ile Tyr Val Asp Glu Ser Arg Glu Cys Val Ala
1               5                   10                  15

Gly Pro Asn Ile Ala Ala Ile Val Gly Gly Thr Val Ala
            20                  25

<210> SEQ ID NO 91
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Met Asp Arg Tyr Leu Ile Tyr Val Asp Glu Ser Arg Cys Cys Val Ala
1               5                   10                  15

Gly Pro Asn Ile Ala Ala Ile Val Gly Gly Thr Val Ala
            20                  25

<210> SEQ ID NO 92
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Met Asp Arg Tyr Leu Ile Tyr Val Asp Glu Ser Arg Glu Cys Val Ala
1               5                   10                  15

Cys Pro Asn Ile Ala Ala Ile Val Gly Gly Thr Val Ala
            20                  25

<210> SEQ ID NO 93
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Met Asp Arg Tyr Leu Ile Tyr Val Asp Glu Ser Arg Glu Cys Val Ala
1               5                   10                  15

Gly Cys Asn Ile Ala Ala Ile Val Gly Gly Thr Val Ala
            20                  25

<210> SEQ ID NO 94
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Met Asp Arg Tyr Leu Ile Tyr Val Asp Glu Ser Arg Glu Cys Val Ala
1               5                   10                  15

Gly Pro Cys Ile Ala Ala Ile Val Gly Gly Thr Val Ala
            20                  25

<210> SEQ ID NO 95
<211> LENGTH: 56
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 95

Tyr Glu Lys Gln Thr Gly Gly Leu Glu Asn Leu Tyr Phe Gln Gly Gly
1               5                   10                  15

Glu Asn Ala Gln Cys Glu Lys Glu Leu Gln Ala Leu Glu Lys Glu Asn
            20                  25                  30

Ala Gln Leu Glu Trp Glu Leu Gln Ala Leu Glu Lys Glu Leu Ala Gln
        35                  40                  45

Trp Ser His Pro Gln Phe Glu Lys
    50                  55

<210> SEQ ID NO 96
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Tyr Cys Lys Gln Thr Gly Gly Leu Glu Asn Leu Tyr Phe Gln Gly Gly
1               5                   10                  15

Glu Asn Ala Gln Cys Glu Lys Glu Leu Gln Ala Leu Glu Lys Glu Asn
            20                  25                  30

Ala Gln Leu Glu Trp Glu Leu Gln Ala Leu Glu Lys Glu Leu Ala Gln
        35                  40                  45

Trp Ser His Pro Gln Phe Glu Lys
    50                  55

<210> SEQ ID NO 97
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Tyr Glu Lys Gly Cys Gly Gly Leu Glu Asn Leu Tyr Phe Gln Gly Gly
1               5                   10                  15

Glu Asn Ala Gln Cys Glu Lys Glu Leu Gln Ala Leu Glu Lys Glu Asn
            20                  25                  30

Ala Gln Leu Glu Trp Glu Leu Gln Ala Leu Glu Lys Glu Leu Ala Gln
        35                  40                  45

Trp Ser His Pro Gln Phe Glu Lys
    50                  55

<210> SEQ ID NO 98
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Tyr Lys Val His Gly Thr Gly Gly Leu Glu Asn Leu Tyr Phe Gln Gly
1               5                   10                  15
```

Gly Glu Asn Ala Gln Cys Glu Lys Glu Leu Gln Ala Leu Glu Lys Glu
            20                  25                  30

Asn Ala Gln Leu Glu Trp Glu Leu Gln Ala Leu Glu Lys Glu Leu Ala
        35                  40                  45

Gln Trp Ser His Pro Gln Phe Glu Lys
    50                  55

<210> SEQ ID NO 99
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Tyr Lys Val His Gly Cys Gly Gly Leu Glu Asn Leu Tyr Phe Gln Gly
1               5                   10                  15

Gly Glu Asn Ala Gln Cys Glu Lys Glu Leu Gln Ala Leu Glu Lys Glu
            20                  25                  30

Asn Ala Gln Leu Glu Trp Glu Leu Gln Ala Leu Glu Lys Glu Leu Ala
        35                  40                  45

Gln Trp Ser His Pro Gln Phe Glu Lys
    50                  55

<210> SEQ ID NO 100
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Val Ala Gly Pro Asp Thr Ser Gly Leu Glu Asn Leu Tyr Phe Gln Gly
1               5                   10                  15

Gly Lys Asn Ala Gln Cys Lys Lys Lys Leu Gln Ala Leu Lys Lys Lys
            20                  25                  30

Asn Ala Gln Leu Lys Trp Lys Leu Gln Ala Leu Lys Lys Lys Leu Ala
        35                  40                  45

Gln Gly Gly His His His His His His
    50                  55

<210> SEQ ID NO 101
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Cys Ala Gly Pro Asp Thr Ser Gly Leu Glu Asn Leu Tyr Phe Gln Gly
1               5                   10                  15

Gly Lys Asn Ala Gln Cys Lys Lys Lys Leu Gln Ala Leu Lys Lys Lys
            20                  25                  30

Asn Ala Gln Leu Lys Trp Lys Leu Gln Ala Leu Lys Lys Lys Leu Ala
        35                  40                  45

Gln Gly Gly His His His His His His
    50                  55

```
<210> SEQ ID NO 102
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Val Ala Cys Pro Asp Thr Ser Gly Leu Glu Asn Leu Tyr Phe Gln Gly
1               5                   10                  15

Gly Lys Asn Ala Gln Cys Lys Lys Lys Leu Gln Ala Leu Lys Lys Lys
            20                  25                  30

Asn Ala Gln Leu Lys Trp Lys Leu Gln Ala Leu Lys Lys Lys Leu Ala
        35                  40                  45

Gln Gly Gly His His His His His His
    50                  55

<210> SEQ ID NO 103
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Val Ala Gly Pro Asp Gly Cys Gly Leu Glu Asn Leu Tyr Phe Gln Gly
1               5                   10                  15

Gly Lys Asn Ala Gln Cys Lys Lys Lys Leu Gln Ala Leu Lys Lys Lys
            20                  25                  30

Asn Ala Gln Leu Lys Trp Lys Leu Gln Ala Leu Lys Lys Lys Leu Ala
        35                  40                  45

Gln Gly Gly His His His His His His
    50                  55

<210> SEQ ID NO 104
<211> LENGTH: 10
<212> TYPE: PRT
<213> ORGANISM: Homo sapiens

<400> SEQUENCE: 104

Val Val Tyr Glu Lys Gln Met Leu Tyr Leu
1               5                   10

<210> SEQ ID NO 105
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 105

His His His His His His
1               5
```